United States Patent
Shiono

(10) Patent No.: US 6,329,546 B1
(45) Date of Patent: Dec. 11, 2001

(54) CAGED AMINO ACIDS

(75) Inventor: Hirofumi Shiono, Shizuoka (JP)

(73) Assignee: Laboratory of Molecular Biophotonics, Hamakita (JP)

( * ) Notice: Subject to any disclaimer, the term of this patent is extended or adjusted under 35 U.S.C. 154(b) by 0 days.

(21) Appl. No.: 09/480,458

(22) Filed: Jan. 11, 2000

(30) Foreign Application Priority Data

Jan. 12, 1999 (JP) .................................. 11-005660

(51) Int. Cl.[7] .................................. C07C 235/36

(52) U.S. Cl. ..................... 562/455; 562/433; 562/426
(58) Field of Search ..................... 548/542, 545; 562/450, 443, 433, 455

(56) References Cited

U.S. PATENT DOCUMENTS 6,229,020 * 5/2001 Shiono .................................. 548/110

FOREIGN PATENT DOCUMENTS

| 50-30842 | * | 3/1975 | (JP) . |
| 11-29500 | | 2/1999 | (JP) . |
| WO 91/03549 | | 3/1991 | (WO) . |

OTHER PUBLICATIONS

N–Protected Tripeptide Inhibitors of Angiotensin Converting Enzyme. Hiroshi Kayahara, Akio Ohashi, Koji Tadasa, Shozo Kato. Agricultural and Biological Chemistry. vol. 54(5), pp 1325–1326 (1990).*

Porter et al., "Photoregulation of Enzymes", Chapter 4, John Wiley & Sons, Inc., 1993, pp. 197–241.

Wani et al., "Plant Antitumor Agents. 18[1]. Synthesis and Biological Activity of Camptothecin Analogues", J. Med. Chem. 1989, vol. 23, pp. 554–560.

Sheehan et al., "A New Method of Forming Peptide Bonds", Communications to the Editor, vol. 77, Feb. 20, 1955, pp. 1067–1068.

Sheehan et al., "A Rapid Synthesis or Oligopeptide Derivatives without Isolation of Intermediates", Journal of the American Chemical Society, 87:11, Jun. 5, 1965, pp. 2492–2493.

(List continued on next page.)

Primary Examiner—Paul J. Killos
Assistant Examiner—Zachary C. Tucker
(74) Attorney, Agent, or Firm—Leydig, Voit, & Mayer, Ltd.

(57) ABSTRACT

The caged amino acid in accordance with the present invention has the structure represented by the following formula 1:

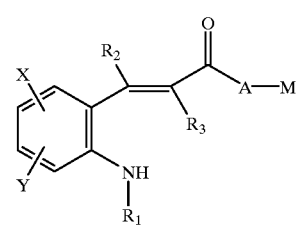

formula 1 where X and Y each represent a halogen atom, an alkyl group, an alkyloxy group, an alkylamino group, or a benzo group; $R_1$ represents a hydrogen atom or an alkyl group; $R_2$ and $R_3$ each represent a hydrogen atom or an alkyl group; A represents an amino acid residue; and M represents a hydrogen atom, an alkali metal, or an alkaline-earth metal.

2 Claims, 6 Drawing Sheets

Sheehan et al., "The Use of Water–Soluble and Basic Carbodimides in Peptide Synthesis", Contribution from the Department of Chemistry, Massachusetts Institute of Technology, vol. 21, Received Dec. 23, 1965, pp. 439–441.

Artico et al., "Heterocycles with a Benzothiadiazepine Moiety—1. Synthesis of Pyrrolo[1,2–b]–s–Triazolo[3,4–d] [1,2,5]Benzothiadiazepine 5,5,–Dioxide" Synthetic Communications, 22(10) (1992) pp. 1433–1439.

Sato et al., "Synthesis of 3–(2–Amino) Benxylidene–2, 5–Piperazinedione and its Conversion to 1–Azanaphthalenone and Spiro [Indo–Linepiperazine] Dione Derivatives" Heterocycles, vol. 33, No. 2, 1992, pp. 589–595.

Mack et al., "Synthesis of Some Novel 1,3–Dihydro–2H–benzimodazol–2–ylidenes", J. Org. Chem. vol. 58, No. 22, 1993, pp. 6158–6162.

Anderson et al., "N–Hydroxysuccinimide Esters in Peptide Synthesis", Communications to the Editor, Oct. 5, 1963, vol. 85, p. 3039.

Collman et al., "Hydrolytic Cleavage of N–Terminal Peptide Bonds by a Cobalt Chelate", Communications to the Editor, vol. 85, Oct. 5, 1963, pp. 3039–3040.

Dondoni et al., "Total Synthesis of (+)–Polyoxin J", J. Chem. Soc., Chem, Commun., 1995, pp. 2127–2128.

Renn et al., "Large–Scale Synthesis of the Bifunctional Chelating Agent 2–(p–Nitrobenzyl)–1,4,7,10–tetraazacyclododecane–N, N , N, N –tetraacetic Acid, and the Determination of its Enantiomeric Purity by Chiral Chromatography", Bioconjugate Chem., vol. 3, No. 6, 1992, pp. 563–569.

Sheradsky et al., "Intramolecular Oxidative Diels–Alder Reaction of N–Sorbyl–L–Proline Acylhydrazides", Tetrahedron Letters, vol. 32, No. 1, 1991, pp. 133–136.

Southwick et al., "The Amino Blocking Reagent—1–Isopropul–3–ethoxy–44–nitro–2–oxo–3–pyrroline and the N–Hydroxysuccinimide Esters of N–(1–Cyclohexyl– and 1–Isopropyl–4–nitro–2–oxo–3–pyrroline–3–yl)glycine", J. Org. Chem, vol. 49, 1984, pp. 1130–1134.

Takeda et al., "A Convenient Synthesis of Peptide Using Oxallates", Tetrahedron Letters, vol. 24, No. 41, 1983, pp. 4451–4454.

Billington et al., "The Synthesis of Novel Bifunctional Linker Molecules", Tetrahedron, vol. 47, No. 28, 1991, pp. 5231–5236.

Huang et al., "Acyclic Nucleic Acid Analogues: Synthesis and Oligomerization of Y,4–Diamino–2–oxo–1(2H)–pyrimidinepentanoic Acid and ∽, 4–Diamino–2–oxo–1 (2H)–pyrimidinehexanoic Acid", J. Org. Chem., vol. 56, No. 21, 1991, pp. 6007–6018.

Pfeiffer et al., "Aminolysis of Activated Esters of Indole–3–acetic Acid in Acetonitrile", J. Org. Chem., vol. 58, No. 3, 1993, pp. 735–740.

Cabaret et al., "an Efficient Synthesis of Aryl Phenaceturates Using Acid Ctalyzed Dicyclohexylcarbodiimide Esterification and Transient N–tert–Butoxycarbonylation", Synthesis, Short Papers, Received Oct. 8, 1993, pp. 480–482.

Barral et al., "Preparation of $N^x$–(2–Nitropenylthio)–$N^\epsilon$–acyl Lysine Derivatives", Synthesis, Communications, Dec. 1973, pp. 795–796.

Feldstein et al., "Acetyl Transfer during Hydrogenation of p–Nitrophenyl Acetate", Notes, vol. 26, Received Sep. 1, 1990, p. 1656.

Anderson et al., "t–Butyl Esters of Amino Acids and Peptides and their Use in Peptide Synthesis", The Organic Chemical Research Section, American Cyanamide Co., New York, vol. 82, Jul. 5, 1960, pp. 3359–3363.

Bodanszky et al., "An Improved Synthesis of Oxytocin", The Department of Biochemistry, Cornel Univ. Medical College, vol. 81, May 1959, pp. 2504–2507.

Anderson et al., "The Preparation of Secondary Benzylic Amines from Reactive Benzylic Tosylates", Communications, No. 9, Se. 1974, pp. 665–666.

Tsuji et al., "Studies on Anti–inflammatory Agents. IV. Synthesis and Pharmacological Properties of 1,5–Diarylpyrazoles and Related Derivatives", Chem. Pharm. Bull. 45(6) (1997) pp. 987–995.

Padmanabhan et al., "A Convenient One Pot Procedure for N–Methylation of Aromatic Amines using Trimethyl Orthoformate", Synthetic Communications, 27(4) (997), pp. 691–699.

Zhao et al., "A Concise Synthesis fo the Pyrroloquinoline Nucleus of the Makaluvamine Alkaloids", Synthetic Communications, 27(12) (1997), pp. 2103–2110.

Ramrao et al., "Phase Transfer Catalysed N–Monoalkylation of Amino Anthraquinones+", Synthetic Communications, 21(10&11) (1991), pp. 1129–1135.

* cited by examiner

CAGED AMINO ACIDS

BACKGROUND OF THE INVENTION

1. Field of the Invention

The present invention relates to new caged amino acids.

2. Related Background Art

For investigating the mechanism of action of a physiologically active amino acid compound such as glutamic acid in an organism, it is necessary to quantitatively measure the rise and fall of this compound within a biological system in a short period of time. Further, it is important to observe various changes following the compound introduced into the system.

On the other hand, biological reactions are mostly very fast, and a plurality of reactions usually progress at the same time while complicatedly relating to each other. Therefore, when the amino acid compound is added from the outside, the step of its diffusing within the system rather determines the rate, whereby the subsequent reaction to be determined in practice may not be grasped clearly.

SUMMARY OF THE INVENTION

For overcoming such a problem, various methods have been proposed as a method of rapidly adding an amino acid compound as a target material. As one of such methods, a method using a technique based on irradiation with light, i.e., so-called caged reagent, has been reported. In general, this method comprises the steps of introducing into a biological system a caged compound (which refers to a compound in which a caging group is introduced or a compound labeled with a caging group) in which a specific protective group protects an active part of a physiologically active substance to be traced; verifying that this substance has sufficiently diffused to a point of application; and then liberating the protective group (caging group) upon irradiation with light, so as to release the amino acid compound, thereby making it possible to trace the target reaction caused by the amino acid compound. This caged compound (caged amino acid) is characterized in that it can release the amino acid upon irradiation with light alone, it can release the protective group very fast, and it enables a position-specific supply of the amino acid by narrowing the light irradiation only to a specific part as necessary. The present invention provides amino acid compounds having functions mentioned above, which are caged by a caging group having a novel structure.

As a result of diligent studies, the inventor has succeeded in synthesizing caged amino acids having such excellent functions, thus accomplishing the present invention.

Namely, the caged amino acids in accordance with the present invention comprise, as a basic structure, an amide bond composed of an amino group of a target amino acid compound and a carboxyl group of a cinnamic acid derivative having a specific structure. Further, in the cinnamic acid derivative, each of its aromatic ring and carboxyl group is in a trans orientation with respect to its double bond. Also, the aromatic ring is characterized in that an amino group is disposed as a substitute at an ortho position with respect to the position where a double-bonded carbon is bound.

While the new caged amino acids in accordance with the is present invention stably exist in the dark, the amide bond is severed upon an intramolecular reaction in the presence of light, whereby the amino acid compound is released.

More specifically, a new caged amino acid in accordance with the present invention is a caged amino acid expressed by the following formula 1:

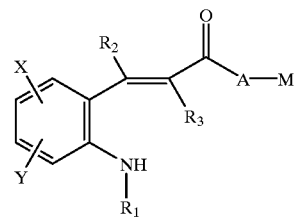

formula 1 where X and Y independently represent one kind selected from the group consisting of a hydrogen atom, a halogen atom, an alkyl group having a carbon number from 1 to 4, an alkyloxy group having a carbon number from 1 to 4, an alkylamino group having a carbon number from 1 to 4, and a benzo group, and may be identical or different from each other; $R_1$ represents one kind selected from the group consisting of a hydrogen atom and an alkyl group having a carbon number from 1 to 4; $R_2$ and $R_3$ independently represent one kind selected from the group consisting of a hydrogen atom and an alkyl group having a carbon number from 1 to 4, and may be identical or different from each other; A represents an amino acid residue selected from the group consisting of glycine, alanine, valine, leucine, isoleucine, serine, threonine, aspartic acid, glutamic acid, γ-aminobutanoic acid, N-methyl-D-aspartic acid, asparagine, glutamine, lysine, hydroxylysine, arginine, cysteine, cystine, methionine, phenylalanine, tyrosine, tryptophan, histidine, proline, and 4-hydroxyproline; and M represents one kind selected from the group consisting of a hydrogen atom, an alkali metal, and an alkaline-earth metal.

As preferable examples of new caged amino acids in accordance with the present invention, caged amino acids having respective structures expressed by the following formula 2 to 18 are specifically listed:

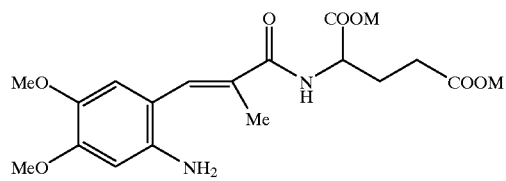

formula 2 where M represents one kind selected from the group consisting of a hydrogen atom, an alkali metal, and an alkaline-earth metal.

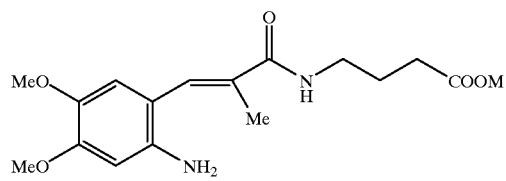

formula 3 where M represents one kind selected from the group consisting of a hydrogen atom, an alkali metal, and an alkaline-earth metal.

formula 4

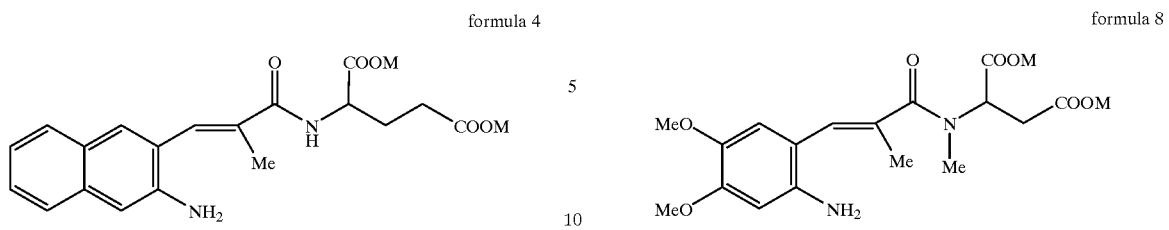

where M represents one kind selected from the group consisting of a hydrogen atom, an alkali metal, and an alkaline-earth metal.

formula 5

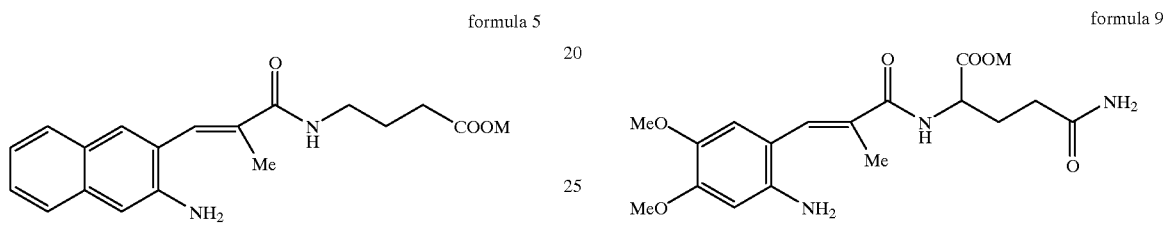

where M represents one kind selected from the group consisting of a hydrogen atom, an alkali metal, and an alkaline-earth metal.

formula 6

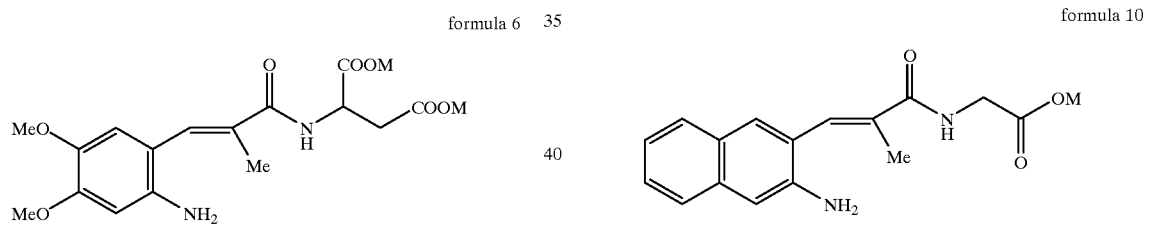

where M represents one kind selected from the group consisting of a hydrogen atom, an alkali metal, and an alkaline-earth metal.

formula 7

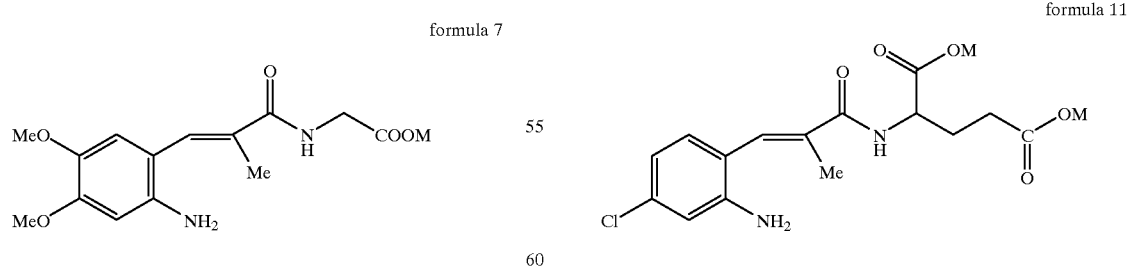

where M represents one kind selected from the group consisting of a hydrogen atom, an alkali metal, and an alkaline-earth metal.

formula 8 where M represents one kind selected from the group consisting of a hydrogen atom, an alkali metal, and an alkaline-earth metal.

formula 9 where M represents one kind selected from the group consisting of a hydrogen atom, an alkali metal, and an alkaline-earth metal.

formula 10 where M represents one kind selected from the group consisting of a hydrogen atom, an alkali metal, and an alkaline-earth metal.

formula 11 where M represents one kind selected from the group consisting of a hydrogen atom, an alkali metal, and an alkaline-earth metal.

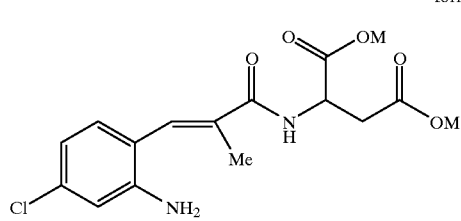

formula 12 where M represents one kind selected from the group consisting of a hydrogen atom, an alkali metal, and an alkaline-earth metal.

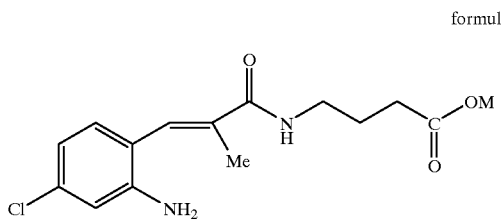

formula 13 where M represents one kind selected from the group consisting of a hydrogen atom, an alkali metal, and an alkaline-earth metal.

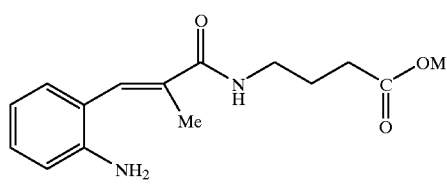

formula 14 where M represents one kind selected from the group consisting of a hydrogen atom, an alkali metal, and an alkaline-earth metal.

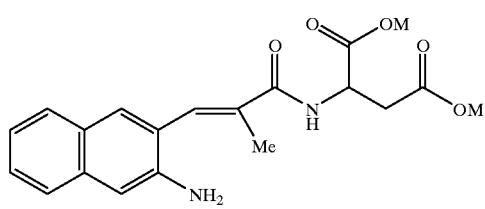

formula 15 where M represents one kind selected from the group consisting of a hydrogen atom, an alkali metal, and an alkaline-earth metal.

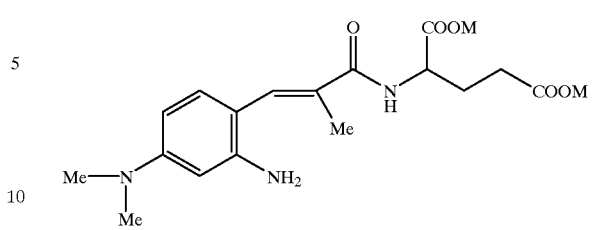

formula 16 where M represents one kind selected from the group consisting of a hydrogen atom, an alkali metal, and an alkaline-earth metal.

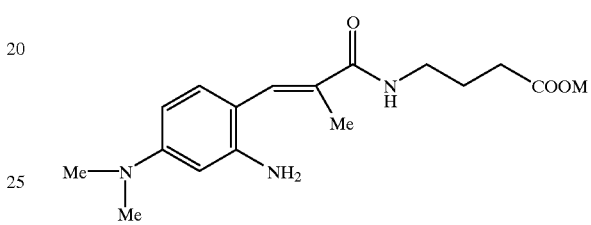

formula 17 where M represents one kind selected from the group consisting of a hydrogen atom, an alkali metal, and an alkaline-earth metal.

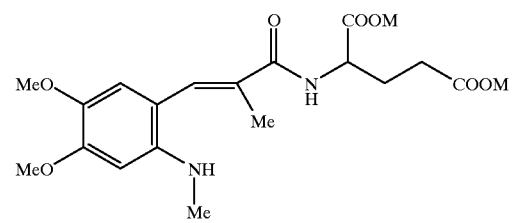

formula 18 where M represents one kind selected from the group consisting of a hydrogen atom, an alkali metal, and an alkaline-earth metal.

As shown in FIG. 1, while such a cage amino acid compound stably exists in the dark since the double bond of the cinnamate group is of a trans (E) structure, the double bond of the cinnamate group generates a cis (Z) structure upon irradiation with light due to a photoisomerization equilibrium. The resulting cis isomer is of a steric structure preferable for forming an intramolecular amide bond and rapidly releases an amino acid at the same time when a coumarin analogue (carbostyril) is generated.

BRIEF DESCRIPTION OF THE DRAWINGS

FIG. 2A shows a Wittig reaction; FIG. 2B shows a hydrolysis reaction; FIG.

2C shows a condensation reaction; FIG. 2D shows a reduction reaction; and FIG. 2E shows protective group liberating reaction;

FIG. 3A shows a Wittig reaction; FIG. 3B shows a hydrolysis reaction; FIG. 3C shows a condensation reaction; FIG. 3D shows a reduction reaction; FIG. 3E shows a coupling reaction; FIG. 3F shows another coupling reaction; and FIG. 3G shows a protective group liberating reaction;

FIG. 4A shows a Wittig reaction; FIG. 4B shows a reduction reaction; FIG. 4C shows a hydrolysis reaction; FIG. 4D shows a condensation reaction; FIG. 4E shows a coupling reaction; FIG. 4F shows another coupling reaction, and FIG. 4G shows a protective group liberating reaction:

In FIGS. 5A and 5B, tie Y-axis represents absorbance at 284 nm and the X-represents time in minutes. In FIGS. 5A and 5B, for example, "$1.210^6$" on the Y-axis stands for $1.2 \times 10^6$. In FIG. 5A, the peak at 4.8 min corresponds to the caged glutamic acid. In FIG. 5B, the peak at 8.5 min corresponds to carbostyril; In FIG. 6A, the Y-axis represents absorbance at 284 nm. In FIG. 6B, the Y-axis represents the intensity of fluorescence at 560 nm. In FIGS. 6A and 6B, the Y-axis values are abbreviated. For example, in FIG. 6A, "$1.510^5$" stands for $1.5 \times 10^5$. In FIGS. 6A and 6B, the X-axis represents time in minutes. In FIG. 6B, the peak at 7.2 min corresponds to dansyl glutamic acid.

DESCRIPTION OF THE PREFERRED EMBODIMENTS

In the following, the present invention will be explained further in detail.

Synthesizing Method

The method of synthesizing caged amino acids in accordance with the present invention is not restricted in particular, and known organic chemistry reactions are favorably usable in general. As specific examples of the method favorably usable in the present invention, three synthesizing routes illustrated in FIGS. 2A to 2E, 3A to 3G, and 4A to 4G will be mentioned. These methods can synthesize caged amino acids having various substituents in accordance with the present invention easily with a favorable yield and a high purity.

Figure 2A:
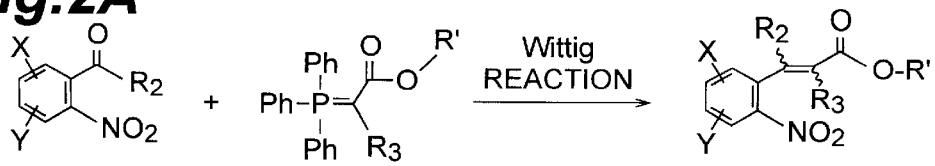
FIGS. 2A to 2E are reaction flowcharts showing an example of synthesizing routes of the caged amino acid in accordance with the present invention.

The synthesizing route shown in FIGS. 2A to 2E includes a step of forming a cinnamate skeleton upon a reaction between a 2-nitrobenzaldehyde derivative (including a phenylketone derivative) having a favorable substituent and Wittig reagent (including Wadsworth-Emmons reagent) for introducing the favorable substituent (FIG. 2A). For the 2-nitrobenzaldehyde derivative (including a phenylketone derivative) and Wittig reagent (including Wadsworth-Emmons reagent), which are necessary starting materials, commercially available products can be used. Also, they can be synthesized by conventionally known organic synthesizing methods (Organic Synthesis, col. vol. 3, 641.; Organic Synthesis, col. vol. 4, 735; Organic Synthesis, col. vol. 5, 825; Kienzle, Frank, Helv. Chim. Acta, 63 (8), 2364–2369 (1980); and Wani, Mansukh C., Ronman, Peter E., Lindley, James T., and Wall, Monroe E., J. Med. Chem. 1980, 23, 554–560). The reaction condition of Wittig reaction is not restricted in particular, and known conditions are usable in general (Organic Reaction, vol. 14, p. 270–423 (1965); and Organic Reaction, vol. 25, 73 (1977)). It is easy for those skilled in the art to select and optimize a favorable reaction condition in view of such literatures and the like.

Here, the resulting cinnamate derivative may be any of cis form and trans form with respect to the double bond, and may be a mixture thereof. Means for verifying its structure is not restricted in particular, and known means for analyzing organic compounds are usable in general. Specifically, such means as infrared absorption spectrum (IR), nuclear magnetic resonance spectrum, mass spectrum, and the like can verify the existence of double bond, ester group, and nitro group. Also, various known or commercially available liquid chromatographs, gas chromatographs, and the like can be used for determining the yield and purity of the product.

Figure 2B:
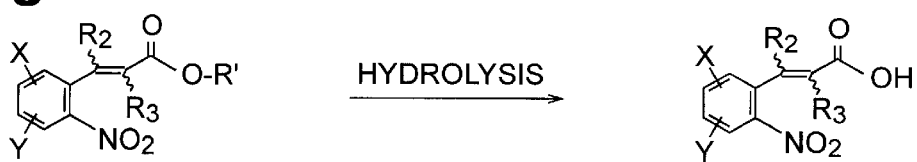

Further, the synthesis shown in FIGS. 2A to 2E includes a reaction of hydrolyzing an ester into a carboxylic acid (FIG. 2B). The method of reaction for hydrolyzing such an ester (which is a methyl or ethyl ester in general) is not restricted in particular either, and known methods (T. W. Greene and P. G. M. Wuts, "Protective Group in Organic Synthesis," 2nd ed., p. 224–251, John Wiley & Sons (1991)) can favorably be used in general. A specific example thereof is a reaction under an acidic or alkaline condition. The reaction condition of such a hydrolyzing reaction is not restricted in particular, and known conditions are usable in general. It is easy for those skilled in the art to select and optimize a favorable reaction condition in view of such a literature.

Here, the resulting cinnamate derivative may be any of cis form and trans form with respect to the double bond, and may be a mixture thereof. Means for verifying its structure is not restricted in particular, and known means for analyzing organic compounds are usable in general. Specifically, such means as infrared absorption spectrum (IR), nuclear magnetic resonance spectrum, mass spectrum, and the like can verify the existence of double bond, carboxyl group, and nitro group. Also, various known or commercially available liquid chromatographs, gas chromatographs, and the like can be used for determining the yield and purity of the product.

Figure 2C:
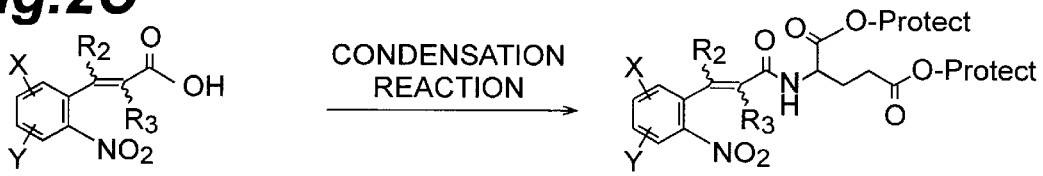

Further, the synthesis shown in FIGS. 2A to 2E includes a reaction by which the resulting acid derivative and an amino acid derivative to become the caged compound are dehydrated and condensed so as to form an amide compound (FIG. 2C). Here, as the amino acid derivative to be dehydrated and condensed with the cinnamic acid derivative, a carboxyl-protected amino acid derivative (e.g., di-t-butyl glutamate) in which a carboxyl group (also including one or two carboxyl groups on an amino acid side chain if any) within the molecule thereof is esterified by an alcohol having an alkyl group with a carbon number from 1 to 4 is used. Commercially available products can be used as such a carboxyl-protected amino acid derivative, and it can be synthesized by a conventionally know organic synthesizing reaction as well (T. W. Greene and P. G. M. Wuts, "Protective Group in Organic Synthesis," 2nd ed., p. 224–251, John Wiley & Sons (1991)).

The method of dehydration and condensation reaction between the cinnamic acid derivative and the amino acid derivative is not restricted in particular, and known methods can favorably be used. Preferably, various dehydrators are used in a polar nonaqueous solvent (e.g., dimethylformaldehyde, tetrahydrofuran, 1,4-dioxane, or dichloromethane). Specific examples of dehydrators include dicyclohexylcarbodiimide (DCC), 1-ethyl-3-(3-dimethylaminopropyl)-carbodiimide (EDC), and 1-ethyl-3-(3-dimethylaminopropyl)-carbodiimide hydrochloride (EDC-HCl). The reaction condition of such dehydration and condensation is not restricted in particular, and known conditions are usable in general (J. C. Sheehan and G. P. Hess, J. Am. Chem. Soc., 77, 1067 (1955); J. C. Sheehan, J. Preston, and P. A. Cruikshank, J. Am. Chem. Soc., 87, 2492 (1965); and J. C. Sheehan and J. J. Hlavka, J. Org. Chem., 21, 439 (1956)). It is easy for those skilled in the art to select and optimize a favorable reaction condition in view of such literatures.

Means for verifying the structure is not restricted in particular, and known means for analyzing organic compounds are usable in general. Specifically, such means as infrared absorption spectrum (IR), nuclear magnetic resonance spectrum, mass spectrum, and the like can verify the existence of double bond, amide group, ester group, and aromatic nitro group. Also, various known or commercially available liquid chromatographs, gas chromatographs, and the like can be used for determining the yield and purity of the product.

Figure 2D:
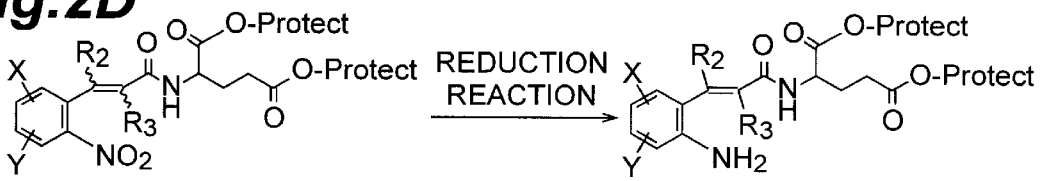

Further, the synthesis shown in FIGS. 2A to 2E includes a reaction by which the aromatic nitro group is reduced to the amino group (FIG. 2D). The method of this reaction for reducing the nitro group to the amino group is not restricted in particular, and various known methods can favorably be used (Marino Articoa, Romano Silvestri, and Giorgio Stefancich, Synthesis Comm., 22 (10), 1433–1439 (1992); Yoshiaki Sato, Yoshiharu Nakajima, and Chung-gi Shin, Heterocycles, 33 (2), 589–595 (1992); RobertA. Mack, Vassil St. Georgiev, Edwin S. C. Wu, and James R. Matz, J. Org. Chem., 58, 6158–6162 (1993); and Pierre Martin and Tammo Winkler, Helvetica Chemica Acta, 17, 111–120 (1994)). A specific example thereof is a reduction reaction with a metal under an acidic condition. A more specific example is a method using iron (including iron powder) under an acidic condition of acetic acid. The condition of such an acetic acid/iron reduction reaction is not restricted in particular, and known conditions are usable in general. It is easy for those skilled in the art to select and optimize a favorable reaction condition in view of such literatures.

The aromatic amino derivative obtained here is in a trans form with respect to the double bond. It is because of the fact that, while a cis product is also generated upon the above-mentioned reduction reaction, a nitrogen-substituted coumarin derivative (carbostyril derivative) is easily formed according to a mechanism similar to the photoreaction shown in FIG. 1.

Means for verifying the structure is not restricted in particular, and known means for analyzing organic compounds are usable in general. Specifically, such means as infrared absorption spectrum (IR), nuclear magnetic resonance spectrum, mass spectrum, and the like can verify the existence of trans double bond, amide group, ester group, and aromatic amino group. Also, various known or commercially available liquid chromatographs, gas chromatographs, and the like can be used for determining the yield and purity of the product.

Figure 2E:
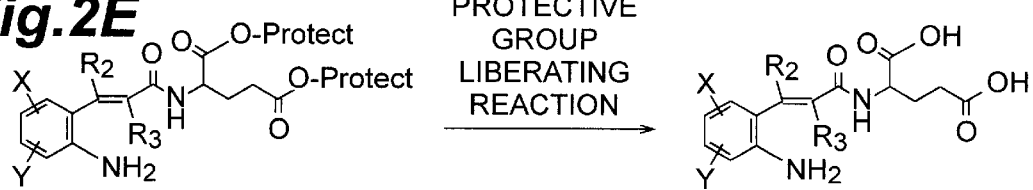

Further, the synthesis shown in FIGS. 2A to 2E includes a reaction by which the protective groups are released upon hydrolysis of the ester groups in the amino acid portion, so as to yield carboxylic acid, thereby synthesizing the caged amino acid of the present invention (FIG. 2E). The method of reaction for hydrolyzing such an ester (which is usually an alkyl ester having a carbon number from 1 to 4) is not restricted in particular, and known methods can favorably be used in general. Specific examples thereof include reactions under an acidic or alkaline condition. The reaction condition for such a hydrolyzing reaction is not restricted in particular, and known conditions are usable in general (T. W. Greene and P. G. M. Wuts, "Protective Group in Organic Synthesis," 2nd ed., p. 224–251, John Wiley & Sons (1991)). It is easy for those skilled in the art to select and optimize a favorable reaction condition in view of such a literature.

The cinnamate acid derivative obtained here is in a trans form with respect to the double bond. It is because of the fact that, while a cis product is also generated upon the above-mentioned reduction reaction, a nitrogen-substituted coumarin derivative is easily formed according to a mechanism similar to the photoreaction shown in FIG. 1.

Means for verifying the structure is not restricted in particular, and known means for analyzing organic compounds are usable in general. Specifically, such means as infrared absorption spectrum (IR), nuclear magnetic resonance spectrum, mass spectrum, and the like can verify the existence of trans double bond, amide group, carboxylic acid, and aromatic amino group. Also, various known or commercially available liquid chromatographs, gas chromatographs, and the like can be used for determining the yield and purity of the product.

Figure 3A:
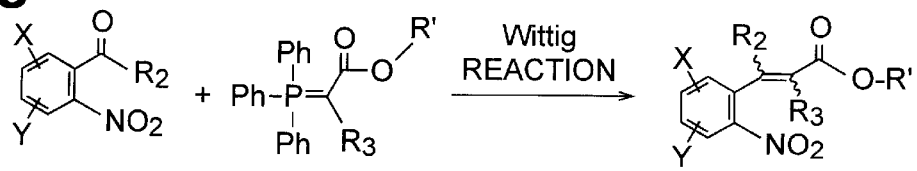
FIGS. 3A to 3G are reaction flowcharts showing another example of synthesizing routes of the caged amino acid in accordance with the present invention.
Figure 3B:
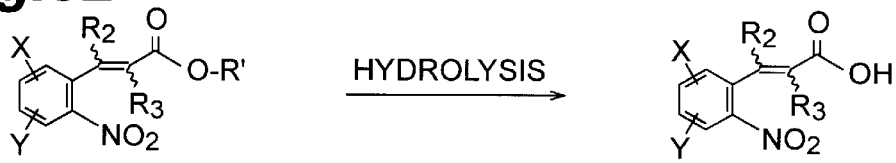

Another synthesizing route is a synthesizing method in which N-succinimide ester is formed in an intermediate step in the above-mentioned synthesis as shown in FIGS. 3A to 3G. As in FIGS. 2A and 2B, the synthesis shown in FIGS. 3A to 3G includes Wittig reaction for forming a cinnamate ester derivative, and a reaction of hydrolyzing it to form an acid derivative (FIGS. 3A and 3B).

Figure 3C:
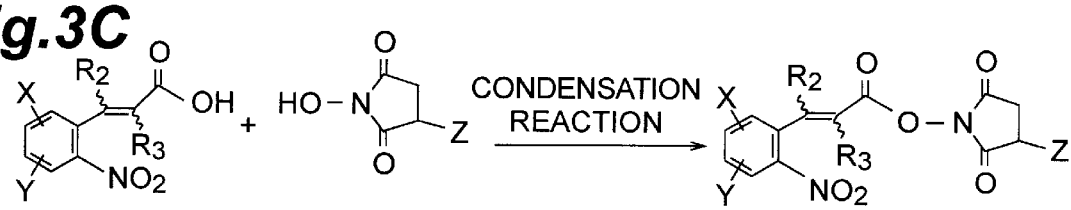

Further, FIGS. 3A to 3G include a reaction by which thus obtained acid derivative and N-hydroxysuccinimide (including its derivative having a sulfonic acid group) are dehydrated and condensed so as to yield N-succinimidyl cinnamate (FIG. 3C). The method of this dehydration and condensation reaction is not restricted in particular, and known methods (G. W. Anderson, J. E. Zimmerman, and F. Callahan, J. Am. Chem. Soc., 85, 3039 (1963)) can favorably be used. Preferably, various dehydrators are used in a polar nonaqueous solvent (e.g., dimethylformaldehyde, tetrahydrofuran, 1,4-dioxane, or dichloromethane). Specific examples of dehydrators include dicyclohexylcarbodiimide (DCC), 1-ethyl-3-(3-dimethylaminopropyl)-carbodiimide (EDC), and 1-ethyl-3-(3-dimethylaminopropyl)-carbodiimide hydrochloride (EDC-HCl). The reaction condition of such dehydration and condensation is not restricted in particular, and known conditions are usable in general. It is easy for those skilled in the art to select and optimize a favorable reaction condition in view of such a literature.

The cinnamate derivative having N-succinimidyl ester group obtained here may be any of cis form and trans form with respect to the double bond, and may be a mixture thereof. Means for verifying its structure is not restricted in particular, and known means for analyzing organic compounds are usable in general. Specifically, such means as infrared absorption spectrum (IR), nuclear magnetic resonance spectrum, mass spectrum, and the like can verify the existence of double bond, nitro group, and N-succinimidyl group. Also, various known or commercially available liquid chromatographs, gas chromatographs, and the like can be used for determining the yield and purity of the product.

Figure 3D:

Further, the synthesis shown in FIGS. 3A to 3G includes a reaction by which the aromatic nitro group is reduced to the amino group (FIG. 3D). The method of this reaction for reducing the nitro group to the amino group is not restricted in particular, and various known methods mentioned in the foregoing explanation of FIG. 2D can favorably be used. A specific example thereof is a reduction reaction under an acidic condition or, more specifically, a method using iron (including iron powder) under an acidic condition of acetic acid. The condition of such an acetic acid/iron reduction reaction is not restricted in particular, and known conditions are usable in general. It is easy for those skilled in the art to select and optimize a favorable reaction condition in view of a literature.

The amino derivative obtained here is in a trans form with respect to the double bond. It is because of the fact that, while a cis product is also generated upon the above-mentioned reduction reaction, a nitrogen-substituted coumarin derivative is easily formed according to a mechanism similar to the photoreaction shown in FIG. 1.

Means for verifying the structure is not restricted in particular, and known means for analyzing organic compounds are usable in general. Specifically, such means as infrared absorption spectrum (IR), nuclear magnetic resonance spectrum, mass spectrum, and the like can verify the existence of trans double bond, ester group, and aromatic amino group. Also, various known or commercially available liquid chromatographs, gas chromatographs, and the like can be used for determining the yield and purity of the product.

Figure 3E:
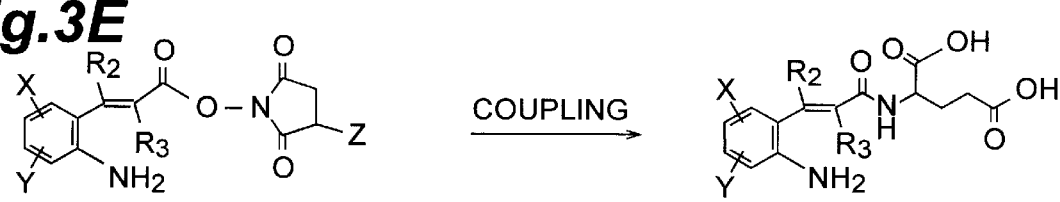

Further, the synthesis shown in FIGS. 3A to 3G includes a reaction by which an amino acid to become a caged compound and the above-mentioned N-succinimide ester are reacted so as to synthesize the caged amino acid of the present invention (FIG. 3E). The method of such a coupling reaction between the N-succinimide ester and the amino acid is not restricted in particular, and known methods (Dondoni, A., Junquera, F., Merchan, F. L., Merino, P., and Tejero, T., J. Chem. Soc., Chem. Commun. (1995) 20, 2127–2128; Renn, O. and Meares, C. F. , Bioconjugate Chem. 3 (1992) 6, 563–569.; Sheradsky, T., Milvitskaya, J., and Pollak, I., Tetrahedron Lett. 32 (1991) 1, 133–136; P. L. Southwick, G. K. Chin, M. A. Koshute, J. R. Miller, K. E. Niemela, C. A. Soege, R. T. Nolte, and W. E. Brown, J. Org. Chem., 49 (6), 1130 (1984); and Kazuyoshi Takeda, Izumi Sawada, Akira Suzuki, and Haruo Ogura, Tetrahedron. Lett., 24 , 4451 (1983)) can favorably be used in general. Preferably, the reaction can be carried out in water or in a polar nonaqueous solution (e.g., dimethylformaldehyde, tetrahydrofuran, 1,4-dioxane, dichloromethane, or a mixture thereof). If the reaction is wanted to progress faster, an alkaline compound such as triethylamine, sodium hydroxide, sodium hydrogencarbon ate, or the like can also be added thereto. It is easy for those skilled in the art to select and optimize a favorable reaction condition in view of such literatures.

The amino acid derivative obtained here is in a trans form with respect to the double bond. It is because of the fact that, while a cis product is also generated upon the above-mentioned reduction reaction, a nitrogen-substituted coumarin derivative is easily formed according to a mechanism similar to the photoreaction shown in FIG. 1.

Means for verifying the structure is not restricted in particular, and known means for analyzing organic compounds are usable in general. Specifically, such means as infrared absorption spectrum (IR), nuclear magnetic resonance spectrum, mass spectrum, and the like can verify the existence of trans double bond, N-succinimide group, and aromatic amino group. Also, various known or commercially available liquid chromatographs, gas chromatographs, and the like can be used for determining the yield and purity of the product.

Figure 3F:
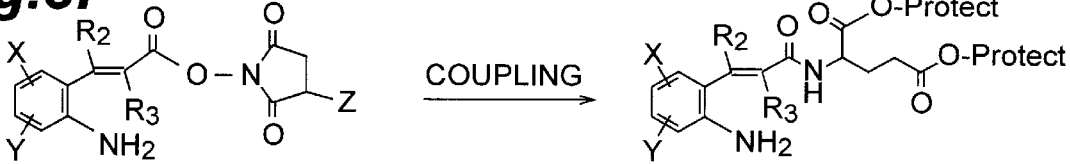

Further, the synthesis shown in FIGS. 3A to 3G includes a reaction between thus obtained N-succinimide ester and a carboxyl-ester-protected derivative of an amino acid to become a caged compound (FIG. 3F). The method of such a coupling reaction between the N-succinimide ester and the amino acid derivative is not restricted in particular, and known methods can favorably be used in general. Preferably, the reaction can be carried out in water or in a polar nonaqueous solution (e.g., dimethylformaldehyde, tetrahydrofuran, 1,4-dioxane, dichloromethane, or a mixture thereof). If the reaction is wanted to progress faster, an alkaline compound such as triethylamine, sodium hydroxide, sodium hydrogencarbon ate, or the like can also be added thereto.

The amino acid derivative obtained here is in a trans form with respect to the double bond. It is because of the fact that, while a cis product is also generated upon the above-mentioned reduction reaction, a nitrogen-substituted coumarin derivative is easily formed according to a mechanism similar to the photoreaction shown in FIG. 1.

Means for verifying the structure is not restricted in particular, and known means for analyzing organic compounds are usable in general. Specifically, such means as infrared absorption spectrum (IR), nuclear magnetic resonance spectrum, mass spectrum, and the like can verify the existence of trans double bond, amide group, and aromatic amino group. Also, various known or commercially available liquid chromatographs, gas chromatographs, and the like can be used for determining the yield and purity of the product.

Figure 3G:
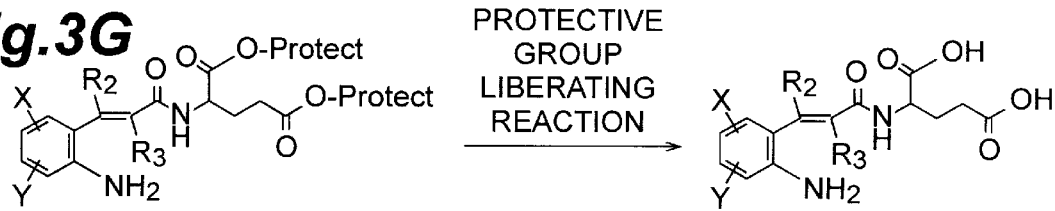

Further, the synthesis shown in FIGS. 3A to 3G includes a reaction by which the ester groups in the carboxyl group of the amino acid portion are hydrolyzed so as to yield carboxylic acid, thereby synthesizing the caged amino acid of the present invention (FIG. 3G). The method of reaction for hydrolyzing such an ester (which is usually an alkyl ester having a carbon number from 1 to 4) is not restricted in particular, and known methods can favorably be used in general. Specific examples thereof include reactions under an acidic or alkaline condition. The reaction condition for such a hydrolyzing reaction is not restricted in particular, and known conditions are usable in general (T. W. Greene and P. G. M. Wuts, "Protective Group in Organic Synthesis," 2nd ed., p. 224–251, John Wiley & Sons (1991)). It is easy for those skilled in the art to select and optimize a favorable reaction condition in view of such a literature.

The amino acid derivative obtained here is in a trans form with respect to the double bond. It is because of the fact that, while a cis product is also generated upon the above-mentioned reduction reaction, a nitrogen-substituted coumarin derivative is easily formed according to a mechanism similar to the photoreaction shown in FIG. 1.

Means for verifying the structure is not restricted in particular, and known means for analyzing organic compounds are usable in general. Specifically, such means as infrared absorption spectrum (IR), nuclear magnetic resonance spectrum, mass spectrum, and the like can verify the existence of trans double bond, amide group, carboxyl group, and aromatic amino group. Also, various known or commercially available liquid chromatographs, gas chromatographs, and the like can be used for determining the yield and purity of the product.

Another synthesizing route is a synthesizing method in which p-nitrophenol ester is formed in an intermediate step in the above-mentioned synthesis as shown in FIGS. 4A to 4G.

Figure 4A:
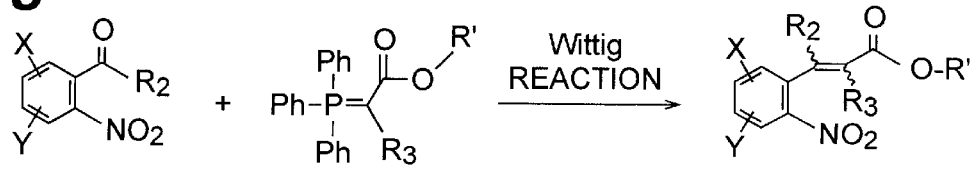
FIGS. 4A to 4G are reaction flowcharts showing yet another example of synthesizing routes of the caged amino acid in accordance with the present invention.

As in FIGS. 2A and 3A, the synthesis shown in FIGS. 4A to 4G includes Wittig reaction for forming a cinnamate derivative (FIG. 4A).

Figure 4B:
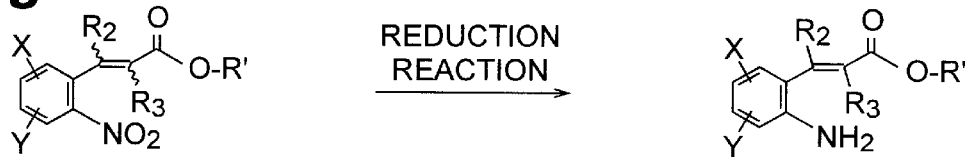

Further, the synthesis shown in FIGS. 4A to 4G includes a reaction by which the aromatic nitro group is reduced to the amino group (FIG. 4B). The method of this reaction for reducing the nitro group to the amino group is not restricted in particular, and various known methods mentioned in the foregoing explanation of FIGS. 2D and 3D can favorably be used. A specific example thereof is a reduction reaction under an acidic condition. A more specific example is a method using iron (including iron powder) under an acidic condition of acetic acid. The condition of such an acetic acid/iron reduction reaction is not restricted in particular, and known conditions are usable in general. It is easy for those skilled in the art to select and optimize a favorable reaction condition in view of a literature.

The amino derivative obtained here is in a trans form with respect to the double bond. It is because of the fact that, while a cis product is also generated upon the above-mentioned reduction reaction, a nitrogen-substituted coumarin derivative is easily formed according to a mechanism similar to the photoreaction shown in FIG. 1.

Means for verifying the structure is not restricted in particular, and known means for analyzing organic compounds are usable in general. Specifically, such means as infrared absorption spectrum (IR), nuclear magnetic resonance spectrum, mass spectrum, and the like can verify the existence of trans double bond, ester group, and aromatic amino group. Also, various known or commercially available liquid chromatographs, gas chromatographs, and the like can be used for determining the yield and purity of the product.

Figure 4C:
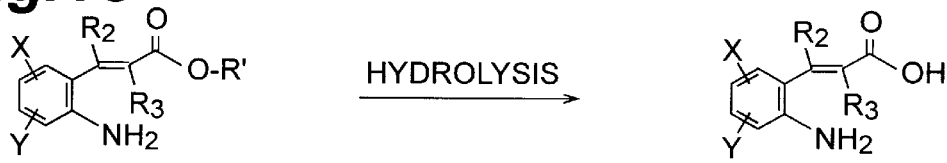

Further, the synthesis shown in FIGS. 4A to 4G includes a reaction of hydrolyzing an ester group into a carboxylic acid (FIG. 4C). The method of reaction for hydrolyzing such an ester (which is a methyl or ethyl ester in general) is not restricted in particular, and known methods can favorably be used in general. A specific example thereof is a reaction under an acidic or alkaline condition. The reaction condition of such a hydrolyzing reaction is not restricted in particular, and known conditions are usable in general. It is easy for those skilled in the art to select and optimize a favorable reaction condition in view of a literature. Means for verifying the structure is not restricted in particular, and known means for analyzing organic compounds are usable in general. Specifically, such means as infrared absorption spectrum (IR), nuclear magnetic resonance spectrum, mass spectrum, and the like can verify the existence of trans double bond, carboxylic acid, and aromatic amino group. Also, various known or commercially available liquid chromatographs, gas chromatographs, and the like can be used for determining the yield and purity of the product.

Figure 4D:
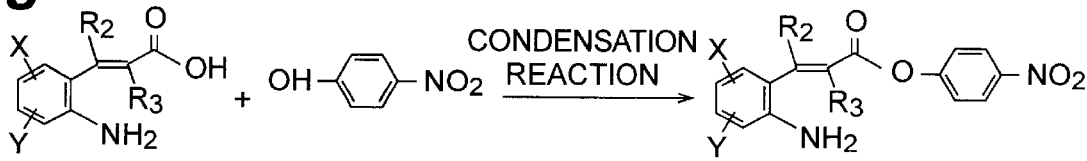

Further, the synthesis shown in FIGS. 4A to 4G includes a reaction by which thus obtained acid derivative and p-nitrophenol are dehydrated and condensed, so as to yield p-nitropheyl aminocinnamate (FIG. 4D). The method of such a dehydration and condensation reaction is not restricted in particular, and known methods (Billington, S., Mann, J., Quazi, P., Alexander, R., Eaton, M. A. W., Millar, K., and Millican, A., Tetrahedron 47 (1991) 28, 5231–5236; Huang, S.-B., Nelson, J. S., and Weller, D. D., J. Org. Chem. 56 (1991) 21, 6007–6018; Pfeiffer, M. J. and Hanna, S. B., J. Org. Chem. 58 (1993) 3, 735–740; and Cabaret, D., Liu, J., and Wakselman, M., Synthesis (1994) 5, 480–482) can favorably be used in general. Preferably, various dehydrators are used in a polar nonaqueous solvent (e.g., dimethylformaldehyde, tetrahydrofuran, 1,4-dioxane, or dichloromethane). Specific examples of dehydrators include dicyclohexylcarbodiimide (DCC), 1-ethyl-3-(3-dimethylaminopropyl)-carbodiimide (EDC), and 1-ethyl-3-(3-dimethylaminopropyl)-carbodiimide hydrochloride (EDC-HCl). The reaction condition of such dehydration and condensation is not restricted in particular, and known conditions are usable in general. It is easy for those skilled in the art to select and optimize a favorable reaction condition in view of such literatures.

Means for verifying the structure is not restricted in particular, and known means for analyzing organic compounds are usable in general. Specifically, such means as infrared absorption spectrum (IR), nuclear magnetic resonance spectrum, mass spectrum, and the like can verify the existence of trans double bond, ester group, aromatic amino group, and aromatic nitro group. Also, various known or commercially available liquid chromatographs, gas chromatographs, and the like can be used for determining the yield and purity of the product.

Figure 4E:

Further, the synthesis shown in FIGS. 4A to 4G includes a reaction by which the caged amino acid of the present invention is synthesized from thus obtained p-nitrophenyl ester and an amino acid to become a caged compound (FIG. 4E). The method of such a coupling reaction between the p-nitrophenyl ester and the amino acid is not restricted in particular, and known methods (I. Barral et al., Synthesis, p. 795 (1973); R. Feldstein et al., J. Org. Chem., 26, 1656 (1961); G. W. Anderson et al., J. Am. Chem. Soc., 82, 3359 (1960); and M. Bodansky et al., J. Am. Che. Soc., 821, 2504 (1959)) can favorably be used. Preferably, the reaction is carried out in water or in a polar nonaqueous solution (e.g., dimethylformaldehyde, tetrahydrofuran, 1,4-dioxane, dichloromethane, or a mixture thereof). If the reaction is wanted to progress faster, an alkaline compound such as triethylamine, sodium hydroxide, sodium hydrogencarbonate, or the like can also be added thereto. It is easy for those skilled in the art to select and optimize a favorable reaction condition in view of such literatures.

The amino derivative obtained here is in a trans form with respect to the double bond. It is because of the fact that, while a cis product is also generated upon the above-mentioned reduction reaction, a nitrogen-substituted coumarin derivative is easily formed according to a mechanism similar to the photoreaction shown in FIG. 1.

Means for verifying the structure is not restricted in particular, and known means for analyzing organic compounds are usable in general. Specifically, such means as infrared absorption spectrum (IR), nuclear magnetic resonance spectrum, mass spectrum, and the like can verify the existence of trans double bond, aromatic nitro group, and aromatic amino group. Also, various known or commercially available liquid chromatographs, gas chromatographs, and the like can be used for determining the yield and purity of the product.

Figure 4F:
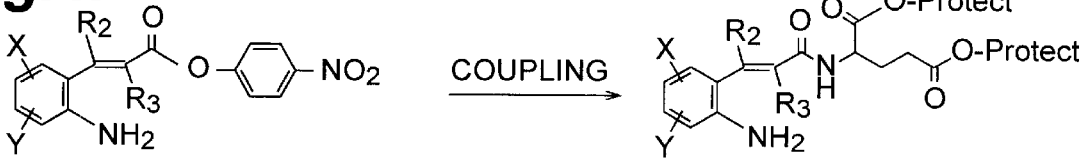

Further, the synthesis shown in FIGS. 4A to 4G includes a reaction between thus obtained p-nitrophenyl ester and a carboxyl-ester-protected derivative of an amino acid to become a caged compound (FIG. 4F). The method of such a coupling reaction between the p-nitrophenyl ester and the amino acid derivative is not restricted in particular, and known methods can favorably be used. Preferably, the reaction is carried out in water or in a polar nonaqueous solution (e.g., dimethylformaldehyde, tetrahydrofuran, 1,4-dioxane, dichloromethane, ethyl acetate, or a mixture thereof). If the reaction is wanted to progress faster, an alkaline compound such as triethylamine, sodium hydroxide, sodium hydrogencarbon ate, or the like can also be added thereto.

The amino acid derivative obtained here is in a trans form with respect to the double bond. It is because of the fact that, while a cis product is also generated upon the above-mentioned reduction reaction, a nitrogen-substituted coumarin derivative is easily formed according to a mechanism similar to the photoreaction shown in FIG. 1.

Means for verifying the structure is not restricted in particular, and known means for analyzing organic compounds are usable in general. Specifically, such means as infrared absorption spectrum (IR), nuclear magnetic resonance spectrum, mass spectrum, and the like can verify the existence of trans double bond, amide group, and aromatic amino group. Also, various known or commercially available liquid chromatographs, gas chromatographs, and the like can be used for determining the yield and purity of the product.

Figure 4G:
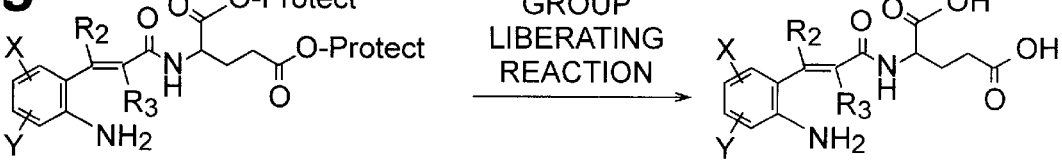

Further, the synthesis shown in FIGS. 4A to 4G includes a reaction by which the ester groups in the carboxyl group of the amino acid portion are hydrolyzed so as to yield carboxylic acid, thereby synthesizing the caged amino acid of the present invention (FIG. 4G). The method of reaction for hydrolyzing such an ester (which is usually an alkyl ester having a carbon number from 1 to 4) is not restricted in particular, and known methods can favorably be used in general. Specific examples thereof include reactions under anacidicor alkaline condition. The reaction condition for such a hydrolyzing reaction is not restricted in particular, and known conditions are usable in general (T. W. Greene and P. G. M. Wuts, "Protective Group in Organic Synthesis," 2nd ed., p. 224–251, John Wiley & Sons (1991)). It is easy for those skilled in the art to select and optimize a favorable reaction condition in view of such a literature.

The amino acid derivative obtained here is in a trans form with respect to the double bond. It is because of the fact that, while a cis product is also generated upon the above-mentioned reduction reaction, a nitrogen-substituted coumarin derivative is easily formed according to a mechanism similar to the photoreaction shown in FIG. 1.

Means for verifying the structure is not restricted in particular, and known means for analyzing organic compounds are usable in general. Specifically, such means as infrared absorption spectrum (IR), nuclear magnetic resonance spectrum, mass spectrum, and the like can verify the existence of trans double bond, amide group, carboxyl group, and aromatic amino group. Also, various known or commercially available liquid chromatographs, gas chromatographs, and the like can be used for determining the yield and purity of the product.

While the aimed caged amino acid can be obtained with a high yield and a high selectivity by the above-mentioned synthesizing routes of FIGS. 2A to 2E, 3A to 3G, and 4A to 4G, it can be obtained with a higher yield and a higher selectivity when a protective group is introduced to the amino group of the intermediate product obtained in each of the reactions shown in FIGS. 3D, 4C, and 4D so as to suppress side reactions. Here, tert-butyloxycarbonyl group, trimethylsilylethoxycarbonyl group, benzyloxycarbonyl group, and the like can specifically be noted as preferable examples of protective group introduced to the amino group. The forming of protective group at the amino group is particularly effective when the aimed amino acid is a secondary amine. The reaction of liberating the protective group can be carried out easily. For example, in the case of trimethylsilylethoxycarbonyl group, it can easily be released by use of trifluoroacetic acid (TFA) in a post-processing step of the coupling reaction.

Photoreaction of New Caged Amino Acid

Figure 1:
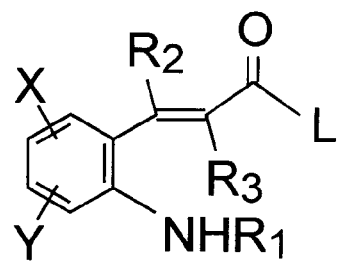
FIG. 1 is a reaction flowchart showing that a coumarin analogue (carbostyril) and an amino acid are released when a caged amino acid of the present invention is irradiated with light; L represents an amino acid.
Figure 1:
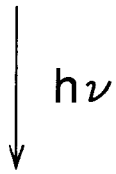
Figure 1:
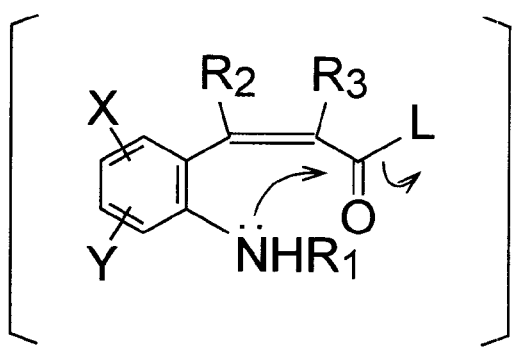
Figure 1:
Figure 1:
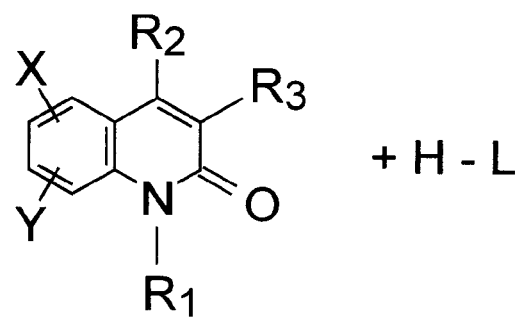

When the new caged amino acid in accordance with the present invention is irradiated with light, a cleavage occurs in the amide bond between the caging functional group having an amino cinnamate structure and the amino group of the amino acid as shown in FIG. 1, whereby the amino acid and the N-substituted coumarin derivative can be generated easily. Also, by use of a microscope or the like, amino acids can be generated at a specific position of a tissue alone, and light irradiation can be adjusted in order to partly release amino acids.

Stability of New Caged Amino Acid

Since the bonding between the functional group having a cinnamate structure adapted to cause a photoreaction and the amino acid is formed by a very firm amide bond, the caged amino acid in accordance with the present invention exhibits a very high stability in the dark.

The present invention will now be explained in further detail with reference to Examples, which do not limit the present invention at all.

EXAMPLES

Though methods of synthesizing new caged amino acids concerned with glutamic acid, γ-aminobutanoic acid (GABA), aspartic acid, N-methyl-D-aspartic acid, glycine, and glutamine are described in detail in the following, all the caged amino acids and caged amino acid analogues in accordance with the present invention can be synthesized by using 2-nitronbenzaldehyde derivatives (including phenylketone derivatives) in which various functional groups are introduced and Wittig reagent (including Wadsworth-Emmons reagent) or by using various amino acids, amino acid analogues, and their carboxyl-protected products.

Synthesis of 3-(4,5-dimethoxy-2-nitrophenyl)-2-methyl-2-propenoic acid ethyl ester In a dark room, 10 g (50.0 mmol) of 6-nitroveratlaldehyde (manufactured by Aldrich Chemical Co., Inc.) and 18.1 g (50.0 mmol) of Wittig reagent (carbethoxyethylidene triphenylphosphorane, manufactured by Aldrich Chemical Co., Inc.) were stirred in benzene for 18 hours at room temperature so as to be reacted. After the completion of the reaction, benzene was eliminated under a reduced pressure, whereby a white crystal was obtained. Thus obtained crystal was recrystallized from ethyl acetate, whereby 28.5 g of the aimed compound were obtained (yield: 76%).

The structure of this compound was verified by infrared absorption spectrum (IR), $^1$H-NMR, $^{13}$C-NMR, and TOF-MS. Here, JIR-WINSPEC50 manufactured by JEOL Ltd. was used for infrared absorption spectrum, JNM-LA300 manufactured by JEOL Ltd. was used for $^1$H-NMR and $^{13}$C-NMR, and KOMPACT MALDIIV manufactured by Shimadzu Corp. was used for TOF-MS (ditto for the following).

IR: 1700 cm$^{-1}$ (ester);

TOF-MS: 296 (M/C);

$^1$H-NMR (heavy chloroform, δ ppm): 7.93 (1H, s, proton at 3-site of propenoic acid), 7.74 (1H, s, proton at 3'-site of aromatic ring), 6.72 (1H, s, proton at 6'-site of aromatic ring), 4.29 (2H, q, J=7 Hz, methylene group proton of ethyl group), 3.99 ppm (3H, s, methyl group proton of methoxy group), 3.96 (3H, s, methyl group proton of methoxy group), 1.92 (3H, s, methyl group proton at 2-site of propene), 1.36 (3H, t, J=7 Hz, methyl group proton of ethyl group) $^{13}$C-NMR (heavy chloroform, δ ppm): 167.9 (quaternary carbon, carbonyl carbon at 1-site), 153.1 (quaternary carbon, carbon at 5'-site of aromatic ring), 148.7 (quaternary carbon, carbon at 4'-site of aromatic ring), 145.1 (quaternary carbon, carbon at 2-site of propene), 143.4 (quaternary carbon, carbon at 2'-site of aromatic ring), 136.5 (CH, carbon at 3-site of propene), 126.6 (quaternary carbon, carbon at 1'-site of aromatic ring), 112.3 (CH, carbon at 6'-site of aromatic ring), 107.9 (CH, carbon at 3'-site of aromatic ring), 61.9 (CH$_2$, methylene group carbon of ethyl group), 56.5 (CH$_3$, methyl group carbon of methoxy group), 56.5 (CH$_3$, methyl group carbon of methoxy group), 14.3 (CH$_3$, methyl group carbon of ethyl group), 14.1 (CH$_3$, methyl group carbon at 2-site of propene).

Synthesis of 3-(4,5-dimethoxy-2-nitrophenyl)-2-methyl-2-propenoic acid

Into 250 ml of methanol, 11.3 g of thus obtained 3-(4,5-dimethoxy-2-nitrophenyl)-2-methyl-2-propenoic acid ethyl ester (1) were dissolved. With 45 ml of a 2-N aqueous sodium hydroxide solution being added thereto, the resulting mixture was reacted for 4 hours at 40° C. After the completion of the reaction, 1-N hydrochloric acid was used so as to adjust the pH of the solution at 4, the solution was cooled, and the precipitated crystal was filtered out, whereby 10.1 g of the aimed compound were obtained (yield: 99%).

The structure of this compound was verified by infrared absorption spectrum (IR), $^1$H-NMR, $^{13}$C-NMR, and TOF-MS.

IR: 1685 cm$^{-1}$ (carboxyl group); TOF-MS: 268 (M/C); $^1$H-NMR (heavy dimethyl sulfoxide, δ ppm): 12.60 (1H, bs, carboxyl group proton), 7.77 (1H, s, proton at 3-site of propene), 7.72 (1H, s, proton at 3'-site of aromatic ring), 6.97 (1H, s, proton at 6'-site of aromatic ring), 3.91 (3H, s, methyl group proton of methoxy group), 3.90 (3H, s, methyl group proton of methoxy group), 1.84 (3H, s, methyl group proton at 2-site of propene); $^{13}$C-NMR (heavy dimethyl sulfoxide, δ ppm): 168.7 (quaternary carbon, carboxyl group carbon at 1-site), 152.8 (quaternary carbon, carbon at 5'-site of aromatic ring), 148.2 (quaternary carbon, carbon at 4'-site of aromatic ring), 139.8 (quaternary carbon, carbon at 2'-site of aromatic ring), 135.5 (CH, carbon at 3-site of propene), 129.4 (quaternary carbon, carbon at 2-site of propene), 125.7 (quaternary carbon, carbon at 1'-site of aromatic ring), 112.7 (CH, carbon at 6'-site of aromatic ring), 107.7 (CH, carbon at 3'-site of aromatic ring), 56.4 (CH$_3$, methyl group carbon of methoxy group), 56.0 (CH$_3$, methyl group carbon of methoxy group), and 13.8 (CH$_3$, methyl group carbon at 2-site of propene).

Synthesis of (E) N-(o-di-t-butyloxy)-L-glutamic acid 3-(4,5-dimethoxy-2-nitrophenyl)-2-methyl-2-propenoic amide To 300 ml of dichloromethane anhydride, 9.1 g (34 mmol) of 3-(4,5-dimethoxy-2-nitrophenyl)-2-methyl-2-propenoic acid, 10.0 g (34 mmol) of glutamic acid di-t-butyl ester hydrochloride (manufactured by Sigma Chemical Co.), and 3.5 g (41 mmol) of triethylamine were added. Further, while this mixture was stirred under cooling with ice, 7.9 g (41 mmol) of 1-ethyl-3-(3-dimethylaminopropyl)-carbodiimide hydrochloride (EDC/HCl) in a powder form (manufactured by Wako Pure Chemical Industries, Ltd.) were added thereto in several portions. The reaction solution was returned to room temperature and stirred for one night. Then, most of the solvent was evaporated under a reduced pressure, and ethyl acetate and water were added to the residue. The resulting organic layer (ethyl acetate layer) was washed, dried, and concentrated, whereby 17.7 g of a brown oily product were obtained. This product was refined by a silica gel column chromatography using an eluent of chloroform/methanol at 20/1, whereby 16.26 g of the aimed compound were obtained as a gum-like solid (yield: 94%).

The structure of this compound was verified by $^1$H-NMR and $^{13}$C-NMR.

$^1$H-NMR (heavy chloroform, δ ppm): 7.74 (1H, s, proton at 3'-site of aromatic ring), 7.59 (1H, s, proton at 3-site of propenoic acid), 6.76 (1H, d, J=7.5 Hz, amide group proton), 6.71 (1H, s, proton at 6'-site of aromatic ring), 4.59 (1H, dt, J=7.5 Hz, 4.6 Hz, methine group proton at α-site of glutamic acid portion), 3.98 (3H, s, methyl group proton of methoxy group), 3.95 (3H, s, methyl group proton of methoxy group), 2.37 (2H, m, methylene group proton at γ-site of glutamic acid portion), 2.05 (2H, s, amino group proton), 2.03 (2H, m, methylene group proton at β-site of glutamic acid portion), 1.93 (9H, s, methyl group proton of butyl group), 1.92 (9H, s, methyl group proton of butyl group), 1.50 (3H, s, methyl group proton at 2-site of propene); $^{13}$C-NMR (heavy chloroform, δ ppm): 172.6 (quaternary carbon, carbonyl carbon in glutamic acid portion), 171.3 (carbonyl carbon in glutamic acid portion), 168.7 (quaternary carbon, carbonyl carbon at 1-site), 152.9 (quaternary carbon, carbon at 5'-site of aromatic ring), 148.7 (quaternary carbon, carbon at 4'-site of aromatic ring), 140.2 (quaternary carbon, carbon at 2-site of propene), 132.4 (quaternary carbon, carbon at 2'-site of aromatic ring), 131.8 (CH, carbon at 3-site of propene), 126.6 (quaternary carbon, carbon at 1'-site of aromatic ring), 112.4 (CH, carbon at 6'-site of aromatic ring), 107.8 (CH, carbon at 3'-site of aromatic ring), 82.4 (quaternary carbon, butyl group carbon), 81.1 (quaternarycarbon, butyl group carbon), 56.5 (CH$_3$, methyl group carbon of methoxy group), 56.4 (CH$_3$, methyl group carbon of methoxy group), 52.7 (CH, methine group carbon at α-site of glutamic acid portion), 31.6 (CH$_2$, methylene group carbon at γ-site of glutamic acid portion), 28.1 (CH$_3$, methyl group carbon of butyl group), 28.0 (CH$_2$, methylene group carbon at β-site of glutamic acid portion), 14.2 (CH$_3$, methyl group carbon at 2-site of propene).

Synthesis of (E) N-(o-di-t-butyloxy)-L-glutamic acid 3-(2-amino-4,5-dimethoxyphenyl)-2-methyl-2-propenoic amide Into a 500-ml brown four-neck flask, 15.1 g (30 mmol) of N-(o-di-t-butyloxy)-L-glutamic acid 3-(4,5-dimethoxy-2-nitrophenyl)-2-methyl-2-propenoic amide, 7.8 g (140 mmol) of iron powder (KosoChem. Co.), 130ml of acetic acid, and 10 ml of distilled water were collected, and the mixture was vigorously stirred for 3 hours with a mechanical stirrer at about 70° C. After the completion of the reaction was verified by TLC, the solution was cooled, and the unreacted iron powder and insoluble matters were filtered out. The filtrate was concentrated. The concentrated solution was dissolved in a mixed liquid of 200 ml of water/400 ml of ethyl acetate and washed three times with a saturated aqueous sodium bicarbonate solution. Then, insoluble matters were further filtered out. The ethyl acetate layer of this filtrate was successively washed with water, an aqueous sodium hydrogencarbonate solution, and a saturated saline solution; and was dried on sodium sulfate anhydride. Thereafter, the dried product was concentrated, whereby 15 g of a crude product were obtained.

Thus obtained product was further refined by a column chromatography (silica gel (aminopropyl-modified type) manufactured by Fuji Silysia Chem. Co., NH-DM1020 1000 g; eluent: hexane/ethyl acetate=1/1), whereby 11.5 g of the aimed compound were obtained (yield: 80%).

The structure of this compound was verified by $^1$H-NMR and $^{13}$C-NMR.

$^1$H-NMR (heavy chloroform, δ ppm): 7.34 (1H, s, proton at 3-site of propenoic acid), 6.75 (1H, d, J=7.3 Hz, amide group proton), 6.63 (1H, s, proton at 6'-site of aromatic ring), 6.30 (1H, s, proton at 3'-site of aromatic ring), 4.59 (1H, dt, J=7.3 Hz, 4.6 Hz, methine group proton at α-site of glutamic acid portion), 3.85 (3H, s, methyl group proton of methoxy group), 3.80 (3H, s, methyl group proton of methoxy group), 3.59 (2H, bs, amino group proton), 2.39 (2H, m, methylene group proton at γ-site of glutamic acid portion), 2.25 (2H, m, methylene group proton at β-site of glutamic acid portion), 2.05 (3H, s, methyl group proton at 2-site of propene), 1.50 (9H, s, methyl group proton of butyl group), 1.45 (9H, s, methyl group proton of butyl group); $^{13}$C-NMR (heavy chloroform, δ ppm): 172.6 (quaternary carbon, carbonyl carbon in glutamic acid portion), 171.2 (carbonyl carbon in glutamic acid portion), 168.7 (quaternary carbon, carbonyl carbon at 1-site), 150.4 (quaternary carbon, carbon at 4'-site of aromatic ring), 141.6 (quaternary carbon, carbon at 2'-site of aromatic ring), 139.2 (quaternary carbon, carbon at 5'-site of aromatic ring), 131.1 (CH, carbon at 3-site of propene), 131.1 (quaternary carbon, carbon at 2-site of propene), 113.6 (CH, carbon at 6'-site of aromatic ring), 112.8 (CH, carbon at 1'-site of aromatic ring), 100.3 (CH, carbon at 3'-site of aromatic ring), 82.4 (quaternary carbon, butyl group carbon), 80.8 (quaternary carbon, butyl group carbon), 56.7 (CH$_3$, methyl group carbon of methoxy group), 55.8 (CH$_3$, methyl group carbon of methoxy group), 52.8 (CH, methine group carbon at α-site of glutamic acid portion), 31.7 (CH$_2$, methylene group carbon at γ-site of glutamic acid portion), 28.1 (CH$_3$, methyl group carbon of butyl group), 27.5 (CH$_2$, methylene group carbon at β-site of glutamic acid portion), 14.2 (CH$_3$, methyl group carbon at 2-site of propene).

Synthesis of (E) N-L-glutamic acid 3-(2-amino-4,5-dimethoxyphenyl)-2-methyl-2-propenoic amide At room temperature, 10.4 g (22 mmol) of (E) N-(o-di-t-butyloxy)-L-glutamic acid 3-(2-amino-4,5-dimethoxyphenyl)-2-methyl-2-propenoic amide, 20 ml of 1-N hydrochloric acid/methanol solution, and 50 ml of dichloromethane were stirred for one night. After the completion of the reaction was verified by TLC, the reaction liquid was concentrated under a reduced pressure as it was, whereby 20 g of an oily product were obtained. This product was once dissolved in 30 ml of water, and was lyophilized in order to eliminate remaining hydrochloric acid. From the resulting lyophilized product, 9.9 g were refined by a silica gel column chromatography using a moving phase of chloroform/methanol/trifluoroacetic acid at 100/10/1 to 40/10/1, and then were lyophilized, whereby 5.7 g of the aimed compound were obtained (yield: 71%).

The structure of this compound was verified by $^1$H-NMR and $^{13}$C-NMR.

$^1$H-NMR (heavy dimethyl sulfoxide, δ ppm): 8.44 (1H, d, J=7.5 Hz, amide group proton), 7.34 (1H, s, proton at 3-site of propenoic acid), 7.24 (1H, s, proton at 3'-site of aromatic ring), 6.94 (1H, s, proton at 6'-site of aromatic ring), 4.36 (1H, ddd, J=9.3 Hz, 7.7 Hz, 5.5 Hz, methine group proton at α-site of glutamic acid portion), 4.10 (2H, bs, amino group proton), 3.82 (6H, s, methyl group proton of methoxy group), 2.47 (2H, dd, J=7.5 Hz, 7.5 Hz, methylene group proton at γ-site of glutamic acid portion), 2.07 (2H, m, methylene group proton at β-site of glutamic acid portion), 1.97 (3H, s, methyl group proton bound to 2-site of propene); $^{13}$C-NMR (heavy dimethyl sulfoxide, δ ppm): 169.3, 169.1, 169.0 (quaternary carbon, carbonyl carbon in glutamic acid portion and carbonyl carbon at 1-site), 148.6 (quaternary carbon, carbon at 4'-site of aromatic ring), 147.8 (quaternary carbon, carbon at 2'-site of aromatic ring), 135.1 (quaternary carbon, carbon at 5'-site of aromatic ring), 126.9 (CH, carbon at 3-site of propene), 122.6 (quaternary carbon, carbon at 1'-site of aromatic ring), 112.8 (CH, carbon at 6'-site of aromatic ring), 107.6 (CH, carbon at 3'-site of aromatic ring), 55.8 (CH$_3$, methyl group carbon of methoxy group ), 55.7 (CH$_3$, methyl group carbon of methoxy group), 51.7 (CH, methine group carbon at α-site of glutamic acid portion), 30.3 (CH$_2$, methylene group carbon at γ-site of glutamic acid portion), 26.0 (CH$_2$, methylene group carbon at β-site of glutamic acid portion), 14.5 (CH$_3$, methyl group carbon bound to 2-site of propene).

Synthesis of 3-(4,5-dimethoxy-2-nitrophenyl)-2-methyl-2-propenoic acid N-succinimide ester Into 100 ml of dichloromethane, 7.0 g (26.2 mmol) of 3-(4,5-dimethoxy-2-nitrophenyl)-2-methyl-2-propenoic acid (2) and 3.5 g (30.0 mmol) of N-hydroxysuccinimide (manufactured by Wako Pure Chemical Industries, Ltd.) were dissolved, and 500 mg of dimethylaminopyridine (manufactured by Wako Pure Chemical Industries, Ltd.) were added thereto. While this solution was stirred under cooling with ice, 6.3 g (33.0 mmol) of 1-ethyl-3-(3-dimethylaminopropyl) -carbodiimide hydrochloride (EDC-HCl) (manufactured by Wako Pure Chemical Industries, Ltd.) were added thereto in portions. The mixture was returned to room temperature and then was stirred for 2 hours. After the end point of this reaction was verified by a thin layer chromatograph (TLC), the reaction liquid was concentrated under a reduced pressure and then was dissolved in 100 ml of ethyl acetate. After this solution was washed and dried, the solvent was evaporated, whereby 8.3 g of the aimed product were obtained as an oily product (yield: 81%).

The structure of this compound was verified by $^1$H-NMR and $^{13}$C-NMR.

$^1$H-NMR (dimethyl sulfoxide, δ ppm): 8.29 (1H, s, proton at 3-site of propene), 7.78 (1H, s, proton at 3'-site of aromatic ring), 7.14 (1H, s, proton at 6'-site of aromatic ring), 3.94 (3H, s, methyl proton of methoxy group), 3.92 (3H, s, methyl proton of methoxy group), 2.87 (4H, s, methylene proton of succimidyl group), 2.01 (3H, s, methyl group proton at 2-site of propene); $^{13}$C-NMR (heavy dimethyl sulfoxide, δ ppm): 170.4 (quaternary carbon, carbonyl carbon of succinimidyl group), 162.9 (quaternary carbon, carbonyl group carbon at 1-site), 153.1 (quaternary carbon, carbon at 5'-site of aromatic ring), 149.0 (quaternary carbon, carbon at 4'-site of aromatic ring), 141.3 (CH, carbon at 3-site of propene), 139.8 (quaternary carbon, carbon at 2'-site of aromatic ring), 124.3 (quaternary carbon, carbon at 2-site of propene), 123.7 (quaternary carbon, carbon at 1'-site of aromatic ring), 113.0 (CH, carbon at 6'-site of aromatic ring), 107.7 (CH, carbon at 3'-site of aromatic ring), 56.6 (CH$_3$, methyl group carbon of methoxy group), 56.0 (CH$_3$, methyl group carbon of methoxy group), 25.5 (CH$_2$, methylene group carbons at 3"- and 4"-sites of succinimidyl group), 13.8 (CH$_3$, methyl group carbon at 2-site of propene).

Synthesis of (E) 3-(2-amino-4,5-dimethoxyphenyl)-2-methyl-2-propenoic acid N-succinimide ester Into a mixed solvent of 70 ml of acetic acid and 5 ml of water, 8.3 g (22.8 mmol) of 3-(4,5-dimethoxy-2-nitrophenyl)-2-methyl-2-propenoic acid N-succinimidyl ester (3) were dissolved; and, with 5.0 g (89.5 mmol) of iron powder being added thereto, the mixture was heated to 70° C. After a reaction of 2 hours, insoluble matters were filtered out, and the filtrate was added to 500 ml of water. The resulting crystal was filtered out, washed with water, and dried, whereby 6.2 g of the aimed compound were obtained as a crystal (yield: 81%).

The structure of this compound was verified by $^1$H-NMR and $^{13}$C-NMR.

$^1$H-NMR (heavy dimethylsulfoxide, δ ppm): 7.82 (1H, s, proton at 3-site of propene), 6.81 (1H, s, proton at 6'-site of aromatic ring), 6.44 (1H, s, proton at 3'-site of aromatic ring), 5.20 (2H, bs, aniline-type amino group proton), 3.73 (3H, s, methyl group proton of methoxy group), 3.67 (3H, s, methyl group proton of methoxy group), 2.85 (4H, s, methylene group proton of succinimidyl group), 2.16 (3H, s, methyl group proton at 2-site of propene); $^3$C-NMR (DMSO-d$_6$, δ ppm): 170.4 (quaternary carbon, carbonyl carbon of succinimidyl group), 163.8 (quaternary carbon, carbonyl carbon at 1-site), 152.0 (quaternary carbon, carbon at 4'-site of aromatic ring), 144.5 (quaternary carbon, carbon at 2'-site of aromatic ring), 140.1 (CH, carbon at 3-site of propene), 140.0 (quaternary carbon, carbon at 5'-site of aromatic ring), 118.2 (quaternary carbon, carbon at 2-site of propene), 113.9 (CH, carbon at 6'-site of aromatic ring), 109.5 (quaternary carbon, carbon at 1'-site of aromatic ring), 99.8 (CH, carbon at 3'-site of aromatic ring), 56.3 (CH$_3$, methyl group carbon of methoxy group), 55.1 (CH$_3$, methyl group carbon of methoxy group), 25.4 (CH$_{21}$ methylene group carbons at 3"- and 4"-sites of succinimidyl group), 14.3 (CH$_3$, methyl group carbon at 2-site of propene).

Synthesis of (E) N-L-glutamic acid 3-(2-amino- 4, 5-dimethoxyphenyl)-2-methyl-2-propenoic amide Into 40 ml of dimethylformamide, 0.5 g (1.5 mmol) of (E) 3-(2-amino-4,5-dimethoxyphenyl)-2-methyl-2-propenoic acid N-succinimide ester was dissolved; and, with an aqueous solution in which 2.3 g (10 mmol) of L-glutamic acid had been dissolved in 80 ml of a 0.5-N aqueous sodium hydrogencarbon ate solution being added thereto, the mixture was reacted for 4 hours at room temperature. After its pH was adjusted to 4 with 2-N hydrochloric acid being added thereto, the reaction liquid was concentrated under a reduced pressure as it was. The concentrated product was once dissolved in 30 ml of water, and was lyophilized in order to eliminate remaining hydrochloric acid. The resulting lyophilized product was refined by a silica gel column chromatography using a moving phase of chloroform/methanol/trifluoroacetic acid at 100/10/0.01 to 40/10/0.01, and then was lyophilized, whereby 0.35 g of the aimed compound was obtained (yield: 63%).

The structure of this compound was verified by $^1$H-NMR and $^{13}$C-NMR.

$^1$H-NMR (heavy dimethyl sulfoxide, δ ppm): 8.44 (1H, d, J=7.5 Hz, amide group proton), 7.34 (1H, s, proton at 3-site of propenoic acid), 7.24 (1H, s, proton at 3'-site of aromatic ring), 6.94 (1H, s, proton at 6'-site of aromatic ring), 4.36 (1H, ddd, J=9.3 Hz, 7.7 Hz, 5.5 Hz, methine group proton at α-site of glutamic acid portion), 4.10 (2H, bs, amino group proton), 3.82 (6H, s, methyl group proton of methoxy group), 2.47 (2H, dd, J=7.5 Hz, 7.5 Hz, methylene group proton at γ-site of glutamic acid portion), 2.07 (2H, m, methylene group proton at β-site of glutamic acid portion), 1.97 (3H, s, methyl group proton bound to 2-site of propene); $^{13}$C-NMR (heavy dimethyl sulfoxide, δ ppm): 169.3, 169.1, 169.0 (quaternary carbon, carbonyl carbon in glutamic acid portion and carbonyl carbon at 1-site), 148.6 (quaternary carbon, carbon at 4'-site of aromatic ring), 147.8 (quaternary carbon, carbon at 2'-site of aromatic ring), 135.1 (quaternary carbon, carbon at 5'-site of aromatic ring), 126.9 (CH, carbon at 3-site of propene), 122.6 (quaternary carbon, carbon at 1'-site of aromatic ring), 112.8 (CH, carbon at 6'-site of aromatic ring), 107.6 (CH, carbon at 3'-site of aromatic ring), 55.8 (CH$_3$, methyl group carbon of methoxy group), 55.7 (CH$_3$, methyl group carbon of methoxy group), 51.7 (CH, methine group carbon at α-site of glutamic acid portion), 30.3 (CH$_2$, methylene group carbon at γ-site of glutamic acid portion), 26.0 (CH$_2$, methylene group carbon at β-site of glutamic acid portion), 14.5 (CH$_3$, methyl group carbon bound to 2-site of propene).

Synthesis of (E) N-(o-di-t-butyloxy)-L-glutamic acid 3-(2-amino-4,5-dimethoxyphenyl)-2-methyl-2-propenoic amide Into 200 ml of tetrahydrofuran, 0.33 g (1.0 mmol) of (E) 3-(2-amino-4,5-dimethoxyphenyl)-2-methyl-2-propenoic acid N-succinimide ester and 0.89 g (3.0 mmol) of glutamic acid di-t-butyl ester hydrochloride (manufactured by Sigma Chemical Co.) were dissolved, and the mixture was reacted at room temperature for 4 hours. The solvent was eliminated under a reduced pressure, and ethyl acetate and water were added to the residue. The ethyl acetate layer was washed, dried on sodium sulfate anhydride, and then concentrated, whereby a crude product was obtained. Thus obtained product was refined by a column chromatography (silica gel (aminopropyl-modified type) manufactured by Fuji Silysia Chem. Co., NH-DM1020 1000 g; eluent: hexane/ethyl acetate=1/1), whereby 0.32 g of the aimed product was obtained (yield: 65%).

The structure of this compound was verified by $^1$H-NMR and $^{13}$C-NMR.

$^1$H-NMR (heavy chloroform, δ ppm): 7.34 (1H, s, proton at 3-site of propenoic acid), 6.75 (1H, d, J=7.3 Hz, amide group proton), 6.63 (1H, s, proton at 6'-site of aromatic ring), 6.30 (1H, s, proton at 3'-site of aromatic ring), 4.59 (1H, dt, J=7.3 Hz, 4.6 Hz, methine group proton at α-site of glutamic acid portion), 3.85 (3H, s, methyl group proton of methoxy group), 3.80 (3H, s, methyl group proton of methoxy group), 3.59 (2H, bs, amino group proton), 2.39 (2H, m, methylene group proton at γ-site of glutamic acid portion), 2.25 (2H, m, methylene group proton at β-site of glutamic acid portion), 2.05 (3H, s, methyl group proton at 2-site of propene), 1.50 (9H, s, methyl group proton of butyl group), 1.45 (9H, s, methyl group proton of butyl group); $^{13}$C-NMR (heavy chloroform, δ ppm): 172.6 (quaternary carbon, carbonyl carbon in glutamic acid portion), 171.2 (carbonyl carbon in glutamic acid portion), 168.7 (quaternary carbon, carbonyl carbon at 1-site), 150.4 (quaternary carbon, carbon at 4'-site of aromatic ring), 141.6 (quaternary carbon, carbon at 2'-site of aromatic ring), 139.2 (quaternary carbon, carbon at 5'-site of aromatic ring), 131.1 (CH, carbon at 3-site of propene), 131.1 (quaternary carbon, carbon at 2-site of propene), 113.6

(CH, carbon at 6'-site of aromatic ring), 112.8 (CH, carbon at 1'-site of aromatic ring), 100.3 (CH, carbon at 3'-site of aromatic ring), 82.4 (quaternary carbon, butyl group carbon), 80.8 (quaternary carbon, butyl group carbon), 56.7 ($CH_3$, methyl group carbon of methoxy group), 55.8 ($CH_3$, methyl group carbon of methoxy group), 52.8 (CH, methine group carbon at α-site of glutamic acid portion), 31.7 ($CH_2$, methylene group carbon at γ-site of glutamic acid portion), 28.1 ($CH_3$, methyl group carbon of butyl group), 27.5 ($CH_2$, methylene group carbon at β-site of glutamic acid portion), 14.2 ($CH_3$, methyl group carbon at 2-site of propene).

Synthesis of 3-nitro-2-naphtaldehyde

The synthesis of 3-nitro-2-naphtaldehyde was carried out in conformity to a method described in literatures (Kienzle, Frank, Helv. Chim. Acta, 63 (8), 2364–2369 (1980); and Wani, Mansukh C., Ronman, Peter E., Lindley, James T., and Wall, Monroe E., J. Med. Chem. 1980, 23, 554–560).

The structure of this compound was verified by $^1$H-NMR and $^{13}$C-NMR.

$^1$H-NMR (heavy chloroform, δ ppm): 10.52 (1H, s, formyl group proton), 8.68 (1H, s, proton at 4-site), 8.47 (1H, s, proton at 1-site), 8.12–8.05 (2H, m, protons at 5- and 8-sites), 7.82–7.76 (2H, m, protons at 6- and 7-sites); $^{13}$C-NMR (heavy chloroform, δ ppm): 188.2 (CH, formyl group carbon), 159.4 (quaternary carbon, carbon at 2-site), 145.9 (quaternary carbon, carbon at 3-site), 134.2 (quaternary carbon, carbon at 4a-site), 133.7 (quaternary carbon, carbon at 8a-site), 132.1 (CH, carbon at 1-site), 130.6 (CH, carbon at 6- or 7-site), 130.5 (CH, carbon at 6- or 7-site), 129.8 (CH, carbon at 5- or 8-site), 129.6 (CH, carbon at 5- or 8-site), 126.0 (CH, carbon at 4-site).

Synthesis of 3-(2-nitro-benzo[d]phenyl)-2-methyl-2-propenoic acid ethyl ester To 200 ml of benzene, 9.3 g (46 mmol) of 3-nitro-2-naphtaldehyde and 17.6 g (48.5 mmol) of Wittig reagent (carbethoxy ethylidene triphenylphosphorane) (manufactured by Aldrich Chemical Co., Inc.) were added, and the resulting mixture was stirred at room temperature for one night. The completion of the reaction was verified by TLC, and the reaction liquid was concentrated, whereby a crude product was obtained. This crude product was refined by a column chromatography (aminopropyl-modified silica gel (Fuji Silysia Chem. Co., NH-DM); developing solvent: hexane/ethyl acetate=1/1), whereby 13.0 g of the aimed compound were obtained as a crystal (yield: 96%).

The structure of this compound was verified by $^1$H-NMR and $^{13}$C-NMR.

$^1$H-NMR (heavy chloroform, δ ppm): 8.70 (1H, s, proton at 3'-site of aromatic ring), 8.03–8.00 (2H, m, protons at 4'- and 7'-sites of aromatic ring), 7.80 (1H, s, proton at 3-site of propene), 7.78 (1H, s, proton at 8'-site of aromatic ring), 7.74–7.63 (2H, m, protons at 5'- and 6'-sites of aromatic ring), 4.32 (2H, q, J=7 Hz, methylene group proton of ethyl group), 3.89 (2H, bs, $NH_2$), 2.00 (3H, s, methyl group proton bound to 2-site of propene), 1.37 (3H, t, J=7 Hz, methyl group proton of ethyl group); $^{13}$C-NMR (heavy chloroform, δ ppm): 167.8 (quaternary carbon, carbonyl carbon at 1-site), 145.8 (quaternary carbon, carbon at 2'-site of aromatic ring), 135.7 (CH, carbon at 3-site of propene), 134.6 (quaternary carbon, carbon at 7a'-site of aromatic ring), 131.4 (quaternary carbon, carbon at 3a'-site of aromatic ring), 131.0 (CH, carbon at 8'-site of aromatic ring), 130.0 (quaternary carbon, carbon at 1'-site of aromatic ring), 129.9 (CH, carbon at 5'- or 6'-site of aromatic ring), 129.4 (CH, carbon at 5'- or 6'-site of aromatic ring), 128.3 (CH, carbon at 4'- or 7'-site of aromatic ring), 127.9 (CH, carbon at 4'- or 7-site of aromatic ring), 127.7 (quaternary carbon, carbon at 2-site of propene), 125.8 (CH, carbon at 3'-site of aromatic ring), 61.1 ($CH_2$, methylene group carbon of ethyl group), 14.3 ($CH_3$, methyl group carbon of ethyl group), 14.0 ($CH_3$, carbon of methyl group bound to 2-site of propene).

Synthesis of 3-(2-nitro-benzo[d]phenyl)-2-methyl-2-propenoic acid

Into 130 ml of methanol, 5.48 g (19 mmol) of 3-(2-nitro-benzo[d]phenyl)-2-methyl-2-propenoic acid ethyl ester were dissolved; and, with 23 ml of a 2-N aqueous sodium hydroxide solution being added thereto, the resulting mixture was reacted at 40° C. for one night. After the completion of the reaction was confirmed by TLC, the reaction liquid was concentrated under a reduced pressure. The pH of the concentrated product was adjusted to 1 with 1-N hydrochloric acid being added thereto, and the precipitated crystal was filtered out. This crystal was washed with water and a small amount of methanol, and was dried, whereby 4.8 g of the aimed compound were obtained as a crystal (yield: 98%).

The structure of this compound was verified by $^1$H-NMR and $^{13}$C-NMR.

$^1$H-NMR (heavy dimethyl sulfoxide, δ ppm): 8.90 (1H, s, proton at 3'-site of aromatic ring), 8.25–8.12 (2H, m, protons at 4'- and 7'-sites of aromatic ring), 8.08 (1H, s, proton at 3-site of propene), 7.85 (1H, s, proton at 8'-site of aromatic ring), 7.82–7.71 (2H, m, protons at 5'- and 6'-sites of aromatic ring), 1.93 (3H, s, methyl group proton bound to 2-site of propene); $^{13}$C-NMR (heavy dimethyl sulfoxide, δ ppm): 168.6 (quaternary carbon, carbonyl carbon at 1-site), 145.6 (quaternary carbon, carbon at 2'-site of aromatic ring), 134.9 (CH, carbon at 3-site of propene), 134.2 (quaternary carbon, carbon at 7a'-site of aromatic ring), 131.0 (CH, quaternary carbon, carbon at 8'-site of aromatic ring), 130.9 (quaternary carbon, carbon at 3a'-site of aromatic ring), 130.0 (CH, carbon at 5'- or 6'-site of aromatic ring), 129.9 (quaternary carbon, carbon at 1'-site of aromatic ring), 129.4 (CH, carbon at 5'- or 6'-site of aromatic ring), 128.3 (CH, carbon at 4'- or 7'-site of aromatic ring), 128.0 (CH, carbon at 4'- or 7'-site of aromatic ring), 126.8 (quaternary carbon, carbon at 2-site of propene), 125.6 (CH, carbon at 3'-site of aromatic ring), 13.7 ($CH_3$, carbon of methyl group bound to 2-site of propene).

Synthesis of (E) 3-(2-nitro-benzo[d]phenyl)-2-methyl-2-propenoic acid N-hydroxysuccinimide ester Into 90 ml of dichloromethane, 7.8 g (19 mmol) of 3-(2-nitro-benzo[d]phenyl)-2-methyl-2-propenoic acid and 3.28 g (28.5 mmol) of N-hydroxysuccinimide (manufactured by Wako Pure Chemical Industries, Ltd.) were dissolved; and 230 mg of dimethylaminopyridine (manufactured by Wako Pure Chemical Industries, Ltd.) were added thereto. While this solution was stirred under cooling with ice, 5.46 g (28.5 mmol) of 1-ethyl-3-(3-dimethylaminopropyl)-carbodiimide hydrochloride (EDC-HCl) (manufactured by Wako Pure Chemical Industries, Ltd.) were added thereto in portions. The mixture was returned to room temperature and stirred for one night. The resulting reaction liquid was concentrated under a reduced pressure, and thus concentrated product was dissolved in 100 ml of ethyl acetate. The resulting solution was washed and dried, and the solvent was evaporated. Thus obtained crude product was refined by a column chromatography (aminopropyl-modified silica gel (Fuji Sylisia Chem. Co., NH-DM); developing solvent: hexane/ethyl acetate=1/1), whereby 6.7 g of the aimed compound were obtained as a crystal (yield: 98%).

The structure of this compound was verified by $^1$H-NMR and $^{13}$C-NMR.

$^1$H-NMR (heavy methyl sulfoxide, δ ppm): 9.00 (1H, s, proton at 3'-site of aromatic ring), 8.30–8.14 (2H, m, protons at 4'- and 7'-sites of aromatic ring), 8.24 (1H, s, protons at 3-site of propene and at 8'-site of aromatic ring), 7.86–7.75 (2H, m, protons at 5'- and 6'-sites of aromatic ring), 2.89 (4H, s, methylene group proton of succinimidyl group), 2.10 (3H, s, methyl group proton bound to 2-site of propene); $^{13}$C-NMR (heavy methyl sulfoxide, δ ppm): 170.2 (quaternary carbon, carbonyl carbon of succinimidyl group), 163.0 (quaternary carbon, carbonyl carbon at 1-site), 145.0 (quaternary carbon, carbon at 2'-site of aromatic ring), 134.2 (CH, carbon at 3-site of propene), 131.4 (CH, carbon at 8'-site of aromatic ring), 130.4 (CH, carbon at 5'- or 6'-site of aromatic ring), 129.7 (CH, carbon at 5'- or 6'-site of aromatic ring), 128.8 (CH, carbon at 4'- or 7'-site of aromatic ring), 128.2 (CH, carbon at 4'- or 7'-site of aromatic ring), 126.1 (CH, carbon at 3'-site of aromatic ring), 125.6 (quaternary carbon, carbon at 2-site of propene), 25.5 (CH$_2$, methylene group carbon of succinimidyl group), 13.7 (CH$_3$, methyl group carbon bound to 2-site of propene).

Synthesis of (E) 3-(2-amino-benzo[d]phenyl)-2-methyl-2-propenoic acid N-hydroxysuccinimide ester Into a mixed solvent of 70 ml of acetic acid and 5 ml of water, 6.7 g (19 mmol) of 3-(2-nitro-benzo[d]phenyl)-2-methyl-2-propenoic acid N-hydroxysuccinimide ester were dissolved; and, with 4.7 g (89.5 mmol) of iron powder (manufactured by Koso Chem. Co.) being added thereto, the mixture was heated to 70° C. After a reaction of 1.5 hours, insoluble matters were filtered out, and the filtrate was added to 300 ml of water. The resulting mixture was twice extracted with 400 ml of ethyl acetate, and thus obtained solution was successively washed with water, an aqueous sodium hydrogencarbon ate solution, and a saturated aqueous sodium chloride solution. The washed product was dried on sodium sulfate anhydride and concentrated, whereby 4.2 g of the aimed compound were obtained (yield: 66%).

The structure of this compound was verified by $^1$H-NMR.

$^1$H-NMR (heavy dimethyl sulfoxide, δ ppm): 7.94 (1H, s, proton at 3-site of propene), 7.77 (1H, s, proton at 8'-site of aromatic ring), 7.73–7.49 (2H, m, protons at 4'- and 7'-sites of aromatic ring), 7.36–7.12 (2H, m, protons at 5'- and 6'-sites of aromatic ring), 7.04 (1H, s, proton at 3'-site of aromatic ring), 3.30 (2H, amino group proton), 2.87 (4H, s, methylene proton of succinimidyl group), 2.18 (3H, s, methyl group proton bound to 2-site of propene).

Synthesis of 3-(2-amino-4,5-dimethoxyphenyl)-2-methyl-2-propenoic acid ethyl ester Into 250 ml of glacial acetic acid, 19.0 g of 3-(4,5-dimethoxy-2-nitrophenyl)-2-methyl-2-propenoic acid ethyl ester were dissolved; and, with 15.0 g of iron powder and 20 ml of ion-exchanged water being added thereto, the mixture was refluxed under heating for 40 minutes. The resulting reaction liquid was filtered out, the filtrate was concentrated under a reduced pressure, and thus obtained residue was dissolved in ethyl acetate. The resulting product was successively washed with water, a 5% aqueous sodium hydrogencarbon ate solution, and a saturated aqueous sodium chloride solution; and then was left on sodium sulfate anhydride for one night so as to be dried. Ethyl acetate was evaporated under a reduced pressure from this solution, and the resulting crude product was recrystallized from hexane/ethanol, whereby 12.5 g of the aimed product were obtained (yield: 78%).

The structure of this compound was verified by $^1$H-NMR and $^{13}$C-NMR.

$^1$H-NMR (heavy chloroform, δ ppm): 7.57 (1H, s, proton at 3-site of propenoic acid), 6.68 (1H, s, proton at 6'-site of aromatic ring), 6.29 (1H, s, proton at 3'-site of aromatic ring), 4.25 (2H, q, J=7 Hz, methylene group proton of ethyl group), 3.84 (3H, s, methyl group proton of methoxy group), 3.79 (3H, s, methyl group proton of methoxy group), 3.57 (2H, bs, amino group proton), 2.03 (3H, s, methyl group proton at 2-site of propene), 1.33 (3H, t, J=7 Hz, methyl group proton of ethyl group); $^{13}$C-NMR (heavy chloroform, δ ppm): 168.6 (quaternary carbon, carbonyl carbon at 1-site), 150.6 (quaternary carbon, carbon at 4'-site of aromatic ring), 141.6 (quaternary carbon, carbon at 2'-site of aromatic ring), 139.6 (quaternary carbon, carbon at 5'-site of aromatic ring), 134.6 (CH, carbon at 3-site of propene), 128.2 (quaternary carbon, carbon at 2-site of propene), 113.5 (CH, carbon at 6'-site of aromatic ring), 112.7 (quaternary carbon, carbon at 1'-site of aromatic ring), 100.3 (quaternary carbon, carbon at 3'-site of aromatic ring), 60.8 (CH$_2$, methylene group carbon of ethyl group), 56.7 (CH$_3$, methyl group carbon of methoxy group), 55.8 (CH$_3$, methyl group carbon of methoxy group), 14.4 (CH$_3$, methyl group carbon of ethyl group), 14.3 (CH$_3$, methyl group carbon at 2-site of propene).

Synthesis of (E) 3-(2-amino-4,5-dimethoxyphenyl)-2-methyl-2-propenoic acid

Into 10 ml of tetrahydrofuran (THF), 1.0 g of (E) 3-(2-amino-4,5-dimethoxyphenyl)-2-methyl-2-propenoic acid ethyl ester was dissolved; and, with 10 ml of a 1-N aqueous sodium hydroxide solution being added thereto, the mixture was reacted at 40° C. for 4 hours. After the completion of the reaction, the mixture was cooled with 10 ml of 1-N hydrochloric acid being added thereto, and the precipitated crystal was filtered out, whereby 0.85 g of the aimed compound was obtained (95%).

The structure of this compound was verified by $^1$H-NMR and $^{13}$C-NMR.

$^1$H-NMR (heavy dimethyl sulfoxide, δ ppm):7.51 (1H, s, proton at 3-site of propenoic acid), 6.70 (1H, s, proton at 6'-site of aromatic ring), 6.42 (1H, s, proton at 3'-site of aromatic ring), 3.72 (3H, s, methyl group proton of methoxy group), 3.65 (3H, s, methyl group proton of methoxy group), 3.36 (2H, bs, amino group proton), 1.98 (3H, s, methyl group proton at 2-site of propene); $^{13}$C-NMR (heavy dimethyl sulfoxide, δ ppm): 169.7 (quaternary carbon, carbonyl carbon at 1-site), 150.7 (quaternary carbon, carbon at 4'-site of aromatic ring), 142.6 (quaternary carbon, carbon at 2'-site of aromatic ring), 139.8 (quaternary carbon, carbon at 5'-site of aromatic ring), 134.7 (CH, carbon at 3-site of propene), 125.2 (quaternary carbon, carbon at 2-site of propene), 114.3 (CH, carbon at 6'-site of aromatic ring), 111.0 (quaternary carbon, carbon at 1'-site of aromatic ring), 100.1 (quaternary carbon, carbon at 3'-site of aromatic ring), 60.8 (CH$_2$, methylene group carbon of ethyl group), 56.5 (CH$_3$, methyl group carbon of methoxy group), 55.1 (CH$_3$, methyl group carbon of methoxy group), 14.4 (CH$_3$, methyl group carbon of ethyl group), 14.3 (CH$_3$, methyl group carbon at 2-site of propene).

Synthesis of (E) 3-(2-amino-4,5-dimethoxyphenyl)-2-methyl-2-propenoic acid p-nitrophenyl ester Into 20 ml of dichloromethane, 0.82 g (3.5 mmol) of (E) 3-(2-amino-4,5-dimethoxyphenyl)-2-methyl-2-propenoic acid and 0.97 g (7 mmol) of p-nitrophenol (manufactured by Wako Pure Chemical Industries, Ltd.) were dissolved, and 40 mg of dimethylaminopyridine (manufactured by Wako Pure Chemical Industries, Ltd.) were added thereto. While this mixture was stirred under cooling with ice, 0.81 g (4.2 mmol) of 1-ethyl-3-(3-dimethylaminopropyl)-carbodiimide hydrochloride (EDC/HCl) (manufactured by Wako Pure Chemical Industries, Ltd.) were added thereto in portions. The mixture was returned to room temperature and then was stirred for 20 hours. After the end point of the reaction was verified by TLC, the reaction liquid was concentrated under a reduced pressure and then was dissolved in 100 ml of ethyl acetate. After this solution was washed and dried, the solvent was evaporated, whereby a syrupy crude product was obtained. This product was refined by a silica gel column chromatography (n-hexane/ethyl acetate=2/1), whereby 0.15 g of the aimed compound was obtained as a yellow crystal (yield: 12%).

The structure of this compound was verified by $^1$H-NMR and $^{13}$C-NMR.

$^1$H-NMR (heavy chloroform, δ ppm): 8.31 (2H, d, J=9 Hz, protons at 2"- and 6"-sites of p-nitrophenyloxy group), 7.88 (1H, s, proton at 3-site of propene), 7.36 (2H, d, J=9 Hz, protons at 3"- and 5"-sites of p-nitrophenyloxy group), 6.79 (1H, s, proton at 6'-site of cinnamyl aromatic ring), 6.33 (1H, s, proton at 3'-site of cinnamyl aromatic ring), 3.88 (3H, s, methyl group proton of methoxy group), 3.84 (3H, s, methyl group proton of methoxy group), 3.68 (2H, bs, amino group proton), 2.20 (3H, s, m, methyl group proton at 2-site of propene); $^{13}$C-NMR (heavy chloroform, δ ppm): 166.2 (quaternary carbon, carbonyl group carbon at 1-site), 156.1 (quaternary carbon, carbon at 1"-site of p-nitrophenyloxy group), 151.5 (quaternary carbon, carbon at 4'-site of cinnamyl aromatic ring), 145.2 (quaternary carbon, carbon at 4"-site of p-nitrophenyloxy group), 141.9 (quaternary carbon, carbon at 2'-site of cinnamyl aromatic ring), 140.3 (quaternary carbon, carbon at 51'-site of cinnamyl aromatic ring), 137.7 (CH, carbon at 3-site of propene), 125.6 (quaternary carbon, carbon at 2-site of propene), 125.2 (CH, carbons at 3"- and 5"-sites of p-nitrophenyloxy group), 122.6 (CH, carbons at 2"- and 6"-sites of p-nitrophenyloxy group), 113.4 (CH, carbon at 6'-site of cinnamyl aromatic carbon), 112.0 (quaternary carbon, carbon at 1'-site of cinnamyl aromatic ring), 100.4 (CH, carbon at 3'-site of cinnamyl aromatic ring), 56.7 (CH$_3$, methyl group carbon of methoxy group), 55.8 (CH$_3$, methyl group carbon of methoxy group), 14.5 (CH$_3$, methyl group carbon bound to 2-site of propene).

Synthesis of (E) 3-(2-amino-4,5-dimethoxyphenyl)-2-methyl-2-propenoic acid phenethyl amide Into 30 ml of dimethylformamide, 0.72 g (2.0 mmol) of (E) 3-(2-amino-4,5-dimethoxyphenyl)-2-methyl-2-propenoic acid p-nitrophenyl ester obtained above and 0.48 g (4.0 mmol) of 2-phenylethylamine (manufactured by Tokyo Kasei Kogyo Co., Ltd.) were dissolved; and the mixture was reacted at room temperature for one night. The solvent was eliminated under a reduced pressure, and the residue was dissolved in ethyl acetate. After the resulting solution was washed and was dried with magnesium sulfate anhydride, the solvent was eliminated under a reduced pressure, whereby a crude product was obtained. This product was refined by an aminopropyl-modified type silica gel column chromatography (n-hexane/ethyl acetate=1/1), whereby 0.68 g of the aimed compound was obtained (yield: quantitative).

The structure of this compound was verified by $^1$H-NMR and $^{13}$C-NMR.

$^1$H-NMR (heavy chloroform, δ ppm): 7.35–7.30 (2H, m, protons at 2"- and 6"-sites of phenethyl aromatic ring), 7.26–7.21 (4H, m, protons at 3-site of propene and at 3"-, 4"-, and 5"-sites of phenethyl aromatic ring), 6.60 (1H, s, proton at 6'-site of cinnamate aromatic ring), 6.29 (1H, s, proton at 3'-site of cinnamate aromatic ring), 5.93 (1H, bs, amino proton of amide group), 3.84 (3H, s, methyl group proton of methoxy group), 3.78 (3H, s, methyl group proton of methoxy group), 3.64 ppm (2H, dt, J=7 Hz, methylene group proton of phenethyl), 3.54 ppm (2H, s, amino group proton), 2.90 ppm (2H, t, J=7 Hz, methylene group proton of phenethyl), 1.96 ppm (3H, s, methyl group proton bound to 2-site of propene); $^{13}$C-NMR (heavy chloroform, δ ppm): 169.1 (quaternary carbon, carbonyl carbon at 1-site), 150.2 (quaternary carbon, carbon at 4'-site of cinnamate aromatic ring), 141.6 (quaternary carbon, carbon at 2'-site of cinnamate aromatic ring), 139.2 (quaternary carbon, carbon at 5'-site of cinnamate aromatic ring), 139.0 (quaternary carbon, carbon at 1"-site of phenethyl aromatic ring), 131.7 (quaternary carbon, carbon at 2-site of propene), 130.3 (CH, carbon at 3-site of propene), 128.8 (CH, carbons at 2"- and 6"-sites of phenethyl aromatic ring), 128.7 (CH, carbons at 3"- and 5"-sites of phenethyl aromatic ring), 126.7 (CH, carbon at 4"-site of phenethyl aromatic ring), 113.7 (CH, carbon at 6'-site of cinnamate aromatic ring), 112.8 (quaternary carbon, carbon at 1'-site of cinnamate aromatic ring), 100.4 (CH, carbon at 3'-site of cinnamate aromatic ring), 56.7 (CH$_3$, methyl group carbon of methoxy group), 55.8 (CH$_3$, methyl group carbon of methoxy group), 41.0 (CH$_2$, methylene group carbon of phenethyl), 35.7 (CH$_2$, methylene group carbon of phenethyl), 14.3 (CH$_3$, methyl group carbon bound to 2-site of propene).

Synthesis of (E) N-L-glutamic acid 3-(2-amino-4,5-dimethoxyphenyl)-2-methyl-2-propenoic amide Into 80 ml of tetrahydrofuran, 0.72 g (2.0 mmol) of (E) 3-(2-amino-4,5-dimethoxyphenyl)-2-methyl-2-propenoic acid p-nitrophenyl ester was dissolved; and, with a solution in which 2.3 g (10 mmol) of L-glutamic acid had been dissolved in 160 ml of a 0.5-N aqueous sodium hydrogencarbon ate solution being added thereto, the mixture was reacted at room temperature for one night. After its pH was adjusted to 4 with 2-N hydrochloric acid being added thereto, the reaction liquid was concentrated under a reduced pressure as it was. The resulting residue was once dissolved in 30 ml of water, and then was lyophilized in order to eliminate remaining hydrochloric acid. The resulting lyophilized product was refined by a silica gel column chromatography using a moving phase of chloroform/methanol/trifluoroacetic acid at 100/10/0.01 to 40/10/0.01, and then was lyophilized, whereby 0.74 g of the aimed compound was obtained (yield: quantitative).

The structure of this compound was verified by $^1$H-NMR and $^{13}$C-NMR.

$^1$H-NMR (heavy dimethyl sulfoxide, δ ppm): 8.44 (1H, d, J=7.5 Hz, amide group proton), 7.34 (1H, s, proton at 3-site of propenoic acid), 7.24 (1H, s, proton at 3'-site of aromatic ring), 6.94 (1H, s, proton at 6'-site of aromatic ring), 4.36 (1H, ddd, J=9.3 Hz, 7.7 Hz, 5.5 Hz, methine group proton at α-site of glutamic acid portion), 4.10 (2H, bs, amino group proton), 3.82 (6H, s, methyl group proton of methoxy group),2.47 (2H, dd, J=7.5 Hz, 7.5 Hz, methylene group proton at γ-site of glutamic acid portion), 2.07 (2H, m, methylene group proton at β-site of glutamic acid portion), 1.97 (3H, s, methyl group proton bound to 2-site of propene); $^{13}$C-NMR (heavy dimethyl sulfoxide, δ ppm): 169.3, 169.1, 169.0 (quaternary carbon, carbonyl carbon in glutamic acid portion and carbonyl carbon at 1-site), 148.6 (quaternary carbon, carbon at 4'-site of aromatic ring), 147.8 (quaternary carbon, carbon at 2'-site of aromatic ring), 135.1 (quaternary carbon, carbon at 5'-site of aromatic ring), 126.9 (CH, carbon at 3-site of propene), 122.6 (quaternary carbon, carbon at 1'-site of aromatic ring), 112.8 (CH, carbon at 6'-site of aromatic ring), 107.6 (CH, carbon at 3'-site of aromatic ring), 55.8 ($CH_3$, methyl group carbon of methoxy group), 55.7 ($CH_3$, methyl group carbon of methoxy group), 51.7 (CH, methine group carbon at α-site of glutamic acid portion), 30.3 ($CH_2$, methylene group carbon at γ-site of glutamic acid portion), 26.0 ($CH_2$, methylene group carbon at 8-site of glutamic acid portion), 14.5 ($CH_3$, methyl group carbon bound to 2-site of propene).

Synthesis of (E) N-(o-di-t-butyloxy)-L-glutamic acid 3-(2-amino-4,5-dimethoxyphenyl)-2-methyl-2-propenoic amide Into 200 ml of tetrahydrofuran, 0.36 g (1.0 mmol) of (E) 3-(2-amino-4,5-dimethoxyphenyl)-2-methyl-2-propenoic acid p-nitrophenyl ester and 0.89 g (3.0 mmol) of glutamic acid di-t-butyl ester hydrochloride (manufactured by Sigma Chemical Co.) were dissolved; and the mixture was reacted for 4 hours at room temperature. The solvent was eliminated under a reduced pressure, and the residue was dissolved in ethyl acetate. The resulting solution was washed, dried on sodium sulfate anhydride, and then concentrated, whereby a crude product was obtained. This product was refined by a column chromatography (silica gel (aminopropyl-modified type) manufactured by Fuji Silysia Chem. Co., NH-DM1020 1000 g; eluent: hexane/ethyl acetate=1/1), whereby 0.48 g of the aimed compound was obtained (yield: quantitative).

The structure of this compound was verified by $^1$H-NMR and $^{13}$C-NMR.

$^1$H-NMR (heavy chloroform, δ ppm): 7.34 (1H, s, proton at 3-site of propenoic acid), 6.75 (1H, d, J=7.3 Hz, amide group proton), 6.63 (1H, s, proton at 6'-site of aromatic ring), 6.30 (1H, s, proton at 3'-site of aromatic ring), 4.59 (1H, dt, J=7.3 Hz, 4.6 Hz, methine group proton at α-site of glutamic acid portion), 3.85 (3H, s, methyl group proton of methoxy group), 3.80 (3H, s, methyl group proton of methoxy group), 3.59 (2H, bs, amino group proton), 2.39 (2H, m, methylene group proton at γ-site of glutamic acid portion), 2.25 (2H, m, methylene group proton at β-site of glutamic acid portion), 2.05 (3H, s, methyl group proton at 2-site of propene), 1.50 (9H, s, methyl group proton of butyl group), 1.45 (9H, s, methyl group proton of butyl group); $^{13}$C-NMR (heavy chloroform, δ ppm): 172.6 (quaternary carbon, carbonyl carbon in glutamic acid portion), 171.2 (carbonyl carbon in glutamic acid portion), 168.7 (quaternary carbon, carbonyl carbon at 1-site), 150.4 (quaternary carbon, carbon at 4'-site of aromatic ring), 141.6 (quaternary carbon, carbon at 2'-site of aromatic ring), 139.2 (quaternary carbon, carbon at 5'-site of aromatic ring), 131.1 (CH, carbon at 3-site of propene), 131.1 (quaternary carbon, carbon at 2-site of propene), 113.6 (CH, carbon at 6'-site of aromatic ring), 112.8 (quaternary carbon, carbon at 1'-site of aromatic ring), 100.3 (CH, carbon at 3'-site of aromatic ring), 82.4 (quaternary carbon, butyl group carbon), 80.8 (quaternary carbon, butyl group carbon), 56.7 ($CH_3$, methyl group carbon of methoxy group), 55.8 ($CH_3$, methyl group carbon of methoxy group), 52.8 (CH, methine group carbon at α-site of glutamic acid portion), 31.7 ($CH_2$, methylene group proton at γ-site of glutamic acid portion), 28.1 ($CH_3$, methyl group carbon of butyl group), 27.5 ($CH_2$, methylene group proton at β-site of glutamic acid portion), 14.2 ($CH_3$, methyl group carbon at 2-site of propene).

Synthesis of ethyl 2-methyl-3-(2-nitrophenyl)-2-propenate

Into 500 ml of benzene, 21.0 g (139.0 mmol) of 2-nitrobenzaldehyde (manufactured by Aldrich Chemical Co., Inc.) and 50.0 g (138.0 mmol) of Wittig reagent (carbethoxyethylidene triphenylphosphorane, manufactured by Aldrich Chemical Co., Inc.) were dissolved; and the mixture was stirred at room temperature for one night. After the completion of the reaction was verified by TLC, the reaction liquid was concentrated under a reduced pressure, ethanol was added thereto, and the precipitated crystal was filtered out. The filtrate was concentrated under a reduced pressure, so as to yield an oily product, which was then refined by a silica gel column chromatography (silica gel; developing solvent: ethyl acetate/hexane=1/4), whereby 32.1 g of the aimed compound were obtained as an oily product (yield: 98.2%).

The structure of this compound was determined by $^1$H-NMR and $^{13}$C-NMR.

$^1$H-NMR (heavy chloroform, δ ppm): 8.13 (d, 1H, proton at 3'-site of aromatic ring), 7.90 (s, 1H, proton at 3-site of propene), 7.66 (dd, 1H, proton at 5'-site of aromatic ring), 7.51 (dd, 1H, proton at 4'-site of aromatic ring), 7.37 (d, 1H, proton at 6'-site of aromatic ring), 4.30 (q, 2H, methylene group proton of ethyl group), 1.90 (s, 3H, methyl group proton bound to 2-site of propene), 1.36 (t, 3H, methyl proton of ethyl group); $^{13}$C-NMR (heavy chloroform, δ ppm): 167.6 (quaternary carbon, carbonyl carbon at 1-site), 147.8 (quaternary carbon, carbon at 2'-site of aromatic ring), 135.3 (CH, carbon at 3-site of propene), 133.2 (CH, carbon at 5'-site of aromatic ring), 132.0 (quaternary carbon, carbon at 1'-site of aromatic ring), 131.3 (CH, carbon at 4'-site of aromatic ring), 130.6 (quaternary carbon, carbon at 2-site of propene), 128.9 (CH, carbon at 6'-site of aromatic ring), 124.9 (CH, carbon at 3'-site of aromatic ring), 61.1 ($CH_2$, methylene group carbon of ethyl group), 14.3 ($CH_2$, methyl group carbon of ethyl group), 14.0 ($CH_3$, methyl group carbon bound to 2-site of propene).

Synthesis of (E) 2-methyl-3-(2-nitrophenyl)-2-proplenoic acid

Into 200 ml of methanol, 11.8 g (50.2 mmol) of ethyl 2-methyl-3-(2-nitrophenyl)-2-propenate were dissolved; and, with 200 ml of a 2-N aqueous sodium hydroxide solution being added thereto, the mixture was stirred at 40° C. for one night. After the completion of the reaction was verified by TLC, the reaction liquid was concentrated under a reduced pressure. After the pH was adjusted to 1 with 1-N hydrochloric acid being added thereto, the resulting solution was dissolved in ethyl acetate. After being washed three times with water, the solution was dried for one night with sodium sulfate anhydride being added thereto. After sodium sulfate was filtered out, the filtrate was concentrated under a reduced pressure, whereby 10.2 g of the aimed compound were obtained as a crystal (yield: 98.0%).

The structure of this compound was verified by $^1$H-NMR and $^{13}$C-NMR.

$^1$H-NMR (heavy dimethyl sulfoxide, δ ppm): 12.69 (bs, 1H, carboxyl group proton), 8.15 (d, 1H, proton at 3'-site of aromatic ring), 7.80 (dd, 1H, proton at 5'-site of aromatic ring), 7.76 (s, 1H, proton at 3-site of propene), 7.64 (dd, 1H, proton at 4'-site of aromatic ring), 7.53 (d, 1H, proton at 6'-site of aromatic ring), 1.82 (s, 3H, methyl group proton bound to 2-site of propene); $^{13}$C-NMR (heavy dimethyl sulfoxide, δ ppm): 168.5 (quaternary carbon, carboxyl group carbon), 147.5 (quaternary carbon, carbon at 2'-site of aromatic ring), 134.5 (CH, carbon at 3-site of propene), 133.7 (CH, carbon at 5'-site of aromatic ring), 131.3 (CH, carbon at 6'-site of aromatic ring), 130.9 (quaternary carbon, carbon at 1'-site of aromatic ring), 130.5 (quaternary carbon, carbon at 2-site of propene), 129.4 (CH, carbon at 4'-site of aromatic ring), 124.5 (CH, carbon at 3α-site of aromatic ring), 13.7 (CH$_3$, methyl group carbon bound to 2-site of propene).

Synthesis of (E) ethyl 3-(2-aminophenyl)-2-methyl-2-propenate

Into 160 ml of acetic acid, 10 g (42.5 mmol) of (E) ethyl 2-methyl-3-(2-nitrophenyl)-2-propenate were dissolved. While the solution was stirred, 10.9 g (195.2 mmol) of iron powder (Koso Chem. Co.) and 12 ml of distilled water were added thereto at room temperature; and temperature was raised, so that reflux was carried out for 1 hour at 100° C. After the end point of the reaction was verified by TLC, the reaction liquid was cooled, and acetic acid was evaporated under a reduced pressure. Ethyl acetate was added to the residue, and insoluble matters were filtered out. With water being added thereto, the filtrate was fractionated. The resulting organic layer was successively washed with water and a saturated aqueous sodium hydrogencarbon ate solution, and then was dried for one night with sodium sulfate being added thereto. After sodium sulfate anhydride was filtered out, the filtrate was concentrated under a reduced pressure; and the resulting oily product was refined by a silica gel column chromatography (silica gel; developing solvent: ethyl acetate/hexane=1/3), whereby 6.4 g of the aimed compound were obtained as an oily product (yield: 71.5%).

The structure of this compound was determined by $^1$H-NMR and $^{13}$C-NMR.

$^1$H-NMR (heavy chloroform, δ ppm): 7.60 (s, 1H, proton at 3-site of propene), 7.14 (dd, 1H, proton at 4'-site of aromatic ring), 7.10 (d, 1H, proton at 6'-site of aromatic ring), 6.77 (dd, 1H, proton at 5'-site of aromatic ring), 6.72 (d, 1H, proton at 3'-site of aromatic ring), 4.27 (q, 2H, methylene group proton of ethyl group), 3.74 (bs, 2H, amino group proton), 2.00 (s, 3H, methyl group proton bound to 2-site of propene), 1.35 (t, 3H, methyl group proton of ethyl group); $^3$C-NMR (heavy chloroform, δ ppm): 168.4 (quaternary carbon, carbonyl carbon at 1-site), 144.5 (quaternary carbon, carbon at 2'-site of aromatic ring), 134.9 (CH, carbon at 3-site of propene), 130.2 (quaternary carbon, carbon at 2-site of propene), 129.6 (CH, carbon at 4'-site of aromatic ring), 129.4 (CH, carbon at 6'-site of aromatic ring), 121.3 (quaternary carbon, carbon at 1'-site of aromatic ring), 118.1 (CH, carbon at 5'-site of aromatic ring), 115.5 (CH, carbon at 3'-site of aromatic ring), 60.8 (CH$_2$, methylene group carbon of ethyl group), 14.3 (CH$_3$, methyl group carbon of ethyl group), 14.1 (CH$_3$, methyl group carbon bound to 2-site of propene).

Synthesis of ethyl 3-(4-chloro-2-nitrophenyl)- 2-methyl-2-propenate

In 200 ml of benzene, 10.0 g (53.8 mmol) of 4-chlorobenzaldehyde (manufactured by Aldrich Chemical Co., Inc.) and 18.1 g (50.0 mmol) of Wittig reagent (carbethoxyethylidene triphenylphosphorane, manufactured by Aldrich Chemical Co., Inc.) were stirred at ordinary temperature for one night. After the completion of the reaction was verified by TLC, the reaction liquid was concentrated, whereby a crude product was obtained. This product was refined by a column chromatography (aminopropyl-modified silica gel (Fuji Silysia Chem. Co., NH-DM); developing solvent: hexane/ethyl acetate=1/1), whereby 13.1 g of the aimed compound were obtained as a crystal (yield: 97%).

The structure of this compound was determined by $^1$H-NMR and $^{13}$C-NMR.

$^1$H-NMR (heavy chloroform, δ ppm): 8.14 (s, 1H, proton at 3'-site of aromatic ring), 7.82 (s, 1H, proton at 3-site of propene), 7.64 (d, 1H, proton at 5'-site of aromatic ring), 7.32 (d, 1H, proton at 6'-site of aromatic ring), 4.29 (q, 2H, methylene group proton of ethyl group), 1.90 (s, 3H, methyl group proton bound to 2-site of propene), 1.36 (t, 3H, methyl group proton of ethyl group); $^{13}$C-NMR (heavy chloroform, δ ppm): 167.4 (quaternary carbon, carbonyl carbon at 1-site), 148.0 (quaternary carbon, carbon at 2'-site of aromatic ring), 134.8 (quaternary carbon, carbon at 4'-site of aromatic ring), 134.1 (CH, carbon at 3-site of propene), 133.4 (CH, carbon at 5'-site of aromatic ring), 132.5 (CH, carbon at 6'-site of aromatic ring), 131.3 (quaternary carbon, carbon at 1'-site of aromatic ring), 130.3 (quaternary carbon, carbon at 2-site of propene), 125.1 (CH, carbon at 3'-site of aromatic ring), 61.3 (CH$_2$, methylene group carbon of ethyl group), 14.3 (CH$_3$, methyl group carbon of ethyl group), 14.1 (CH$_3$, methyl group carbon bound to 2-site of propene).

Synthesis of (E) ethyl 3-(2-amino-4-chlorophenyl)-2-methyl-2-propenate

Into 170 ml of acetic acid, 11.0 g of ethyl 3-(4-chloro-2-nitrophenyl)-2-methyl-2-propenate were C) dissolved; and, while the mixture was stirred, 10.9 g (195.2 mmol) of iron powder (Koso Chem. Co.) and 13 ml of distilled water were added thereto at room temperature. The temperature of the mixture was raised, so that the reaction was carried out at 97° C. for 2 hours. After the end point of the reaction was verified by TLC, the reaction liquid was cooled, and acetic acid was evaporated under a reduced pressure. To the residue, 300 ml of water and 400 ml of ethyl acetate were added. Then, insoluble matters were filtered out. The filtrate was successively washed with water, an aqueous sodium hydrogencarbon ate solution, and a saturated aqueous sodium chloride solution; and then was dried for one night with sodium sulfate being added thereto. After sodium sulfate was filtered out, the filtrate was concentrated under a reduced pressure, whereby 9.8 g of a crude crystal were obtained. This crystal was refined by a silica gel column chromatography (aminopropyl-modified silica gel (Fuji Silysia Chem. Co., NH-DM1020); developing solvent: hexane/ethyl acetate=2/1), whereby 7.2 g of the aimed compound were obtained (yield: 73.3%).

The structure of this compound was determined by $^1$H-NMR and $^{13}$C-NMR.

$^1$H-NMR (heavy chloroform, δ ppm): 7.50 (s, 1H, proton at 3-site of propene), 7.01 (d, 1H, proton at 6'-site of aromatic ring), 6.73 (d, 1H, proton at 5'-site of aromatic ring), 6.72 (s, 1H, proton at 3'-site of aromatic ring), 4.27 (q, 2H, methylene group proton of ethyl group), 3.68 (bs, 2H, amino group proton), 1.98 (s, 3H, methyl group proton bound to 2-site of propene), 1.35 (t, 3H, methyl group proton of ethyl group); $^{13}$C-NMR (heavy chloroform, δ ppm): 168.2 (quaternary carbon, carbonyl carbon at 1-site), 145.6 (quaternary carbon, carbon at 2'-site of aromatic ring), 134.9

(quaternary carbon, carbon at 4'-site of aromatic ring), 133.8 (CH, carbon at 3-site of propene), 130.9 (quaternary carbon, carbon at 2-site of propene), 130.7 (CH, carbon at 6'-site of aromatic ring), 119.6 (quaternary carbon, carbon at 1'-site of aromatic ring), 118.2 (CH, carbon at 5'-site of aromatic ring), 115.2 (CH, carbon at 3'-site of aromatic ring), 61.0 ($CH_2$, methylene group carbon of ethyl group), 14.3 ($CH_3$, methyl group carbon of ethyl group), 14.2 ($CH_3$, methyl group carbon bound to 2-site of propene).

Synthesis of ethyl 3-(5-chloro-2-nitrophenyl)-2-methyl-2-propenate (FIG. 4A)

To 200 ml of benzene, 10.0 g (53.8 mmol) of 5-chloro-2-nitrobenzaldehyde (manufactured by Aldrich Chemical Co., Inc.) and 18.1 g (50.0 mmol) of Wittig reagent (carbethoxyethylidene triphenylphosphorane, manufactured by Aldrich Chemical Co., Inc.) were added, and the mixture m was stirred at room temperature for one night. After the completion of the reaction was verified by TLC, the reaction liquid was concentrated, whereby a crude product was obtained. This crude product was refined by a column chromatography (aminopropyl-modified silica gel (Fuji Silysia Chem. Co., NH-DM); developing agent: hexane/ethyl acetate=1/1), whereby 13.3 g of the aimed compound were obtained as a crystal (yield: 98%).

The structure of this compound was determined by $^1$H-NMR and $^{13}$C-NMR.

$^1$H-NMR (heavy chloroform, δ ppm): 8.11 (d, 1H, proton at 3'-site of aromatic ring), 7.83 (s, 1H, proton at 3-site of propene), 7.47 (d, 1H, proton at 4'-site of aromatic ring), 7.34 (s, 1H, proton at 6'-site of aromatic ring), 4.30 (q, 2H, methylene group proton of ethyl group), 1.91 (s, 3H, methyl group proton bound to 2-site of propene), 1.35 (t, 3H, methyl group proton of ethyl group); $^{13}$C-NMR (heavy chloroform, δ ppm): 167.3 (quaternary carbon, carbonyl carbon at 1-site), 146.1 (quaternary carbon, carbon at 2'-site of aromatic ring), 139.8 (quaternary carbon, carbon at 5'-site of aromatic ring), 134.1 (CH, carbon at 3-site of propene), 133.8 (quaternary carbon, carbon at 1'-site of aromatic ring), 131.4 (quaternary carbon, carbon at 2-site of propene), 131.1 (CH, carbon at 6'-site of aromatic ring), 129.0 (CH, carbon at 4'-site of aromatic ring), 126.4 (CH, carbon at 3'-site of aromatic ring), 61.3 ($CH_2$, methylene group carbon of ethyl group), 14.2 ($CH_3$, methyl group carbon of ethyl group), 14.0 ($CH_3$, methyl group carbon bound to 2-site of propene).

Synthesis of (E) ethyl 3-(2-amino-5-chlorophenyl)-2-methyl-2-propenate

Into 170 ml of acetic acid, 11.0 g (41.0 mmol) of ethyl 3-(5-chloro-2-nitrophenyl)-2-methyl-2-propenate were dissolved. After 10.9 g (195.2 mmol) of iron powder (Koso Chem. Co.) and 13 ml of distilled water were added thereto while the mixture was stirred at room temperature, temperature was raised, so as to carry out a reaction for 2 hours at 97° C. After the end point of the reaction was verified by TLC, the reaction liquid was cooled, and acetic acid was evaporated under a reduced pressure. To the residue, 300 ml of water and 400 ml of ethyl acetate were added; and insoluble matters were filtered out. The filtrate was successively washed with water, an aqueous sodium hydrogencarbon ate solution, and a saturated aqueous sodium chloride solution; and then was dried for one night with sodium sulfate being added thereto. After sodium sulfate was filtered out, the filtrate was concentrated under a reduced pressure, whereby 9.8 g of an oily crude product were obtained. This product was refined by a column chromatography (aminopropyl-modified silica gel (Fuji Silysia Chem. Co., NH-DM1020); developing solvent: hexane/ethyl acetate=2/1), whereby 7.2 g of the aimed compound were obtained as an oily product (yield: 73.3%).

The structure of this compound was determined by $^1$H-NMR and $^{13}$C-NMR.

$^1$H-NMR (heavy chloroform, δ ppm): 7.49 (s, 1H, proton at 3-site of propene), 7.07 (d, 1H, proton at 4'-site of aromatic ring), 7.05 (s, 1H, proton at 61-site of aromatic ring), 6.64 (d, 1H, proton at 3'-site of aromatic ring), 4.27 (q, 2H, methylene group proton of ethyl group), 3.74 (bs, 2H, amino group proton), 1.99 (s, 3H, methyl group proton bound to 2-site of propene), 1.35 (t, 3H, methyl group proton of ethyl group); $^{13}$C-NMR (heavy chloroform, δ ppm): 168.0 (quaternary carbon, carbonyl carbon at 1-site), 143.2 (quaternary carbon, carbon at 2'-site of aromatic ring), 133.6 (CH, carbon at 3-site of propene), 131.4 (quaternary carbon, carbon at 2-site of propene), 129.1 (CH, carbon at 4'- or 6'-site of aromatic ring), 128.9 (CH, carbon at 4'- or 6'-site of aromatic ring), 122.6 (quaternary carbon, carbon at 1'- or 5'-site of aromatic ring), 122.5 (quaternary carbon, carbon at 1'- or 5'-site of aromatic ring), 116.7 (CH, carbon at 3'-site of aromatic ring), 61.0 ($CH_2$, methylene group carbon of ethyl group), 14.3 ($CH_3$, methyl group carbon of ethyl group), 14.2 ($CH_3$, methyl group carbon bound to 2-site of propene).

Synthesis of (E) 3-(2-amino-benzo[d]phenyl)-2-methyl-2-propenoic acid ethyl ester Into 30 ml of benzene, 2.0 g (7 mmol) of 3-(2-nitro-benzo[d]phenyl) -2-methyl-2-propenoic acid ethyl ester were dissolved; and, with 1.73 g of iron powder (Koso Chem. Co.) and 2.5 ml of distilled water being added thereto under stirring at room temperature, temperature was raised, so that the mixture was heated to 70° C. After a reaction of 1.5 hours, insoluble matters were filtered out. The filtrate was added to 100 ml of water, and then was extracted twice with 100 ml of ethyl acetate. The resulting ethyl acetate solution was successively washed with water, an aqueous sodium hydrogencarbon ate solution, and a saturated aqueous sodium chloride solution. The washed product was dried on sodium sulfate anhydride and concentrated, whereby an oily product was obtained. This product was refined by a silica gel column chromatography (silica gel; developing solvent: ethyl acetate/hexane=1/5), whereby 1.4 g of the aimed compound were obtained as an oily product (yield: 77%).

The structure of this compound was verified by $^1$H-NMR and $^{13}$C-NMR.

$^1$H-NMR (heavy chloroform, δ ppm): 7.73 (1H, s, proton at 3-site of propene), 7.70–7.58 (2H, m, protons at 4'- and 7'-sites of aromatic ring), 7.58 (1H, s, proton at 8'-site of aromatic ring), 7.40–7.20 (2H, m, protons at 5'- and 6'-sites of aromatic ring), 7.04 (1H, s, proton at 3'-site of aromatic ring), 4.31 (2H, q, J=7 Hz, methylene group proton of ethyl group), 3.89 (2H, bs, amino group proton), 2.06 (3H, s, methyl group proton bound to 2-site of propene), 1.37 (3H, t, J=7 Hz, methyl group proton of ethyl group) $^{13}$C-NMR (heavy chloroform, δ ppm): 168.2 (quaternarycarbon, carbonyl carbon at 1-site), 142.6 (quaternary carbon, carbon at 2'-site of aromatic ring), 134.8 (CH, carbon at 3-site of propene), 134.7 (quaternary carbon, carbon at 3a'-site of aromatic ring), 131.6 (quaternary carbon, carbon at 2-site of propene), 129.2 (CH, carbon at 5'- or 6'-site of aromatic ring), 127.9 (CH, carbon at 5'- or 6'-site of aromatic ring), 127.5 (quaternary carbon, carbon at 7a'-site of aromatic ring), 126.8 (CH, carbon at 4'- or 7'-site of aromatic ring), 125.5 (CH, carbon at 4'- or 7'-site of aromatic ring), 124.8 (quaternary carbon, carbon at 1'-site of aromatic ring), 122.9 (CH, carbon at 8'-site of aromatic ring), 109.2 (CH, carbon at 3'-site of aromatic ring), 61.0 ($CH_2$, methylene group carbon of ethyl group), 14.4 ($CH_3$, methyl group carbon of ethyl group), 14.3 ($CH_3$, methyl group carbon bound to 2-site of propene).

Synthesis of 4-dimethylamino-2-nitrobenzaldehyde

In a nitrogen atmosphere, 51 g (0.33 mol) of phosphorus oxychloride (manufactured by Wako Pure Chemical Industries, Ltd.) were added dropwise to 88 ml of cooled dimethylformaldehyde (DMF). The dropping rate was adjusted so as to keep a temperature of 2° C. to 4° C. at the time of dropping, and stirring was further continued for 30 minutes at 2° C. after the completion of dropping. To this mixture, a 70-ml dimethylformamide solution of 54.8 g (0.33 mol) of N,N-dimethyl-3-nitroaniline (manufactured by Tokyo Kasei Kogyo Co., Ltd.) was added dropwise such that the reaction temperature does not exceed 5° C.; and the mixture was stirred for 2 hours as it was. Thereafter, temperature was gradually raised, and the mixture was stirred at 60° C. for one night. After being cooled to room temperature, the reaction liquid was poured into vigorously stirred 500 ml of ice water. The pH of the mixture was adjusted to about 8 with sodium acetate being added thereto, and the precipitated crystal was filtered out and dried, whereby 50.2 g of a crude product were obtained. This product was recrystallized from acetone/normal hexane, whereby 21 g of the aimed product were obtained (yield: 33%).

The structure of this compound was verified by $^1$H-NMR and $^{13}$C-NMR.

$^1$H-NMR (heavy chloroform, δ ppm): 10.12 (1H, s, formyl group proton), 7.91 (1H, d, J=9 Hz, proton at 6-site), 7.10 (1H, s, proton at 3-site), 6.85 (1H, d, J=9 Hz, proton at 5-site), 3.15 (6H, s, dimethylamino group proton); $^{13}$C-NMR (heavy chloroform, δ ppm): 186.7 (CH, formyl group), 153.6 (quaternary carbon, carbon at 4-site), 152.7 (quaternary carbon, carbon at 2-site), 131.4 (CH, carbon at 6-site), 117.5 (quaternary carbon, carbon at 1-site), 114.3 (CH, carbon at 5-site), 105.8 (CH, carbon at 3-site), 40.4 ($CH_3$, methyl group carbon of dimethylamino group).

Synthesis of (E) ethyl 3-(4-dimethylamino-2-nitrophenyl)-2-methyl-2-propenate Into 250 ml of benzene, 20.0 g (0.10 mol) of 4-dimethylamino-2-nitrobenzaldehyde and 36.2 g (0.10 mol) of carbethoxyethylidene triphenylphosphorane (manufactured by Aldrich Chemical Co., Inc.) were dissolved, and the mixture was stirred at room temperature for one night. The solvent was evaporated under a reduced pressure, whereby 58 g of a crude product was obtained. This product was refined by a column chromatography (aminopropylated silica gel: Fuji Silysia Chem. Co., NH-DM1020), whereby 20.8 g of the aimed compound were obtained as a crystal (yield: 74.7%).

The structure of this compound was verified by $^1$H-NMR and $^{13}$C-NMR.

$^1$H-NMR (heavy chloroform, δ ppm): 7.81 (1H, s, proton at 3-site of propenoic acid), 7.33 (1H, s, proton at 3'-site of aromatic ring), 7.23 (1H, d, J=9 Hz, proton at 6'-site of aromatic ring), 6.86 (1H, d, J=9 Hz, proton at 5'-site of aromatic ring), 4.27 (2H, q, J=7 Hz, methylene group proton of ethyl group), 3.06 (6H, s, methyl group proton of dimethylamino group), 1.96 (3H, s, methyl group proton bound to 2-site of propene), 1.34 (3H, t, J=7 Hz, methyl group proton of ethyl group); $^{13}$C-NMR (heavy chloroform, δ ppm): 168.2 (quaternary carbon, carbonyl carbon at 1-site), 150.2 (quaternary carbon, carbon at 2'-site of aromatic ring), 149.1 (quaternary carbon, carbon at 4'-site of aromatic ring), 135.7 (CH, carbon at 3-site of propenoic acid), 132.0 (CH, carbon at 6'-site of aromatic ring), 128.2 (quaternary carbon, carbon at 2-site of propene), 118.0 (quaternary carbon, carbon at 1'-site of aromatic ring), 115.7 (CH, carbon at 5'-site of aromatic ring), 107.0 (CH, carbon at 3'-site of aromatic ring), 60.8 ($CH_2$, methylene group carbon of ethyl group), 40.2 ($CH_3$, methyl group carbon of dimethylamino group), 14.3 ($CH_3$, methyl group carbon of ethyl group), 14.1 ($CH_3$, methyl group carbon bound to 2-site of propene).

Synthesis of (E) ethyl 3-(2-amino-4-dimethylaminophenyl)-2-methyl-2-propenate In a dark room, 20.5 q (0.07 mol) of (E) ethyl 3-(4-dimethylamino-2-nitrophenyl)-2-methyl-2-propenate, 33.4 g (0.33 mol) of triethylamine (manufactured by Wako Pure Chemical Industries, Ltd.), and 2.1 g of 10% Pd/C were dissolved in 200 ml of acetonitrile, and 13.8 g (0.30 mol) of formic acid (manufactured by Wako Pure Chemical Industries, Ltd.) were added dropwise thereto at room temperature. Along with the dropping, the reaction temperature rose up to 45° C. After the completion of dropping, the reaction liquid was heated to 60° C. and was stirred for 1 hour. After the completion of the reaction was verified by TLC, the reaction liquid was cooled to room temperature, insoluble matters were filtered out, the filtrate was concentrated under a reduced pressure, and thus obtained product was dissolved in 400 ml of ethyl acetate. The resulting solution was successively washed with water, a saturated aqueous sodium hydrogencarbon ate solution, and a saturated aqueous sodium chloride solution; and was further dried with sodium sulfate anhydride. Thus dried product was concentrated under a reduced pressure, whereby 17.4 g of a crude product were obtained. This product was further recrystallized from normal hexane/ethyl acetate, whereby 4.67 g of the aimed compound were obtained (yield: 27%).

The structure of this compound was verified by $^1$H-NMR and $^{13}$C-NMR.

$^1$H-NMR (heavy chloroform, δ ppm): 7.60 (1H, s, proton at 3-site of propenoic acid), 7.08 (1H, d, J=9 Hz, proton at 6'-site of aromatic ring), 6.19 (1H, d, J=8 Hz, proton at 5'-site of aromatic ring), 6.01 (1H, s, proton at 3'-site of aromatic ring), 4.23 (2H, q, J=7 Hz, methylene group proton of ethyl group), 3.74 (2H, bs, aniline-type amino group proton), 2.94 (6H, s, methyl group proton of dimethylamino group), 2.04 (3H, s, methyl group proton bound to 2-site of propene), 1.31 (3H, t, J=7 Hz, methyl group proton of ethyl group); $^{13}$C-NMR (heavy chloroform, δ ppm): 169.1 (quaternary carbon, carbonyl carbon at 1-site), 151.7 (quaternary carbon, carbon at 2'-site of aromatic ring), 146.2 (quaternary carbon, carbon at 4'-site of aromatic ring), 134.7 (CH, carbon at 3-site of propenoic acid), 130.9 (CH, carbon at 6'-site of aromatic ring), 125.7 (quaternary carbon, carbon at 2-site of propene), 110.4 (quaternary carbon, carbon at 1'-site of aromatic ring), 103.3 (CH, carbon at 5'-site of aromatic ring), 98.5 (CH, carbon at 3'-site of aromatic ring), 60.5 ($CH_2$, methylene group carbon of ethyl group), 40.2 ($CH_3$, methyl group carbon of dimethylamino group), 14.4 ($CH_3$, methyl group carbon of ethyl group), 14.4 ($CH_3$, methyl group carbon bound to 2-site of propene).

Synthesis of (E) 3-(4-dimethylamino-2-nitrophenyl)-2-methyl-2-propenoic acid Into 150 ml of methanol, 15.0 g (53.9 mmol) of (E) ethyl 3-(4-dimethylamino-2-nitrophenyl)-2-methyl-2-propenate were dissolved; and, with 3.2 g (80 mmol) of sodium hydroxide being added thereto, the mixture was stirred at 45° C. for 5.5 hours. After the solvent was evaporated from the reaction liquid under a reduced pressure, the residue was dissolved in 100 ml of water. Thus obtained solution was adjusted to neutral with 2-N hydrochloric acid being added thereto. The precipitated crystal was filtered out, fully washed with water, and then dried, whereby 12.1 g of the aimed compound were obtained as a crystal (yield: 89.7%).

The structure of this compound was verified by $^1$H-NMR.

$^1$H-NMR (heavy chloroform, δ ppm): 7.93 (1H, s, proton at 3-site of propenoic acid), 7.33 (1H, d, J=9 Hz, proton at 6'-site of aromatic ring), 7.24 (1H, d, J=8 Hz, proton at 5'-site of aromatic ring), 6.87 (1H, s, proton at 3'-site of aromatic ring), 3.05 (6H, s, methyl group proton of dimethylamino group), 1.97 (3H, s, methyl group proton bound to 2-site of propene).

Synthesis of (E) 3-(4,5-dimethoxy-2-methylaminophenyl)-2-methyl-2-propenoic acid In a dark room, 3.0 g (11.3 mmol) of (E) 3-(2-amino-4,5-dimethoxyphenyl)-2-methyl-2-propenoic acid ethyl ester and 18 ml of trifluoroacetic acid anhydride (manufactured by Wako Pure Chemical Industries, Ltd.) were mixed, and the mixture was stirred at room temperature for one night. Unreacted trifluoroacetic acid anhydride and trifuloroacetic acid were evaporated under a reduced pressure, whereby 3.8 g of (E) 3-[4,5-dimethoxy-2-(N-trifluoroacetyl) aminophenyl]-2-methyl-2-propenoic acid ethyl ester were obtained. Thus obtained product was dissolved in tetrahydrofuran; and, with 8 ml of methyl iodide (manufactured by Wako Pure Chemical Industries, Ltd.) and 1.1 g of potassium carbon ate (manufactured by Wako Pure Chemical Industries, Ltd.) being added thereto, the solution was refluxed for one night. After the completion of the reaction was verified by TLC, the reaction liquid was concentrated under a reduced pressure, whereby a crude product was obtained. This product was refined by a silica gel column chromatography (silica gel (amino-modified type) Fuji Silysia Chem. Co., NH-DM1020; solvent: normal hexane/ethyl acetate=4/1), whereby 3.7 g of (E) 3-[4,5-dimethoxy-2-(N-methyl-N-C) trifluoroacetyl)aminophenyl]-2-methyl-2-propenoic acid ethyl ester were obtained. This product was further dissolved in dioxane; and, with 50 m of a 2-N aqueous sodium hydroxide solution being added thereto, the mixture was reacted at 40° C. for one night. The reaction liquid was concentrated under a reduced pressure, and then was applied to a column using a solid-phase extraction filler DIAION HP-20 (manufactured by Mitsubishi Chemical Corp.) in order to eliminate excess alkalis and impurity salts, so as to be desalted as being eluted with water. Subsequently, it was eluted with methanol, and the resulting product was lyophilized, whereby 2.3 g of the aimed product were obtained (yield: 75%).

The structure of this compound was verified by $^1$H-NMR and $^{13}$C-NMR.

$^1$H-NMR (heavy methanol, δ ppm): 7.13 (1H, s, proton at 3-site of propenoic acid portion), 6.73 (1H, s, proton at 6'-site of aromatic ring), 6.30 (1H, s, proton at 3'-site of aromatic ring), 3.85 (3H, s, methyl group proton of methoxy group), 3.73 (3H, s, methyl group proton of methoxy group), 2.81 (3H, s, methyl group proton bound to aniline-type amino group), 1.94 (3H, s, methyl group proton bound to 2-site of propenoic acid portion); $^{13}$C-NMR (heavy methanol, δ ppm): 178.4 (quaternary carbon, carbonyl carbon at 1-site of propenoic acid), 151.6 (quaternary carbon, carbon at 4'-site of aromatic ring), 144.8 (quaternary carbon, carbon at 5'-site of aromatic ring), 141.1 (quaternary carbon, carbon at 2'-site of aromatic ring), 136.6 (quaternary carbon, carbon at 2-site of propenoic acid portion), 130.3 (CH, carbon at 3-site of propenoic acid portion), 117.1 (CH, carbon at 6'-site of aromatic ring), 115.7 (quaternary carbon, carbon at 1'-site of aromatic ring), 97.2 (CH, carbon at 3'-site of aromatic ring), 58.1 (CH$_3$, methyl group carbon of methoxy group), 56.4 (CH$_3$, methyl group carbon of methoxy group), 31.3 (CH$_3$, methyl group carbon bound to aniline-type amino group), 15.6 (CH$_3$, methyl group carbon bound to 2-site of propenoic acid portion).

Synthesis of (E) N-L-glutamic acid 3-(4,5-dimethoxy- 2-methylaminophenyl)-2-methyl-2-propenoic amide In a dark room, 500 mg (1.83 mmol) of (E) 3-(4,5-dimethoxy-2-methylaminophenyl)-2-methyl-2-propenoic acid were dissolved in dimethylformamide; and, with 247 mg (1.83 mmol) of 1-hydroxybenzotriazole monohydrate (HOBt.H$_2$O) (manufactured by Kokusan Chemical Works), 438 mg (1.83 mmol) of L-glutamic acid diethyl ester hydrochloride (manufactured by Kokusan Chemical Works), and 377 g (1.83 mmol) of N,N'-dicyclohexyl carbodiimide (DCC) (manufactured by Wako Pure Chemical Industries, Ltd.) being added thereto, the mixture was stirred at room temperature for one night in a nitrogen atmosphere. After the completion of the reaction, the precipitate was filtered out, and the filtrate was concentrated under a reduced pressure. The resulting residue was dissolved in ethyl acetate. Thus obtained organic layer was successively washed with a saturated aqueous sodium hydrogencarbon ate solution, a 20% aqueous citric acid solution, the saturated sodium hydrogencarbon ate solution, and a saturated aqueous sodium chloride solution. Thus washed product was dried with magnesium sulfate anhydride, and then was concentrated, whereby a crude product was obtained. This product was refined by a column chromatography (silica gel (amino-modified type): Fuji Silysia Chem. Co., NH-DM1020; eluent: normal hexane/ethyl acetate=9/1), whereby 700 mg of (E) N-L-glutamic acid diethyl ester 3-(4,5-dimethoxy- 2-methylaminophenyl)-2-methyl-2-propenoic amide were obtained. This product was further dissolved in dioxane; and, with 3 ml of a 2-N aqueous sodium hydroxide solution being added thereto, the mixture was stirred for one night. After the completion of the reaction was verified, the reaction liquid was concentrated under a reduced pressure, and then was applied to a column using a solid-phase extraction filler DIAION HP-20 (manufactured by Mitsubishi Chemical Corp.) in order to eliminate excess alkalis and impurity salts, so as to be desalted as being eluted with water. Subsequently, it was eluted with a 10% aqueous methanol solution, and the resulting product was lyophilized, whereby 350 mg of the aimed product were obtained (yield: 41%).

The structure of this compound was verified by $^1$H-NMR and $^{13}$C-NMR.

$^1$H-NMR (heavy methanol, δ ppm): 7.19 (1H, s, proton at 3-site of propenoic acid), 6.75 (1H, s, proton at 6'-site of aromatic ring), 6.31 (1H, s, proton at 3'-site of aromatic ring), 4.33 (1H, dd, J=8.0 Hz, J=4.0 Hz, methine group proton at α-site of glutamic acid portion), 3.87 (3H, s, methyl group proton of methoxy group), 3.75 (3H, s, methyl group proton of methoxy group), 2.83 (3H, s, methyl group proton bound to aniline-type amino group), 2.40–2.22 (2H, m, methylene group proton at γ-site of glutamic acid portion), 2.20–2.06 (2H, m, methylene group at β-site of glutamic acid portion), 2.03 (3H, s, methyl group proton bound to 2-site of propene); $^{13}$C-NMR (heavy methanol, δ ppm): 182.3 (quaternary carbon, carbonyl carbon in glutamic acid portion), 179.3 (quaternary carbon, carbonyl carbon in glutamic acid portion), 171.8 (quaternary carbon, carbonyl carbon at 1-site of propenoic acid), 152.1 (quaternary carbon, carbon at 4'-site of aromatic ring), 145.1 (quaternary carbon, carbon at 5'-site of aromatic ring), 140.8 (quaternary carbon, carbon at 2'-site of aromatic ring), 132.8 (quaternary carbon, carbon at 2-site of propene), 131.0 (CH, carbon at 3-site of propene), 117.0 (CH, carbon at 6'-site of aromatic ring), 114.1 (quaternary carbon, carbon at 1'-site of aromatic ring), 96.9 (CH, carbon at 31-site of aromatic ring), 58.1 (CH$_3$, methyl group carbon of methoxy group), 57.2 (CH, methine group carbon at α-site of glutamic acid portion), 56.3 (CH$_3$, methyl group carbon of methoxy group), 35.8 (CH$_2$, methylene group carbon at γ-site of glutamic acid portion), 31.2 (CH$_3$, methyl group bound to aniline-type amino group), 30.5 (CH$_2$, methylene group at β-site of glutamic acid portion), 14.6 (CH$_3$, methyl group carbon bound to 2-site of propene).

Synthesis of 6,7-dimethoxy-3-methyl-carbostyril

Into 30 ml of ethyl alcohol, 0.5 g of 3-(2-amino-4,5-dimethoxyphenyl)-2-methyl-2-propenoic acid ethyl ester was dissolved. This solution was irradiated with ultraviolet rays at 365 nm for about 20 hours, and the precipitated crystal was filtered out. This crystal was recrystallized from ethanol, whereby 0.38 g of the aimed compound was obtained (yield: 92%).

The structure of this compound was determined by infrared absorption spectrum (IR), $^1$H-NMR, $^{13}$C-NMR, TOF-MS, and the like.

IR: 1654 cm$^{31\ 1}$ (lactam); TOF-MS: 219 (M/C); $^1$H-NMR (heavy chloroform, δ ppm): 12.3 (1H, bs, amide group proton), 7.56 (1H, s, proton at 4-site), 6.90 (1H, s, proton at 8-site), 6.88 (1H, s, proton at 5-site), 3.99 (3H, s, w methyl group proton of methoxy group), 3.92 (3H, s, methyl group proton of methoxy group), 2.28 ppm (3H, s, methyl group proton bound to 3-site); $^{13}$C-NMR (heavy chloroform, δ ppm): 164.5 (quaternary carbon, carbonyl group carbon at 2-site), 151.5 (quaternary carbon, carbon at 3-site), 145.7 (quaternary carbon, carbon at 7-site), 137.1 (CH, carbon at 4-site), 133.2 (quaternary carbon, carbon at 8a-site), 126.9 (quaternary carbon, carbon at 6-site), 133.7 (quaternary carbon, carbon at 4a-site), 107.4 (CH, carbon at 5-site), 98.0 (CH, carbon at 8-site), 56.2 (CH$_3$, methyl group of methoxy group), 16.6 (CH$_3$, methyl group carbon bound to 3-site).

Synthesis of 3-methyl-benzo[g]carbostyril

In a 50-ml Erlenmeyer flask made of quartz, 0.5 g of (E) ethyl 3-(2-amino-benzo[d]phenyl)-2-methyl-2-propenoic acid ethyl ester was dissolved in 20 ml of ethanol; and, while being stirred, the mixture was irradiated with ultraviolet rays at 365 nm for 48 hours. The reaction liquid was concentrated under a reduced pressure, and the resulting crude crystal was recrystallized from ethanol, whereby the aimed compound was obtained.

The structure of this compound was determined by a $^1$H-NMR.

$^1$H-NMR (heavy chloroform, δ ppm): 8.08 (1H, s, proton at 4-site), 7.90 (1H, d, J=8 Hz, 6- or 9-site), 7.82 (1H, d, J=8 Hz, 6- or 9-site), 7.80 (1H, s, proton at 5-site), 7.66 (1H, s, proton at 10-site), 7.46 (1H, dd, J=8 Hz, proton at 7- or 8-site), 7.36 (1H, dd, J=8 Hz, proton at 7- or 8-site), 2.19 (3H, s, methyl group bound to 4-site).

Synthesis of 3-methylcarbostyril

Into 10 ml of ethanol, 0.5 g of (E) ethyl 3-(2-aminophenyl)-2-methyl-2-propenate was dissolved; and, while being stirred, the mixture was irradiated with ultraviolet rays at 256 nm for 48 hours. The reaction liquid was concentrated under a reduced pressure, and the resulting crude crystal was recrystallized from ethanol, whereby the aimed compound was obtained.

The structure of this compound was determined by $^1$H-NMR and $^{13}$C-NMR.

$^1$H-NMR (heavy dimethyl sulfoxide, δ ppm): 11.72 (bs, 1H, amide group proton at 1-site), 7.72 (s, 1H, proton at 4-site), 7.54 (d, 1H, proton at 5-site), 7.39 (dd, 1H, proton at 7-site), 7.28 (d, 1H, proton at 8-site), 7.12 (dd, proton at 6-site), 2.10 (s, 3H, methyl group proton bound to 3-site); $^{13}$C-NMR (heavy dimethyl sulfoxide; δ ppm): 162.3 (quaternary carbon, carbonyl group at 2-site), 137.8 (quaternary carbon, carbon at 9-site), 136.1 (CH, carbon at 4-site), 129.7 (quaternary carbon, carbon at 3-site), 128.8 (CH, carbon at 7-site), 126.7 (CH, carbon at 5-site), 121.4 (CH, carbon at 6-site), 119.3 (quaternary carbon, carbon at 10-site), 114.6 (CH, carbon at 8-site), 16.4 (CH$_3$, methyl group proton bound to 3-site).

Synthesis of 7-chloro-3-methylcarbostyril

In a 50-ml Erlenmeyer flask made of quartz, 10 ml of (E) ethyl 3-(2-amino-4-chlorophenyl)-2-methyl-2-propenate were dissolved in 10 ml of ethanol; and, while being stirred, the mixture was irradiated with ultraviolet rays at 256 nm for 72 hours. The reaction liquid was concentrated under a reduced pressure, and the resulting crude crystal was recrystallized from ethanol, whereby the aimed compound was obtained.

The structure of this compound was determined by $^1$H-NMR and $^{13}$C-NMR.

$^1$H-NMR (heavy dimethyl sulfoxide, δ ppm): 11.80 (bs, 1H, amide group proton at 1-site), 7.71 (s, 1H, proton at 4-site), 7.55 (d, 1H, proton at 5-site), 7.30 (s, 1H, proton at 8-site), 7.13 (d, 1H, proton at 6-site), 2.10 (s, 3H, methyl group proton bound to 3-site); $^{13}$C-NMR (heavy dimethyl sulfoxide, δ ppm): 162.3 (quaternary carbon, carbonyl group carbon at 2-site), 138.8 (quaternary carbon, carbon at 8a-site), 135.6 (CH, carbon at 4-site), 133.5 (quaternary carbon, carbon at 7-site), 130.2 (quaternary carbon, carbon at 4a-site), 128.4 (CH, carbon at 5-site), 121.6 (CH, carbon at 6-site), 118.2 (quaternary carbon, carbon at 3-site), 114.1 (CH, carbon at 8-site), 16.5 (CH$_3$, methyl group proton bound to 3-site).

Synthesis of 6-chloro-3-methylcarbostyril

In a 50-ml Erlenmeyer flask made of quartz, 0.5 g of (E) ethyl 3-(2-amino-5-chlorophenyl)-2-methyl-2-propenate was dissolved in 10 ml of ethanol; and, while being stirred, the mixture was irradiated with ultraviolet rays at 256 nm for 72 hours. The reaction liquid was concentrated under a reduced pressure, and the resulting crude crystal was recrystallized from ethanol, whereby the aimed compound was obtained.

The structure of this compound was determined by $^1$H-NMR and $^{13}$C-NMR.

$^1$H-NMR (heavy dimethyl sulfoxide, δ ppm): 11.86 (bs, 1H, amide group proton at 1-site), 7.72 (s, 1H, proton at 4-site), 7.65 (s, 1H, proton at 5-site), 7.43 (d, 1H, proton at 7-site), 7.28 (d, 1H, proton at 8-site), 2.10 (s, 3H, methyl group proton bound to 3-site); $^{13}$C-NMR (heavy dimethyl sulfoxide, δ ppm): 162.2 (quaternary carbon, carbonyl group carbon at 2-site), 136.4 (quaternary carbon, carbon at 8α-site), 135.1 (CH, carbon at 4-site), 131.4 (quaternary carbon, carbon at 6-site), 128.7 (CH, carbon at 7-site), 125.8 (CH, carbon at 5-site), 125.3 (quaternary carbon, carbon at 4α-site), 120.5 (quaternary carbon, carbon at 4-site), 116.5 (CH, carbon at 8-site), 16.5 (CH$_3$, methyl group carbon bound to 3-site).

Synthesis of 7-dimethylamino-3-methyl-carbostyril

In a 30-ml Erlenmeyer flask made of quartz, 200 mg of (E) ethyl 3-(2-amino-4-dimethylaminophenyl)-2-methyl-2-propenate were dissolved in ethanol; and, while being stirred, the mixture was irradiated with ultraviolet rays at 365 nm for 48 hours. The reaction liquid was concentrated under a reduced pressure, and the resulting crude crystal was recrystallized from ethanol, whereby the aimed compound was obtained (yield: 98%).

The structure of this compound was verified by $^1$H-NMR and $^{13}$C-NMR.

$^1$H-NMR (DMSO-d$_6$, δ ppm): 11.29 (1H, s, amide group proton), 7.52 (1H, s, proton at 4-site), 7.32 (1H, d, J=8.8 Hz, proton at 5-site), 6.62 (1H, d, J=8.8 Hz, proton at 6-site), 6.46 (1H, s, proton at 8-site), 2.96 (6H, s, methyl group proton of dimethylamino group), 2.01 (3H, s, methyl group proton bound to 3-site); $^{13}$C-NMR (DMSO-d$_6$, δ ppm): 163.0 (quaternary carbon, carbonyl group carbon at 2-site), 150.8 (quaternary carbon, carbon at 7-site), 139.7 (quaternary carbon, carbon at 8-site), 136.4 (CH, carbon at 4-site), 127.6 (CH, carbon at 5-site), 123.4 (quaternary carbon, carbon at 3-site), 110.4 (quaternary carbon, carbon at 4α-site), 108.3 (CH, carbon at 6-site), 95.4 (CH, carbon at 8-site), 39.9 (CH$_3$, aminomethyl group carbon), 16.3 (CH$_3$, methyl group carbon bound to 3-site).

Synthesis of (E) 3-(2-amino-benzo[d]phenyl)-2-methyl-2-propenoic acid

Into 10 ml of tetrahydrofuran (THF), 0.65 g of (E) 3-(2-amino-benzo[d]phenyl)-2-methyl-2-propenoic acid ethyl ester was dissolved; and, with 10 ml of a 1-N aqueous sodium hydroxide solution being added thereto, the mixture was reacted for 4 hours at 40° C. After the completion of the reaction, the mixture was cooled with 10 ml of 1-N hydrochloric acid being added thereto, and the precipitated crystal was filtered out, whereby 0.57 g of the aimed compound was obtained (yield: 98%).

The structure of this compound was verified by $^1$H-NMR and $^{13}$C-NMR.

$^1$H-NMR (heavy dimethyl sulfoxide, δ ppm): 7.85–7.75 (3H, m, protons at 5'-, 6'-, and 8'-sites of benzocinnamyl aromatic ring), 7.73 (1H, s, proton at 3-site of propene), 7.52–7.33 (3H, m, protons at 4'-, 7'-, and 3'-sites of benzocinnamyl aromatic ring), 2.02 (3H, s, methyl group proton bound to 2-site of propene); $^{13}$C-NMR (heavy dimethyl sulfoxide, δ ppm): 168.9 (quaternary carbon, carbonyl carbon at 1-site), 133.3 (CH, carbon at 3-site of propene), 131.5 (quaternary carbon, carbon at 2-site of propene), 131.4 (quaternary carbon, carbon at 3a'-site of benzocinnamyl aromatic ring), 129.3 (CH, carbons at 5'- and 6'-sites of benzocinnamyl aromatic ring), 128.7 (quaternary carbon, carbon at 7a'-site of benzocinnamyl aromatic ring), 127.8 (CH, carbon at 4'- or 7'-site of benzocinnamyl aromatic ring), 126.8 (CH, carbon at 4'- or 7'-site of benzocinnamyl aromatic ring), 126.2 (quaternary carbon, carbon at 1'-site of benzocinnamyl aromatic ring), 126.0 (CH, carbon at 8'-site of benzocinnamyl aromatic ring), 124.2 (CH, carbon at 3'-site of benzocinnamyl aromatic ring), 14.1 (CH$_3$, methyl group carbon bound to 2-site of propene).

Synthesis of (E) 3-(2-amino-benzo[d]phenyl)-2-methyl-2-propenoic acid p-nitrophenyl ester Into 20 ml of dichloromethane, 0.57 g (2.5 mmol) of (E) 3-(2-amino-benzo[d]phenyl)-2-methyl-2-propenoic acid and 0.52 g (3.8 mmol) of p-nitrophenol (manufactured by Wako Pure Chemical Industries, Ltd.) were dissolved; and 20 mg of dimethylaminopyridine (manufactured by Wako Pure Chemical Industries, Ltd.) were added thereto. Further, while the mixture was stirred under cooling with ice, 0.71 g (3.8 mmol) of 1-ethyl-3-(3-dimethylaminopropyl)-carbodiimide hydrochloride (EDC-HCl) (manufactured by Wako Pure Chemical Industries, Ltd.) was added thereto in portions. The mixture was returned to room temperature and then was stirred for 20 hours. After the end point of this reaction was verified by TLC, the reaction liquid was concentrated under a reduced pressure and then was dissolved in 100 ml of ethyl acetate. This solution was washed several times with a 5% aqueous sodium hydrogencarbonate solution and then with a saturated aqueous sodium chloride solution, and was dried with magnesium sulfate anhydride. Thereafter, the solvent was evaporated, whereby a crude product was obtained. This product was recrystallized from ethanol, whereby 0.69 g of the aimed product was obtained as a crystal (yield: 80%).

The structure of this compound was verified by $^1$H-NMR and $^{13}$C-NMR.

$^1$H-NMR (heavy chloroform, δ ppm): 8.32 (2H, d, J=9 Hz, protons at 3"- and 5"-sites of nitrophenyloxy group), 8.01 (1H, s, proton at 3-site of propene), 7.73–7.67 (2H, m, protons at 5' - and 6'-sites of benzocinnamyl aromatic ring), 7.61 (1H, d, d=8 Hz, proton at 4'- or 7'-site of benzocinnamyl aromatic ring), 7.43–7.38 (1H, m, proton at 4'- or 6'-site of benzocinnamyl aromatic ring), 7.39 (2H, d, J=9 Hz, protons at 2"- and 6"-sites of nitrophenyloxy group), 7.29–7.24 (1H, m, proton at 8'-site of benzocinnamyl aromatic ring), 7.09 (1H, s, proton at 3'-site of benzocinnamyl aromatic ring), 3.91 (2H, bs, amino group proton), 2.23 (3H, s, methyl group proton bound to 2-site of propene); $^{13}$C-NMR (heavy chloroform, δ ppm): 165.7 (quaternary carbon, carbonyl carbon at 1-site), 155.8 (quaternary carbon, carbon at 1"-site of nitrophenyloxy group), 145.3 (quaternary carbon, carbon at 4"-site of nitrophenyloxy group), 142.4 (quaternary carbon, carbon at 2'-site of benzocinnamyl aromatic ring), 138.0 (CH, carbon at 3-site of propene), 135.0 (quaternary carbon, carbon at 2-site of propene), 129.6 (quaternary carbon, carbon at 3a'-site of benzocinnamyl aromatic ring), 129.4 (CH, carbon at 5'- or 6'-site of benzocinnamyl aromatic ring), 128.0 (CH, carbon at 5'- or 6'-site of benzocinnamyl aromatic ring), 127.5 (quaternary carbon, carbon at 7a'-site of benzocinnamyl aromatic ring), 127.1 (CH, carbon at 4'- or 7'-site of benzocinnamyl aromatic ring), 125.5 (CH, carbon at 4'- or 7'-site of benzocinnamyl aromatic ring), 125.2 (CH, carbons at 3"- and 5"-sites of nitrophenyloxy group), 123.8 (quaternary carbon, carbon at 1'-site of benzocinnamyl aromatic ring), 123.1 (CH, carbon at 8'-site of benzocinnamyl aromatic ring), 122.5 (CH, carbons at 2"- and 6"-sites of nitrophenyloxy group), 109.7 (CH, carbon at 3'-site of benzocinnamyl aromatic ring), 14.4 (CH$_3$, methyl group carbon bound to 2-site of propene).

Synthesis of (E) 3-(2-aminophenyl)-2-methyl-2-propenoic acid

Into 10 ml of tetrahydrofuran (THF), 1.50 g (7.31 mmol) of (E) ethyl 3-(2-aminophenyl)-2-methyl-2-propenate were dissolved; and, with 10 ml of a 1-N aqueous sodium hydroxide solution being added thereto, the mixture was reacted at 40° C. for 4 hours. After the completion of the reaction was verified by TLC, the mixture was cooled with 10 ml of 1-N hydrochloric acid being added thereto. The precipitated crystal was filtered out, whereby 1.30 g of the aimed compound were obtained (quantitatively).

The structure of this compound was verified by $^1$H-NMR and $^{13}$C-NMR.

$^1$H-NMR (heavy dimethyl sulfoxide, δ ppm): 7.70 (1H, s, proton at 3-site of propene), 7.49 (1H, d, J=7 Hz, proton at 3'-site of aromatic ring), 7.42–7.29 (3H, m, protons at 4'-, 5'-, and 6'-sites of aromatic ring), 1.91 (3H, s, methyl group proton bound to 2-site of propene); $^{13}$C-NMR (heavy dimethyl sulfoxide, δ ppm): 168.7 (quaternary carbon, carbonyl carbon at 1-site), 132.6 (CH, carbon at 3-site of propene), 132.1 (quaternary carbon, carbon at 2-site of propene), 130.2 (CH, carbon at 4'-site of aromatic ring), 129.3 (CH, carbon at 6'-site of aromatic ring), 128.8 (quaternary carbon, carbon at 1'-site of aromatic ring), 126.0 (CH, carbon at 5'-site of aromatic ring), 122.4 (CH, carbon at 3'-site of aromatic ring), 14.1 (CH$_3$, methyl group carbon bound to 2-site of propene).

Synthesis of (E) 3-(2-aminophenyl)-2-methyl-2-propenoic acid p-nitrophenyl ester Into 20 ml of dichloromethane, 0.19 g (1.1 mmol) of (E) 3-(2-aminophenyl)-2-methyl-2-propenoic acid and 0.18 g of p-nitrophenol (manufactured by Wako Pure Chemical Industries, Ltd.) were dissolved; and 10 mg of dimethylaminopyridine (manufactured by Wako Pure Chemical Industries, Ltd.) were added thereto. Further, while the mixture was stirred under cooling with ice, 0.41 g of 1-ethyl-3-(3-dimethylaminopropyl)-carbodiimide hydrochloride (EDC-HCl) (manufactured by Wako Pure Chemical Industries, Ltd.) was added thereto in portions. The mixture was returned to room temperature and then was stirred for 20 hours. After the end point of this reaction was verified by TLC, the reaction liquid was concentrated under a reduced pressure and then was dissolved in 100 ml of ethyl acetate. This solution was washed several times with a 5% aqueous sodium hydrogencarbon ate solution and then with a saturated aqueous sodium chloride solution, and was dried with magnesium sulfate anhydride. Thereafter, the solvent was evaporated, whereby a crude product was obtained. This product was recrystallized from ethanol, whereby 0.29 g of the aimed compound was obtained as a crystal (yield: 91%).

The structure of this compound was verified by $^1$H-NMR and $^{13}$C-NMR.

$^1$H-NMR (heavy dimethyl sulfoxide, δ ppm): 8.35 (2H, d, J=9 Hz, protons at 3"- and 5"-sites of nitrophenyloxy group), 7.86 (1H, s, proton at 3-site of propene), 7.54 (2H, d, J=9 Hz, protons at 2"- and 6"-sites of nitrophenyloxy group), 7.17 (1H, d, J=8 Hz, proton at 6'-site of cinnamyl aromatic ring), 7.09 (1H, dd, J=8 Hz, J=8 Hz, proton at 4'-site of cinncamyl aromatic ring), 6.75 (1H, d, J=8 Hz, proton at 3'-site of aromatic ring), 6.63 (1H, dd, J=8 Hz, J=8 Hz, proton at 5'-site of aromatic ring), 5.35 (2H, bs, amino group proton), 2.10 (3H, s, methyl group proton bound to 2-site of propene); $^3$C-NMR (heavy dimethyl sulfoxide, δ ppm): 165.8 (quaternary carbon, carbonyl carbon at 1-site), 156.0 (quaternary carbon, carbon at 1"-site of nitrophenyloxy group), 147.4 (quaternary carbon, carbon at 4"-site of nitrophenyloxy group), 144.8 (quaternary carbon, carbon at 2'-site of cinnamyl aromatic ring), 138.6 (CH, carbon at 3-site of propene), 130.0 (CH, carbon at 4'-site of cinnamyl aromatic ring), 129.4 (CH, carbon at 6'-site of cinnamyl aromatic ring), 125.2 (quaternary carbon, carbon at 1'-site of cinnamyl aromatic ring), 125.1 (CH, carbons at 3"- and 5"-sites of nitrophenyloxy group), 123.1 (CH, carbons at 2"- and 6"-sites of nitrophenyloxy group), 118.6 (quaternary carbon, carbon at 2-site of propene), 115.5 (CH, carbon at 5'-site of cinnamyl aromatic ring), 115.3 (CH, carbon at 3'-site of cinnamyl aromatic ring), 14.2 (CH$_3$, methyl group carbon bound to 2-site of propene).

Synthesis of (E) 3-(2-amino-4-chlorophenyl)-2-methyl-2-propenoic acid

Into 10 ml of tetrahydrofuran (THF), 1.24 g (5.18 mmol) of (E) ethyl 3-(2-aminophenyl-4-chlorophenyl)-2-methyl-2-propenate were dissolved; and, with 10 ml of a 1-N aqueous sodium hydroxide solution being added thereto, the mixture was reacted at 40° C. for 4 hours. After the completion of the reaction was verified by TLC, the mixture was cooled with 10 ml of 1-N hydrochloric acid being added thereto. The precipitated crystal was filtered out, whereby 1.03 g of the aimed compound were obtained (yield: 94%).

The structure of this compound was verified by $^1$H-NMR and $^{13}$C-NMR.

$^1$H-NMR (heavy dimethyl sulfoxide, δ ppm): 7.42 (1H, s, proton at 3-site of propene), 7.02 (1H, d, J=8 Hz, proton at 6'-site of aromatic ring), 6.74 (1H, s, proton at 3'-site of aromatic ring), 6.55 (1H, d, J=8 Hz, proton at 5'-site of aromatic ring), 5.37 (2H, bs, amino group proton), 1.90 (3H, s, methyl group proton bound to 2-site of propene); $^{13}$C-NMR (heavy dimethyl sulfoxide, δ ppm): 169.2 (quaternary carbon, carbonyl carbon at 1-site), 148.2 (quaternary carbon, carbon at 2'-site of aromatic ring), 133.7 (CH, carbon at 3-site of propene), 133.4 (quaternary carbon, carbon at 4'-site of aromatic ring), 130.7 (CH, carbon at 6'-site of aromatic ring), 128.7 (quaternary carbon, carbon at 2-site of propene), 118.3 (quaternary carbon, carbon at 1'-site of aromatic ring), 115.0 (CH, carbon at 5'-site of aromatic ring), 114.0 (CH, carbon at 3'-site of aromatic ring), 14.1 (CH$_3$, methyl group carbon bound to 2-site of propene).

Synthesis of (E) 3-(2-amino-4-chlorophenyl)-2-methyl-2-propenoic acid p-nitrophenyl ester Into 20 ml of dichloromethane, 0.81 g (3.8 mmol) of (E) 3-(2-amino-4-chlorophenyl)-2-methyl-2-propenoic acid and 1.0 g of p-nitrophenol (manufactured by Wako Pure Chemical Industries, Ltd.) were dissolved; and 40 mg of dimethylaminopyridine (manufactured by Wako Pure Chemical Industries, Ltd.) were added thereto. Further, while the mixture was stirred under cooling with ice, 1.0 g of 1-ethyl-3-(3-dimethylaminopropyl)-carbodiimide hydrochloride (EDC-HCl) (manufactured by Wako Pure Chemical Industries, Ltd.) was added thereto in portions. The mixture was returned to room temperature and then was stirred for 20 hours. After the end point of this reaction was verified by TLC, the reaction liquid was concentrated under a reduced pressure and then was dissolved in 100 ml of ethyl acetate. This solution was washed several times with a 5% aqueous sodium hydrogencarbon ate solution and then with a saturated aqueous sodium chloride solution, and was dried with magnesium sulfate anhydride. Thereafter, the solvent was evaporated, whereby a crude product was obtained. This product was recrystallized from ethanol, whereby 1.2 g of the aimed compound were obtained as a crystal (yield: 91%).

The structure of this compound was verified by $^1$H-NMR and $^{13}$C-NMR.

¹H-NMR (heavy dimethyl sulfoxide, (δ ppm): 8.30 (2H, d, J=9 Hz, protons at 3"- and 5"-sites of nitrophenyloxy group), 7.80 (1H, s, proton at 3-site of propene), 7.45 (2H, d, J=9 Hz, protons at 2"1- and 6"-sites of nitrophenyloxy group), 7.09 (1H, d, J=8 Hz, proton at 6'-site of aromatic ring), 6.81 (1H, s, proton at 3'-site of aromatic ring), 6.63 (1H, d, J=8 Hz, proton at 5'-site of aromatic ring), 5.08 (2H, bs, amino group proton), 2.11 (3H, s, methyl group proton bound to 2-site of propene); ¹³C-NMR (heavy dimethyl sulfoxide, δ ppm): 170.5 (quaternary carbon, carbonyl carbon at 1-site), 160.9 (quaternary carbon, carbon at 1"-site of nitrophenyloxy group), 152.9 (quaternary carbon, carbon at 4"-site of nitrophenyloxy group), 149.8 (quaternary carbon, carbon at 2'-site of cinnamyl aromatic ring), 142.4 (CH, carbon at 3-site of propene), 139.9 (quaternary carbon, carbon at 4'-site of cinnamyl aromatic ring), 135.6 (CH, carbon at 6'-site of cinnamyl aromatic ring), 131.8 (quaternary carbon, carbon at 2-site of propene), 129.9 (CH, carbons at 3"- and 5"-sites of nitrophenyloxy group), 127.9 (CH, carbons at 2"- and 6"-sites of nitrophenyloxy group), 122.7 (quaternary carbon, carbon at 1'-site of cinnamyl aromatic ring), 121.1 (CH, carbon at 5'-site of cinnamyl aromatic ring), 119.7 (CH, carbon at 3'-site of cinnamyl aromatic ring), 19.2 (CH₃, methyl group carbon bound to 2-site of propene).

Synthesis of (E) N-L-aspartic acid 3-(2-amino-4,5-dimethoxyphenyl)-2-methyl-2-propenoic amide Into 20 ml of dimethylformamide, 0.25 g (0.75 mmol) of (E) 3-(2-amino-4,5-dimethoxyphenyl)-2-methyl-2-propenoic acid N-succinimide ester was dissolved; and, with a solution in which 2.3 g (5.0 mmol) of L-aspartic acid had been dissolved in 40 ml of a 0.5-N aqueous sodium hydrogencarbon ate solution being added thereto, the mixture was reacted for 4 hours at room temperature. After the pH of the reaction liquid was adjusted to about pH 4 with 2-N hydrochloric acid being added thereto, the reaction liquid was concentrated under a reduced pressure as it was. Thus concentrated product was once dissolved in 20 ml of water, and then was lyophilized in order to eliminate remaining hydrochloric acid. The resulting lyophilized product was refined by a silica gel column chromatography using a moving phase of chloroform/methanol/trifluoroacetic acid at 100/10/0.01 to 40/10/0.01, and then was lyophilized, whereby 0.19 g of the aimed compound was obtained (yield: 72%).

The structure of this compound was verified by ¹H-NMR and ¹³C-NMR.

¹H-NMR (heavy dimethyl sulfoxide, δ ppm): 8.22 (1H, d, J=8 Hz, amide group proton), 7.24 (1H, S, proton at 3-site of propene), 6.98 (1H, s, proton at 3'-site of cinnamyl aromatic ring), 6.89 (1H, s, proton at 6'-site of cinnamyl aromatic ring), 4.68 (1H, t-d, J=8 Hz, J=4 Hz, proton at α-site of aspartic acid portion), 3.79 (3H, s, methyl group proton of methoxy group bound to aromatic ring), 3.78 (3H, s, methyl group proton of methoxy group bound to aromatic ring), 2.83 (1H, d-d, J=4 Hz, J=17 Hz, proton at β-site of aspartic acid portion), 2.72 (1H, d-d, J=4 Hz, J=17 Hz, proton at 3-site of aspartic acid portion), 1.96 (3H, s, methyl group proton bound to 2-site of propene); ¹³C-NMR (heavy dimethyl sulfoxide, δ ppm): 172.5 (quaternary carbon, carbonyl carbon in aspartic acid portion), 171.9 (quaternary carbon, carbonyl carbon in aspartic acid portion), 170.0 (quaternary carbon, carbonyl carbon at 1-site of propene), 149.1 (quaternary carbon, carbon at 4'-site of cinnamyl aromatic ring), 146.3 (quaternary carbon, carbon at 2'-site of cinnamyl aromatic ring), 139.4 (quaternary carbon, carbon at 5'-site of cinnamyl aromatic ring), 133.9 (quaternary carbon, carbon at 2-site of propene), 127.8 (CH, carbon at 3-site of propene), 115.8 (quaternary carbon, carbon at 1'-site of cinnamyl aromatic ring), 113.4 (CH, carbon at 6'-site of cinnamyl aromatic ring), 106.0 (CH, carbon at 3'-site of cinnamyl aromatic ring), 56.1 (CH₃, methyl group carbon of methoxy group bound to aromatic ring), 55.6 (CH₃, methyl group carbon of methoxy group), 49.2 (CH, carbon at α-site of aspartic acid portion), 35.9 (CH₂, carbon at 1-site of aspartic acid portion), 14.4 (CH₃, methyl group carbon bound to 2-site of propene).

Synthesis of (E) N-(o-di-t-butyloxy)-L-aspartic acid 3-(2-amino-4,5-dimethoxyphenyl)-2-methyl-2-propenoic amide Into 20 ml of dimethylformamide, 0.25 g (0.75 mmol) of (E) 3-(2-amino-4,5-dimethoxyphenyl)-2-methyl-2-propenoic acid N-succinimide ester was dissolved; and, with 0.28 g (1.0 mmol) of L-aspartic acid di-t-butyl ester hydrochloride (manufactured by Kokusan Chemical Works) being added thereto, the mixture was reacted for 4 hours at room temperature. After the completion of the reaction was verified by TLC, ethyl acetate and water were added thereto. The resulting ethyl acetate layer was fractionated, washed, and dried with magnesium sulfate anhydride. Thereafter, the solvent was evaporated under a reduced pressure, and the residue was refined by a silica gel column chromatography (developing solvent: methylene chloride/methanol=95/5), whereby 0.23 g of the aimed compound was obtained (yield: 65%).

The structure of this compound was verified by ¹H-NMR and ¹³C-NMR.

¹H-NMR (heavy chloroform, δ ppm): 7.36 (1H, s, proton at 3-site of propene), 7.05 (1H, d, J=8 Hz, amide group proton), 6.63 (1H, s, proton at 6'-site of cinnamyl aromatic ring), 6.33 (1H, s, proton at 3'-site of cinnamyl aromatic ring), 4.81 (1H, t-d, J=8 Hz, J=4 Hz, methine group proton at α-site of aspartic acid portion), 3.83 (3H, s, methyl group proton of methoxy group bound to aromatic ring), 3.79 (3H, s, methyl group proton of methoxy group bound to aromatic ring), 2.95 (1H, d-d, J=4 Hz, J=17 Hz, methylene group proton at β-site of aspartic acid portion), 2.82 (1H, d-d, J=4 Hz, J=17 Hz, methylene group proton at β-site of aspartic acid portion), 2.06 (3H, s, methyl group proton bound to 2-site of propene), 1.49 (9H, s, methyl group proton of butyl group), 1.46 (9H, s, methyl group proton of butyl group); ¹³C-NMR (heavy chloroform, δ ppm): 170.1 (quaternary carbon, carbonyl carbon in aspartic acid portion), 169.7 (quaternary carbon, carbonyl carbon in aspartic acid portion), 168.4 (quaternary carbon, carbonyl carbon at 1-site of propene), 150.0 (quaternary carbon, carbon at 4'-site of cinnamyl aromatic ring), 141.1 (quaternary carbon, carbon at 2'-site of cinnamyl aromatic ring), 139.4 (quaternary carbon, carbon at 5'-site of cinnamyl aromatic ring), 131.1 (CH, carbon at 3-site of propene), 130.4 (quaternary carbon, carbon at 2-site of propene), 113.4 (CH, carbon at 6'-site of cinnamyl aromatic ring), 112.2 (quaternary carbon, carbon at 1'-site of cinnamyl aromatic ring), 100.0 (CH, carbon at 3'-site of cinnamyl aromatic ring), 82.0 (quaternary carbon, butyl group), 81.2 (quaternary carbon, butyl group), 56.4 (CH₃, methyl group carbon of methoxy group bound to aromatic ring), 55.4 (CH₃, methyl group carbon of methoxy group bound to aromatic ring), 49.2 (CH, carbon at α-site of aspartic acid portion), 37.2 (CH₂, carbon at β-site of aspartic acid portion), 27.7 (CH₃, methyl group carbon of butyl group), 27.6 (CH₃, methyl group carbon of butyl group), 13.9 (CH₃, methyl group carbon bound to 2-site of propene).

Synthesis of (E) N-(o-di-t-butyloxy)-L-aspartic acid 3-(2-amino-4,5-dimethoxyphenyl)-2-methyl-2-propenoic amide Into 3 ml of dimethylformamide, 0.30 g (0.84 mmol) of (E) 3-(2-amino-4,5-dimethoxyphenyl)-2-methyl-2-propenoic acid p-nitrophenyl ester and 0.28 g (1.0 mmol) of L-aspartic acid di-t-butyl ester hydrochloride (manufactured by Kokusan Chemical Works) were dissolved; and, with 0.14 ml of triethylamine (manufactured by Wako Pure Chemical Industries, Ltd.) being added thereto, the mixture was reacted for 20 hours at room temperature. After the completion of the reaction was verified by TLC, ethyl acetate and water were added to the reaction liquid. The resulting ethyl acetate layer was fractionated. Thus obtained solution was washed several times with a 5% aqueous sodium hydrogencarbon ate solution and then with a saturated aqueous sodium chloride solution, and was dried with magnesium sulfate anhydride. Thereafter, the solvent was evaporated under a reduced pressure, and the residue was refined by a silica gel column chromatography (developing solvent: methylene chloride/methanol=95/5), whereby 0.39 g of the aimed compound was obtained (yield: quantitative).

The structure of this compound was verified by $^1$H-NMR and $^{13}$C-NMR.

$^1$H-NMR (heavy chloroform, δ ppm ): 7.36 (1H, s, proton at 3-site of propene), 7.05 (1H, d, J=8 Hz, amide group proton), 6.63 (1H, s, proton at 6'-site of cinnamyl aromatic ring), 6.33 (1H, s, proton at 3'-site of cinnamyl aromatic ring), 4.81 (1H, t-d, J=8 Hz, J=4 Hz, methine group proton at α-site of aspartic acid portion), 3.83 (3H, s, methyl group proton of methoxy group bound to aromatic ring), 3.79 (3H, s, methyl group proton of methoxy group bound to aromatic ring), 2.95 (1H, d-d, J=4 Hz, J=17 Hz, methylene group proton at β-site of aspartic acid portion), 2.82 (1H, d-d, J=4 Hz, J=17 Hz, methylene group proton at β-site of aspartic acid portion), 2.06 (3H, s, methyl group proton bound to 2-site of propene), 1.49 (9H, s, methyl group proton of butyl group), 1.46 (9H, s, methyl group proton of butyl group); $^{13}$C-NMR (heavy chloroform, δ ppm): 170.1 (quaternary carbon, carbonyl carbon in aspartic acid portion), 169.7 (quaternary carbon, carbonyl carbon in aspartic acid portion), 168.4 (quaternary carbon, carbonyl carbon at 1-site of propene), 150.0 (quaternary carbon, carbon at 4'-site of cinnamyl aromatic ring), 141.1 (quaternary carbon, carbon at 2'-site of cinnamyl aromatic ring), 139.4 (quaternary carbon, carbon at 5'-site of cinnamyl aromatic ring), 131.1 (CH, carbon at 3-site of propene), 130.4 (quaternary carbon, carbon at 2-site of propene), 113.4 (CH, carbon at 6'-site of cinnamyl aromatic ring), 112.2 (quaternary carbon, carbon at 1'-site of cinnamyl aromatic ring), 100.0 (CH, carbon at 3'-site of cinnamyl aromatic ring), 82.0 (quaternary carbon, butyl group), 81.2 (quaternary carbon, butyl group), 56.4 (CH$_3$, methyl group carbon of methoxy group bound to aromatic ring), 55.4 (CH$_3$, methyl group carbon of methoxy group bound to aromatic ring), 49.2 (CH, carbon at α-site of aspartic acid portion), 37.2 (CH$_2$, carbon at α-site of aspartic acid portion), 27.7 (CH$_3$, methyl group carbon of butyl group), 27.6 (CH$_3$, methyl group carbon of butyl group), 13.9 (CH$_3$, methyl group carbon bound to 2-site of propene).

Synthesis of (E) N-L-aspartic acid 3-(2-amino-4,5-dimethoxyphenyl)-2-methyl-2-propenoic amide Into chloroform containing 10% trifluoroacetic acid, 0.39 g (0.84 mmol) of (E) N-(o-di-t-butyloxy)-L-aspartic acid 3-(2-amino-4,5-dimethoxyphenyl)-2-methyl-2-propenoic amide was dissolved; and a de-protecting reaction (reaction for liberating protective groups) was carried out for 3 hours at room temperature. After the completion of the reaction was verified by TLC, concentration under a reduced pressure and drying were effected, whereby 0.30 g of the aimed compound was obtained (yield: quantitative).

The structure of this compound was verified by $^1$H-NMR and $^{13}$C-NMR.

$^1$H-NMR (heavy dimethyl sulfoxide, δ ppm): 8.22 (1H, d, J=8 Hz, amide group proton), 7.24 (1H, s, proton at 3-site of propene), 6.98 (1H, S, proton at 3'-site of cinnamyl aromatic ring), 6.89 (1H, s, proton at 6'-site of cinnamyl aromatic ring), 4.68 (1H, t-d, J=8 Hz, J=4 Hz, proton at α-site of aspartic acid portion), 3.79 (3H, s, methyl group proton of methoxy group bound to aromatic ring), 3.78 (3H, s, methyl group proton of methoxy group bound to aromatic ring), 2.83 (1H, d-d, J=4 Hz, J=17 Hz, proton at β-site of aspartic acid portion), 2.72 (1H, d-d, J=4 Hz, J=17 Hz, proton at β-site of aspartic acid portion), 1.96 (3H, s, methyl group proton bound to 2-site of propene); $^{13}$c-NMR (heavy dimethyl sulfoxide, δ ppm): 172.5 (quaternary carbon, carbonyl carbon in aspartic acid portion), 171.9 (quaternary carbon, carbonyl carbon in aspartic acid portion), 170.0 (quaternary carbon, carbonyl carbon at 1-site of propene), 149.1 (quaternary carbon, carbon at 4'-site of cinnamyl aromatic ring), 146.3 (quaternary carbon, carbon at 2-site of cinnamyl aromatic ring), 139.4 (quaternary carbon, carbon at 5'-site of cinnamyl aromatic ring), 133.9 (quaternary carbon, carbon at 2-site of propene), 127.8 (CH, carbon at 3-site of propene), 115.8 (quaternary carbon, carbon at 1'-site of cinnamyl aromatic ring), 113.4 (CH, carbon at 6'-site of cinnamyl aromatic ring), 106.0 (CH, carbon at 3'-site of cinnamyl aromatic ring), 56.1 (CH$_3$, methyl group carbon of methoxy group bound to aromatic ring), 55.6 (CH$_3$, methyl group carbon of methoxy group bound to aromatic ring), 49.2 (CH, carbon at α-site of aspartic acid portion), 35.9 (CH$_2$, carbon at β-site of aspartic acid portion), 14.4 (CH$_3$, methyl group carbon bound to 2-site of propene).

Synthesis of (E) N-3-carboxypropyl 3-(2-amino-4,5-dimethoxyphenyl)-2-methyl-2-propenoic amide Into 20 ml of dimethylformamide, 0.25 g (0.75 mmol) of (E) 3-(2-amino-4,5-dimethoxyphenyl)-2-methyl-2-propenoic acid N-succinimide ester was dissolved; and, with a solution in which 0.52 g (5.0 mmol) of γ-amino n-butyric acid (manufactured by Wako Pure Chemical Industries, Ltd.) had been dissolved in 40 ml of a 0.5-N aqueous sodium hydrogencarbon ate solution being added thereto, the mixture was reacted for 4 hours at room temperature. After its pH was adjusted to about 4 with 2-N hydrochloric acid being added thereto, the reaction liquid was concentrated under a reduced pressure as it was. The resulting residue was once dissolved in 20 ml of water, and then was lyophilized in order to eliminate remaining hydrochloric acid. The resulting lyophilized product was refined by a silica gel column chromatography using a moving phase of chloroform/methanol/trifluoroacetic acid at 100/10/0.01 to 40/10/0.01, and then was lyophilized, whereby 0.18 g of the aimed compound was obtained (yield: 75%).

The structure of this compound was verified by $^1$H-NMR and $^{13}$C-NMR.

$^1$H-NMR (heavy dimethyl sulfoxide, δ ppm): 8.23 (1H, bs, amide group proton), 7.08 (1H, s, proton at 3-site of propene), 6.74 (1H, s, proton at 6'-site of cinnamyl aromatic ring), 6.70 (1H, s, proton at 3'-site of cinnamyl aromatic ring), 3.74 (3H, s, methyl group proton of methoxy group bound to aromatic ring), 3.71 (3H, s, methyl group proton of methoxy group bound to aromatic ring), 3.21 (2H, t, J=7 Hz, methylene group proton at γ-site of GABA portion), 2.29 (2H, t, J=7 Hz, methylene group proton at α-site of GABA portion), 1.94 (3H, s, methyl group proton bound to 2-site of propene), 1.75 (2H, t-t, J=7 Hz, J=7 Hz, methylene group proton at β-site of GABA portion); $^{13}$C-NMR (heavy dimethyl sulfoxide, δ ppm): 174.2 (quaternary carbon, carbonyl carbon in GABA portion), 169.4 (quaternary carbon, carbonyl carbon at 1-site of propene), 149.4 (quaternary carbon, carbon at 4'-site of cinnamyl aromatic ring), 142.6 (quaternary carbon, carbon at 2'-site of cinnamyl aromatic ring), 134.9 (quaternary carbon, carbon at 5'-site of cinnamyl aromatic ring), 132.4 (quaternary carbon, carbon at 2-site of propene), 127.4 (CH, carbon at 3-site of propene), 115.4 (quaternary carbon, carbon at 1'-site of cinnamyl aromatic ring), 113.9 (CH, carbon at 6'-site of cinnamyl aromatic ring), 102.7 (CH, carbon at 3'-site of cinnamyl aromatic ring), 56.4 (CH$_3$, methyl group carbon of methoxy group bound to aromatic ring), 55.3 (CH$_3$, methyl group carbon of methoxy group bound to aromatic ring), 38.4 (CH$_2$, methylene group carbon at γ-site of GABA portion), 31.3 (CH$_2$, methylene group carbon at α-site of GABA portion), 24.6 (CH$_2$, methylene group carbon at β-site of GABA portion), 14.6 (CH$_3$, methyl group carbon bound to 2-site of propene).

Synthesis of (E) N-3-methyloxycarbonylpropyl 3-(2-amino-4,5-dimethoxyphenyl)-2-methyl-2-propenoic amide Into 20 ml of dimethylformamide, 0.25 g (0.75 mmol) of (E) 3-(2-amino-4,5-dimethoxyphenyl)-2-methyl-2-propenoic acid N-succinnimide ester was dissolved; and, with 0.15 g (1.0 mmol) of γ-amino butanoic acid ethyl ester hydrochloride (manufactured by Nakalai Tesque, Inc.) being added thereto, the mixture was reacted for 4 hours at room temperature. After the completion of the reaction was verified by TLC, ethyl acetate and water were added thereto, and the ethyl acetate layer was fractionated. The resulting organic layer was washed and then was dried with magnesium sulfate anhydride. Thereafter, the solvent was evaporated under a reduced pressure, and the residue was refined by a silica gel column chromatography (developing solvent: methylene chloride/methanol=95/5), whereby 0.18 g of the aimed compound was obtained (yield: 70%).

The structure of this compound was verified by $^1$H-NMR and $^{13}$C-NMR.

$^1$H-NMR (heavy chloroform, δ ppm ): 7.33 (1H, s, proton at 3-site of propene), 6.65 (1H, s, proton at 6'-site of cinnamyl aromatic ring), 6.35 (1H, s, proton at 3'-site of cinnamyl aromatic ring), 3.83 (3H, s, methyl group proton of methoxy group bound to aromatic ring), 3.79 (3H, s, methyl group proton of methoxy group bound to aromatic ring), 3.68 (3H, s, methylene group proton of methyl ester in GABA portion), 3.47 (2H, t, J=7 Hz, methylene group proton at γ-site of GABA portion), 2.46 (2H, t, J=7 Hz, methylene group proton at α-site of GABA portion), 2.07 (3H, s, methyl group proton bound to 2-site of propene), 1.96 (2H, t-t, J=7 Hz, J=7 Hz, methylene group proton at β-site of GABA portion); $^{13}$C-NMR (heavy chloroform, δ ppm): 174.2 (quaternary carbon, carbonyl carbon in GABA portion), 170.6 (quaternary carbon, carbonyl carbon at 1-site of propene), 150.2 (quaternary carbon, carbon at 4'-site of cinnamyl aromatic ring), 141.2 (quaternary carbon, carbon at 2'-site of cinnamyl aromatic ring), 139.5 (quaternary carbon, carbon at 5'-site of cinnamyl aromatic ring), 131.2 (CH, carbon at 3-site of propene), 130.1 (quaternary carbon, carbon at 2-site of propene), 113.5 (CH, carbon at 6'-site of cinnamyl aromatic ring), 112.3 (quaternary carbon, carbon at 1'-site of cinnamyl aromatic ring), 100.4 (CH, carbon at 3'-site of cinnamyl aromatic ring), 56.6 (CH$_3$, methyl group carbon of methoxy group bound to aromatic ring), 55.5 (CH, methyl group carbon of methoxy group bound to aromatic ring), 51.7 (CH$_3$, methyl group carbon of methyl ester in GABA portion), 39.8 (CH$_2$, methylene group carbon at γ-site of GABA portion), 31.5 (CH$_2$, methylene group carbon at α-site of GABA portion), 23.9 (CH$_2$, methylene group carbon at 3-site of GABA portion), 14.0 (CH$_3$, methyl group carbon bound to 2-site of propene).

Synthesis of (E) N-3-methyloxycarbonylpropyl 3-(2-amino-4,5-dimethoxyphenyl)-2-methyl-2-propenoic amide Into 3 ml of dimethylformamide, 0.30 g (0.84 mmol) of (E) 3-(2-amino-4,5-dimethoxyphenyl)-2-methyl-2-propenoic acid p-nitrophenyl ester and 0.15 g (1.00 mmol) of 7-amino butanoic acid ethyl ester hydrochloride (manufactured by Nakalai Tesque, Inc.) were dissolved; and, with 0.14 ml of triethylamine (manufactured by Wako Pure Chemical Industries, Ltd.) being added thereto, the mixture was reacted for 20 hours at room temperature. After the completion of the reaction was verified by TLC, ethyl acetate and water were added to the reaction solution. The resulting ethyl acetate layer was fractionated, and was washed several times with a 5% aqueous sodium hydrogencarbon ate solution and then with a saturated aqueous sodium chloride solution. After the washed product was dried with magnesium sulfate anhydride, the solvent was evaporated under a reduced pressure, and the residue was refined by a silica gel column chromatography (developing solvent: methylene chloride/methanol=95/5), whereby 0.28 g of the aimed compound was obtained (yield: quantitative).

The structure of this compound was verified by $^1$H-NMR and $^{13}$C-NMR.

$^1$H-NMR (heavy chloroform, δ ppm): 7.33 (1H, s, proton at 3-site of propene), 6.65 (1H, s, proton at 6'-site of cinnamyl aromatic ring), 6.35 (1H, s, proton at 3'-site of cinnamyl aromatic ring), 3.83 (3H, s, methyl group proton of methoxy group bound to aromatic ring), 3.79 (3H, s, methyl group proton of methoxy group bound to aromatic ring), 3.68 (3H, s, methylene group proton of methyl ester in GABA portion), 3.47 (2H, t, J=7 Hz, methylene group proton at γ-site of GABA portion), 2.46 (2H, t, J=7 Hz, methylene group proton at α-site of GABA portion), 2.07 (3H, s, methyl group proton bound to 2-site of propene), 1.96 (2H, t-t, J=7 Hz, J=7 Hz, methylene group proton at β-site of GABA portion); $^{13}$C-NMR (heavy chloroform, δ ppm): 174.2 (quaternary carbon, carbonyl carbon in GABA portion), 170.6 (quaternary carbon, carbonyl carbon at 1-site of propene), 150.2 (quaternary carbon, carbon at 4'-site of cinnamyl aromatic ring), 141.2 (quaternary carbon, carbon at 2'-site of cinnamyl aromatic ring), 139.5 (quaternary carbon, carbon at 5'-site of cinnamyl aromatic ring), 131.2 (CH, carbon at 3-site of propene), 130.1 (quaternary carbon, carbon at 2-site of propene), 113.5 (CH, carbon at 6'-site of cinnamyl aromatic ring), 112.3 (quaternary carbon, carbon at 1'-site of cinnamyl aromatic ring), 100.4 (CH, carbon at 3'-site of cinnamyl aromatic ring), 56.6 (CH$_3$, methyl group carbon of methoxy group bound to aromatic ring), 55.5 (CH$_3$, methyl group carbon of methoxy group bound to aromatic ring), 51.7 (CH$_3$, methyl group carbon of methyl ester in GABA portion), 39.8 (CH$_2$, methylene group carbon at γ-site of GABA portion), 31.5 (CH$_2$, methylene group carbon at α-site of GABA portion), 23.9 (CH$_2$, methylene group carbon at -site of GABA portion), 14.0 (CH$_3$, methyl group carbon bound to 2-site of propene).

Synthesis of (E) N-3-carboxypropyl 3-(2-amino-4,5-dimethoxyphenyl)-2-methyl-2-propenoic amide Into 1 ml of methanol, 0.16 g (0.48 mmol) of (E) N-3-methyloxycarbonylpropyl 3-(2-amino-4,5-dimethoxyphenyl)-2-methyl-2-propenoic amide was dissolved; and, with 2 ml of a 1-N aqueous sodium hydroxide solution being added thereto, the mixture was reacted for 12 hours at room temperature. After the pH of the reaction liquid was adjusted to about 4 with 1-N hydrochloric acid, the solvent was evaporated under a reduced pressure, and the residue was refined by a silica gel column chromatography (developing solvent: dichlorometane/methanol=10/3), whereby 0.15 g of the aimed compound was obtained (yield: quantitative).

The structure of this compound was verified by $^1$H-NMR and $^{13}$C-NMR.

$^1$H-NMR (heavy dimethyl sulfoxide, δ ppm): 8.23 (1H, bs, amide group proton), 7.08 (1H, s, proton at 3-site of propene), 6.74 (1H, s, proton at 6'-site of cinnamyl aromatic ring), 6.70 (1H, s, proton at 3'-site of cinnamyl aromatic ring), 3.74 (3H, s, methyl group proton of methoxy group bound to aromatic ring), 3.71 (3H, s, methyl group proton of methoxy group bound to aromatic ring), 3.21 (2H, t, J=7 Hz, methylene group proton at γ-site of GABA portion), 2.29 (2H, t, J=7 Hz, methylene group proton at α-site of GABA portion), 1.94 (3H, s, methyl group proton bound to 2-site of propene), 1.75 (2H, t-t, J=7 Hz, J=7 Hz, methylene group proton at 3-site of GABA portion); $^{13}$C-NMR (heavy dimethyl sulfoxide, δ ppm): 174.2 (quaternary carbon, carbonyl carbon in GABA portion), 169.4 (quaternary carbon, carbonyl carbon at 1-site of propene), 149.4 (quaternary carbon, carbon at 4'-site of cinnamyl aromatic ring), 142.6 (quaternary carbon, carbon at 2'-site of cinnamyl aromatic ring), 134.9 (quaternary carbon, carbon at 5'-site of cinnamyl aromatic ring), 132.4 (quaternary carbon, carbon at 2-site of propene), 127.4 (CH, carbon at 3-site of propene), 115.4 (quaternary carbon, carbon at 1'-site of cinnamyl aromatic ring), 113.9 (CH, carbon at 6'-site of cinnamyl aromatic ring), 102.7 (CH, carbon at 3'-site of cinnamyl aromatic ring), 56.4 (CH$_3$, methyl group carbon of methoxy group bound to aromatic ring), 55.3 (CH$_3$, methyl group carbon of methoxy group bound to aromatic ring), 38.4 (CH$_2$, methylene group carbon at γ-site of GABA portion), 31.3 (CH$_2$, methylene group carbon at α-site of GABA portion), 24.6 (CH$_2$, methylene group carbon at β-site of GABA portion), 14.6 (CH$_3$, methyl group carbon bound to 2-site of propene).

Synthesis of (E) N-L-glutamic acid 3-(2-amino-benzo[d]phenyl)-2-methyl-2-propenoic amide Into 20 ml of dimethylformamide, 0.24 g (0.75 mmol) of (E) 3-(2-amino-benzo[d]phenyl)-2-methyl-2-propenoic acid N-hydroxysuccinimide ester was dissolved; and, with a solution in which 0.74 g (5.0 mmol) of L-glutamic acid had been dissolved in 40 ml of a 0.5-N aqueous sodium hydrogencarbon ate solution being added thereto, the mixture was reacted for 4 hours at room temperature. After its pH was adjusted to about 4 with 2-N hydrochloric acid being added thereto, the reaction liquid was concentrated under a reduced pressure as it was. The resulting residue was once dissolved in 20 ml of water, and then was lyophilized in order to eliminate remaining hydrochloric acid. The resulting lyophilized product was refined by a silica gel column chromatography using a moving phase of chloroform/methanol/trifluoroacetic acid at 100/10/0.01 to 40/10/0.01, and then was lyophilized, whereby 0.17 g of the aimed compound was obtained (yield: 63%).

The structure of this compound was verified by $^1$H-NMR and $^{13}$C-NMR.

$^1$H-NMR (heavy dimethyl sulfoxide, δ ppm): 8.44 (1H, d, J=7 Hz, amide group proton), 7.96 (1H, d, J=8 Hz, proton at 4'- or 7'-site of benzocinnamyl aromatic ring), 7.92 (1H, s, proton at 8'-site of benzocinnamyl aromatic ring), 7.95–7.90 (1H, m, proton at 5'- or 6'-site of benzocinnamyl aromatic ring), 7.90 (1H, s, proton at 3-site of propene), 7.59–7.47 (2H, m, proton at 4'- or 7'-site of benzocinnamyl aromatic ring and proton at 5'- or 6'-site of benzocinnamyl aromatic ring), 7.49 (1H, s, proton at 3'-site of benzocinnamyl aromatic ring), 4.41 (1H, t-d, J=12 Hz, J=5 Hz, proton at α-site of glutamic acid portion), 2.39 (2H, t, J=7 Hz, proton at γ-site of glutamic acid portion), 2.22–2.03 (2H, m, proton at β-site of glutamic acid portion), 2.11 (3H, s, methyl group proton bound to 2-site of propene); $^{13}$C-NMR (heavy dimethyl sulfoxide, δ ppm): 174.7 (quaternary carbon, carbonyl carbon in glutamic acid portion), 172.1 (quaternary carbon, carbonyl carbon in glutamic acid portion), 168.7 (quaternary carbon, carbonyl carbon at 1-site of propene), 139.5 (quaternary carbon, carbon at 2'-site of benzocinnamyl aromatic ring), 136.2 (quaternary carbon, carbon at 2-site of propene or carbon at 3a'-site of benzocinnamyl aromatic ring), 132.1 (quaternary carbon, carbon at 2-site of propene or carbon at 3a'-site of benzocinnamyl aromatic ring), 129.7 (CH, carbon at 5'- or 6'-site of benzocinnamyl aromatic ring), 127.9 (CH, carbon at 5'- or 6'-site of benzocinnamyl aromatic ring), 127.7 (quaternary carbon, carbon at 7a'-site of benzocinnamyl aromatic ring), 127.2 (CH, carbon at 4'- or 7'-site of benzocinnamyl aromatic ring), 127.0 (CH, carbon at 3-site of propene), 117.1 (CH, carbon at 4'- or 7'-site of benzocinnamyl aromatic ring)r 117.0 (quaternary carbon, carbon at 1'-site of benzocinnamyl aromatic ring), 113.3 (CH, carbon at 8'-site of benzocinnamyl aromatic ring), 109.5 (CH, carbon at 3'-site of benzocinnamyl aromatic ring), 52.3 (CH, carbon at α-site of glutamic acid portion), 31.3 (CH$_2$, carbon at γ-site of glutamic acid portion), 26.4 (CH$_2$, carbon at β-site of glutamic acid portion), 14.2 (CH$_3$, methyl group carbon bound to 2-site of propene).

Synthesis of (E) N-(o-di-t-butyloxy)-L-glutamic acid 3-(2-amino-benzo[d]phenyl)-2-methyl-2-propenoic amide Into 20 ml of dimethylformamide, 0.24 g (0.75 mmol) of (E) 3-(2-amino-benzo[d]phenyl)-2-methyl-2-propenoic acid N-hydroxysuccinimide ester was dissolved; and, with 0.29 g (1.0 mmol) of L-glutamic acid di-t-butyl ester hydrochloride (manufactured by Sigma Chemical Co.) being added thereto, the mixture was reacted for 3 hours at room temperature. After the completion of the reaction was verified by TLC, ethyl acetate and water were added thereto. The resulting ethyl acetate layer was fractionated, washed, and dried with magnesium sulfate anhydride; and the solvent was evaporated under a reduced pressure. The residue was refined by a silica gel column chromatography (developing solvent: methylene chloride/methanol=95/5), whereby 0.22 g of the aimed compound was obtained (yield: 55%).

The structure of this compound was verified by $^1$H-NMR and $^{13}$C-NMR.

$^1$H-NMR (heavy chloroform, δ ppm): 7.67 (1H, d, J=8 Hz, proton at 4'- or 7'-site of benzocinnamyl aromatic ring), 7.58 (1H, d, J=8 Hz, proton at 4'- or 7'-site of benzocinnamyl aromatic ring), 7.54 (1H, s, proton at 8'-site of benzocinnamyl aromatic ring), 7.47 (1H, s, proton at 3-site of propene), 7.36 (1H, dd, J=7 Hz, J=8 Hz, proton at 5'- or 6'-site of benzocinnamyl aromatic ring), 7.22 (1H, dd, J=7

Hz, J=8 Hz, proton at 5'- or 6'-site of benzocinnamyl aromatic ring), 7.09 (1H, d, J=7 Hz, amide group proton), 7.03 (1H, s, proton at 3'-site of benzocinnamyl aromatic ring), 4.60 (1H, ddd, J=9 Hz, J=7 Hz, J=4 Hz, proton at α-site of glutamic acid portion), 2.50–2.37 (2H, m, methylene group proton at γ-site of glutamic acid portion), 2.14–2.05 (2H, m, methylene group proton at β-site of glutamic acid portion), 2.10 (3H, s, methyl group proton bound to 2-site of propene), 1.50 (9H, s, methyl group proton of butyl group), 1.48 (9H, s, methyl group proton of butyl group); $^{13}$C-NMR (heavy chloroform, δ ppm): 174.9 (quaternary carbon, carbonyl carbon in glutamic acid portion), 171.1 (quaternary carbon, carbonyl carbon in glutamic acid portion), 169.1 (quaternary carbon, carbonyl carbon at 1-site), 142.8 (quaternary carbon, carbon at 2'-site of benzocinnamyl aromatic ring), 134.7 (quaternary carbon, carbon at 2-site of propene or carbon at 3a'-site of benzocinnamyl aromatic ring), 133.8 (quaternary carbon, carbon at 2-site of propene or carbon at 3a'-site of benzocinnamyl aromatic ring), 131.1 (CH, carbon at 3-site of propene), 129.1 (CH, carbon at 5'- or 6'-site of benzocinnamyl aromatic ring), 127.8 (CH, carbon at 5'- or 6'-site of benzocinnamyl aromatic ring), 127.5 (quaternary carbon, carbon at 7a'-site of benzocinnamyl aromatic ring), 126.6 (CH, carbon at 4'- or 7'-site of benzocinnamyl aromatic ring), 125.4 (CH, carbon at 4'- or 7'-site of benzocinnamyl aromatic ring), 124.5 (quaternary carbon, carbon at 1'-site of benzocinnamyl aromatic ring), 122.7 (CH, carbon at 8'-site of benzocinnamyl aromatic ring), 109.1 (CH, carbon at 3'-site of benzocinnamyl aromatic ring), 82.7 (quaternary carbon, butyl group), 82.5 (quaternary carbon, butyl group), 53.0 (CH, carbon at α-site of glutamic acid portion), 32.1 (CH$_2$, carbon at γ-site of glutamic acid portion), 28.4 (CH$_2$, carbon at β-site of glutamic acid portion), 28.0 (CH$_3$, methyl group carbon of butyl group), 14.1 (CH$_3$, methyl group carbon bound to 2-site of propene).

Synthesis of (E) N-(o-di-t-butyloxy)-L-glutamic acid 3-(2-amino-benzo[d]phenyl)-2-methyl-2-propenoic amide Into 2 ml of dimethylformamide, 0.20 g (0.57 mmol) of (E) 3-(2-amino-benzo[d]phenyl)-2-methyl-2-propenoic acid p-nitrophenyl ester and 0.20 g (0.69 mmol) of L-glutamic acid di-t-butyl ester hydrochloride (manufactured by Sigma Chemical Co.) were dissolved; and, with 0.01 ml of triethylamine (manufactured by Wako Pure Chemical Industries, Ltd.) being added thereto, the mixture was reacted for 20 hours at room temperature. After the completion of the reaction was verified by TLC, ethyl acetate and water were added to the reaction solution. The resulting ethyl acetate layer was fractionated, and was washed several times with a 5% aqueous sodium hydrogencarbon ate solution and then with a saturated aqueous sodiumchloride solution. After the washed product was dried with magnesium sulfate anhydride, the solvent was evaporated under a reduced pressure. Thus obtained crude product was refined by a silica gel column chromatography (developing solvent: methylene chloride/methanol=95/5), whereby 0.27 g of the aimed compound was obtained (yield: quantitative).

The structure of this compound was verified by $^1$H-NMR and $^{13}$C-NMR.

$^1$H-NMR (heavy chloroform, δ ppm): 7.67 (1H, d, J=8 Hz, proton at 4'- or 7'-site of benzocinnamyl aromatic ring), 7.58 (1H, d, J=8 Hz, proton at 4'- or 7'-site of benzocinnamyl aromatic ring), 7.54 (1H, s, proton at 8'-site of benzocinnamyl aromatic ring), 7.47 (1H, s, proton at 3-site of propene), 7.36 (1H, dd, J=7 Hz, J=8 Hz, proton at 5'- or 6'-site of benzocinnamyl aromatic ring), 7.22 (1H, dd, J=7 Hz, J=8 Hz, proton at 5'- or 6'-site of benzocinnamyl aromatic ring), 7.09 (1H, d, J=7 Hz, amide group proton), 7.03 (1H, s, proton at 3'-site of benzocinnamyl aromatic ring), 4.60 (1H, ddd, J=9 Hz, J=7 Hz, J=4 Hz, proton at α-site of glutamic acid portion), 2.50–2.37 (2H, m, methylene group proton at γ-site of glutamic acid portion), 2.14–2.05 (2H, m, methylene group proton at β-site of glutamic acid portion), 2.10 (3H, s, methyl group proton bound to 2-site of propene), 1.50 (9H, s, methyl group proton of butyl group), 1.48 (9H, s, methyl group proton of butyl group); $^{13}$C-NMR (heavy chloroform, δ ppm): 174.9 (quaternary carbon, carbonyl carbon in glutamic acid portion), 171.1 (quaternary carbon, carbonyl carbon in glutamic acid portion), 169.1 (quaternary carbon, carbonyl carbon at 1-site), 142.8 (quaternary carbon, carbon at 2'-site of benzocinnamyl aromatic ring), 134.7 (quaternary carbon, carbon at 2-site of propene or carbon at 3a'-site of benzocinnamyl aromatic ring), 133.8 (quaternary carbon, carbon at 2-site of propene or carbon at 3a'-site of benzocinnamyl aromatic ring), 131.1 (CH, carbon at 3-site of propene), 129.1 (CH, carbon at 5'- or 6'-site of benzocinnamyl aromatic ring), 127.8 (CH, carbon at 5'- or 6'-site of benzocinnamyl aromatic ring), 127.5 (quaternary carbon, carbon at 7a'-site of benzocinnamyl aromatic ring), 126.6 (CH, carbon at 4'- or 7'-site of benzocinnamyl aromatic ring), 125.4 (CH, carbon at 4'- or 7'-site of benzocinnamyl aromatic ring), 124.5 (quaternary carbon, carbon at 1'-site of benzocinnamyl aromatic ring), 122.7 (CH, carbon at 8'-site of benzocinnamyl aromatic ring), 109.1 (CH, carbon at 3'-site of benzocinnamyl aromatic ring), 82.7 (quaternary carbon, butyl group), 82.5 (quaternary carbon, butyl group), 53.0 (CH, carbon at α-site of glutamic acid portion), 32.1 (CH$_2$, carbon at γ-site of glutamic acid portion), 28.4 (CH$_2$, carbon at β-site of glutamic acid portion), 28.0 (CH$_3$, methyl group carbon of butyl group), 14.1 (CH$_3$, methyl group carbon bound to 2-site of propene).

Synthesis of (E) N-L-glutamic acid 3-(2-amino-benzo[d]phenyl)-2-methyl-2-propenoic amide Into chloroform containing 5% trifluoroacetic acid, 0.27 g (0.60 mmol) of (E) N-(o-di-t-butyloxy)-L-glutamic acid 3-(2-amino-benzo[d]phenyl)-2-methyl-2-propenoic amide was dissolved; and a de-protecting reaction was carried out for 5 hours at room temperature. After the completion of the reaction was verified by TLC, concentration under a reduced pressure and drying were effected, whereby 0.21 g of the aimed compound was obtained (yield: quantitative).

The structure of this compound was verified by $^1$H-NMR and $^{13}$C-NMR.

$^1$H-NMR (heavy dimethyl sulfoxide, δ ppm): 8.44 (1H, d, J=7 Hz, amide group proton), 7.96 (1H, d, J=8 Hz, proton at 4'- or 7'-site of benzocinnamyl aromatic ring), 7.92 (1H, s, proton at 8'-site of benzocinnamyl aromatic ring), 7.95–7.90 (1H, m, proton at 5'- or 6'-site of benzocinnamyl aromatic ring), 7.90 (1H, s, proton at 3-site of propene), 7.59–7.47 (2H, m, proton at 4'- or 7'-site of benzocinnamyl aromatic ring and proton at 5'- or 6'-site of benzocinnamyl aromatic ring), 7.49 (1H, s, proton at 3'-site of benzocinnamyl aromatic ring), 4.41 (1H, t-d, J=12 Hz, J=5 Hz, proton at α-site of glutamic acid portion), 2.39 (2H, t, J=7 Hz, proton at γ-site of glutamic acid portion), 2.22–2.03 (2H, m, proton at β-site of glutamic acid portion) 2.11 (3H, s, methyl group proton bound to 2-site of propene); $^{13}$C-NMR (heavy dimethyl sulfoxide, δ ppm): 174.7 (quaternary carbon, carbonyl carbon in glutamic acid portion), 172.1 (quaternary carbon, carbonyl carbon in glutamic acid portion), 168.7 (quaternary carbon, carbonyl carbon at 1-site of propene), 139.5 (quaternary carbon, carbon at 2'-site of benzocinnamyl aromatic ring), 136.2 (quaternary carbon, carbon at 2-site of propene or carbon at 3a'-site of benzocinnamyl aromatic ring), 132.1 (quaternary carbon, carbon at 2-site of propene or carbon at 3a'-site of benzocinnamyl aromatic ring), 129.7 (CH, carbon at 5'- or 6'-site of benzocinnamyl aromatic ring), 127.9 (CH, carbon at 5'- or 6'-site of benzocinnamyl aromatic ring), 127.7 (quaternary carbon, carbon at 7a'-site of benzocinnamyl aromatic ring), 127.2 (CH, carbon at 4'- or 7'-site of benzocinnamyl aromatic ring), 127.0 (CH, carbon at 3-site of propene), 117.1 (CH, carbon at 4'- or 7'-site of benzocinnamyl aromatic ring), 117.0 (quaternary carbon, carbon at 1'-site of benzocinnamyl aromatic ring), 113.3 (CH, carbon at 8'-site of benzocinnamyl aromatic ring), 109.5 (CH, carbon at 3'-site of benzocinnamyl aromatic ring), 52.3 (CH, carbon at α-site of glutamic acid portion), 31.3 ($CH_2$, carbon at γ-site of glutamic acid portion), 26.4 ($CH_2$, carbon at β-site of glutamic acid portion), 14.2 ($CH_3$, methyl group carbon bound to 2-site of propene).

Synthesis of (E) N-glycine 3-(2-amino-benzo[d]phenyl)-2-methyl-2-propenoic amide Into 10 ml of dimethylformamide, 0.24 g (0.75 mmol) of (E) 3-(2-amino-benzo[d]phenyl)-2-methyl-2-propenoic acid N-hydroxysuccinimide ester was dissolved; and, with a solution in which 0.38 g (5.0 minol) of glycine had been dissolved in 20 ml of a 0.5-N aqueous sodium hydrogencarbon ate solution being added thereto, the mixture was reacted for 4 hours at room temperature. After its pH was adjusted to about 4 with 2-N hydrochloric acid being added thereto, the reaction liquid was concentrated under a reduced pressure as it was. The resulting residue was once dissolved in 20 ml of water, and then was lyophilized in order to eliminate remaining hydrochloric acid. The resulting lyophilized product was refined by a silica gel column chromatography using a moving phase of chloroform/methanol/trifluoroacetic acid at 100/10/0.01 to 40/10/0.01, and then was lyophilized, whereby 0.15 g of the aimed compound was obtained (yield: 72%).

The structure of this compound was verified by $^1$H-NMR and $^{13}$C-NMR.

$^1$H-NMR (heavy dimethyl sulfoxide, δ ppm): 8.52 (1H, t, J=6 Hz, amide group proton), 7.66 (1H, d, J=8 Hz, proton at 4'- or 7'-site of benzocinnamyl aromatic ring), 7.55 (1H, s, proton at 8'-site of benzocinnamyl aromatic ring), 7.51 (1H, d, J=8 Hz, proton at 4'- or 7'-site of benzocinnamyl aromatic ring), 7.28 (1H, dd, J=7 Hz, J=8 Hz, proton at 5'- or 6'-site of benzocinnamyl aromatic ring), 7.16 (1H, s, proton at 3-site of propene), 7.10 (1H, dd, J=7 Hz, J=8 Hz, proton at 5'- or 6'-site of benzocinnamyl aromatic ring), 6.96 (1H, s, proton at 3'-site of benzocinnamyl aromatic ring), 3.89 (2H, d, J=6 Hz, methylene group proton at α-site of glycine portion), 1.99 (3H, s, methyl group proton bound to 2-site of propene); $^{13}$C-NMR (heavy dimethyl sulfoxide, δ ppm): 171.8 (quaternary carbon, carbonyl carbon in glycine portion), 169.4 (quaternary carbon, carbonyl carbon at 1-site), 144.9 (quaternary carbon, carbon at 2'-site of benzocinnamyl aromatic ring), 134.5 (quaternary carbon, carbon at 2-site of propene and carbon at 3a'-site of benzocinnamyl aromatic ring), 128.7 (CH, carbon at 3-site of propene), 128.4 (CH, carbon at 5'- or 6'-site of benzocinnamyl aromatic ring), 127.6 (CH, carbon at 5'- or 6'-site of benzocinnamyl aromatic ring), 126.3 (quaternary carbon, carbon at 7a'-site of benzocinnamyl aromatic ring), 126.0 (CH, carbon at 4'- or 7'-site of benzocinnamyl aromatic ring), 124.7 (CH, carbon at 4'- or 7'-site of benzocinnamyl aromatic ring), 124.0 (quaternary carbon, carbon at 1'-site of benzocinnamyl aromatic ring), 121.2 (CH, carbon at 8'-site of benzocinnamyl aromatic ring), 107.0 (CH, carbon at 3'-site of benzocinnamyl aromatic ring), 41.0 (CH, carbon at α-site of glycine portion), 14.4 ($CH_3$, methyl group carbon bound to 2-site of propene).

Synthesis of (E) N-glycine 3-(2-amino-benzo[d]phenyl)-2-methyl-2-propenoic amide Into 1 ml of dimethylformamide, 0.17 g (0.48 mmol) of (E) 3-(2-amino-benzo[d]phenyl)-2-methyl-2-propenoic acid p-nitrophenyl ester and 0.081 g (0.58 mmol) of glycine ethyl ester hydrochloride (manufactured by Kokusan Chemical Works) were dissolved; and, with 0.08 ml of triethylamine (manufactured by Wako Pure Chemical Industries, Ltd.) being added thereto, the mixture was reacted for 20 hours at room temperature. After the completion of the reaction was verified by TLC, ethyl acetate and water were added thereto. The resulting ethyl acetate layer was fractionated, washed several times with a 5% aqueous sodium hydrogencarbon ate solution and then with a saturated aqueous sodium chloride solution, and dried with magnesium sulfate anhydride. Thereafter, the solvent was evaporated under a reduced pressure, and the residue was refined by a silica gel column chromatography (developing solvent: methylene chloride/methanol=95/5). The refined product was dissolved in 1 ml of methanol; and, with 2 ml of 1-N sodium hydroxide being added thereto, a de-protecting reaction was carried out for one night at room temperature. After the F9 pH of the system was adjusted to about 4 with 2-N hydrochloric acid, the solvent was evaporated under a reduced pressure, and the residue was refined by a silica gel column chromatography (developing solvent: dichloromethane/methanol=10/3), whereby 0.14 of the aimed compound was obtained (yield: quantitative).

The structure of this compound was verified by $^1$H-NMR and $^{13}$C-NMR.

$^1$H-NMR (heavy dimethyl sulfoxide, δ ppm): 8.52 (1H, t, J=6 Hz, amide group proton), 7.66 (1H, d, J=8 Hz, proton at 4'- or 7'-site of benzocinnamyl aromatic ring), 7.55 (1H, s, proton at 8'-site of benzocinnamyl aromatic ring), 7.51 (1H, d, J=8 Hz, proton at 4'- or 7'-site of benzocinnamyl aromatic ring), 7.28 (1H, dd, J=7 Hz, J=8 Hz, proton at 5'- or 6'-site of benzocinnamyl aromatic ring), 7.16 (1H, s, proton at 3-site of propene), 7.10 (1H, dd, J=7 Hz, J=8 Hz, proton at 5'- or 6'-site of benzocinnamyl aromatic ring), 6.96 (1H, s, proton at 3'-site of benzocinnamyl aromatic ring), 3.89 (2H, d, J=6 Hz, methylene group proton at α-site of glycine portion), 1.99 (3H, s, methyl group proton bound to 2-site of propene); $^{13}$C-NMR (heavy dimethyl sulfoxide, δ ppm): 171.8 (quaternary carbon, carbonyl carbon in glycine portion), 169.4 (quaternary carbon, carbonyl carbon at 1-site), 144.9 (quaternary carbon, carbon at 2'-site of benzocinnamyl aromatic ring), 134.5 (quaternary carbon, carbon at 2-site of propene and carbon at 3a'-site of benzocinnamyl aromatic ring), 128.7 (CH, carbon at 3-site of propene), 128.4 (CH, carbon at 5'- or 6'-site of benzocinnamyl aromatic ring), 127.6 (CH, carbon at 5'- or 61-site of benzocinnamyl aromatic ring), 126.3 (quaternary carbon, carbon at 7a'-site of benzocinnamyl aromatic ring), 126.0 (CH, carbon at 4'- or 7'-site of benzocinnamyl aromatic ring), 124.7 (CH, carbon at 4'- or 7'-site of benzocinnamyl aromatic ring), 124.0 (quaternary carbon, carbon at 1'-site of benzocinnamyl aromatic ring), 121.2 (CH, carbon at 8'-site of benzocinnamyl aromatic ring), 107.0 (CH, carbon at 3'-site of benzocinnamyl aromatic ring), 41.0 (CH, carbon at α-site of glycine portion), 14.4 ($CH_3$, methyl group carbon bound to 2-site of propene).

Synthesis of (E) N-L-aspartic acid 3-(2-amino-benzo[d]phenyl)-2-methyl-2-propenoic amide Into 20 ml of dimethylformamide, 0.24 g (0.75 mmol) of (E) 3-(2-amino-benzo[d]phenyl)-2-methyl-2-propenoic acid N-hydroxysuccinimide ester was dissolved; and, with a solution in which 2.3 g (5.0 mmol) of L-aspartic acid had been dissolved in 40 ml of a 0.5-N aqueous sodium hydrogencarbon ate solution being added thereto, the mixture was reacted for 4 hours at room temperature. After its pH was adjusted to about 4 with 2-N hydrochloric acid being added thereto, the reaction liquid was concentrated under a reduced pressure as it was. The resulting residue was once dissolved in 20 ml of water, and then was lyophilized in order to eliminate remaining hydrochloric acid. The resulting lyophilized product was refined by a silica gel column chromatography using a moving phase of chloroform/methanol/trifluoroacetic acid at 100/10/0.01 to 40/10/0.01, and then was lyophilized, whereby 0.12 g of the aimed compound was obtained (yield: 45%).

The structure of this compound was verified by $^1$H-NMR and $^{13}$C-NMR.

$^1$H-NMR (heavy dimethyl sulfoxide, δ ppm): 8.43 (1H, d, J=7 Hz, amide group proton), 7.93 (1H, d, J=8 Hz, proton at 4'- or 7'-site of benzocinnamyl aromatic ring), 7.88 (1H, s, proton at 8'-site of benzocinnamyl aromatic ring), 7.87–7.85 (1H, m, proton at 5'- or 6'-site of benzocinnamyl aromatic ring), 7.82 (1H, s, proton at 3-site of propene), 7.56–7.47 (2H, m, proton at 4'- or 7'-site of benzocinnamyl aromatic ring and proton at 5'- or 6'-site of benzocinnamyl aromatic ring), 7.45 (1H, s, proton at 3'-site of benzocinnamyl aromatic ring), 4.85 (1H, t-d, J=7 Hz, J=6 Hz, proton at α-site of aspartic acid portion), 2.93 (1H, d-d, J=6 Hz, J=17 Hz, proton at β-site of aspartic acid portion), 2.81 (1H, d-d, J=6 Hz, J=17 Hz, proton at β-site of aspartic acid portion), 2.08 (3H, s, methyl group proton bound to 2-site of propene); $^{13}$C-NMR (heavy dimethyl sulfoxide, δ ppm): 173.0 (quaternary carbon, carbonyl carbon in aspartic acid portion), 172.4 (quaternary carbon, carbonyl carbon in aspartic acid portion), 168.9 (quaternary carbon, carbonyl carbon at 1-site), 136.2 (quaternary carbon, carbon at 2'-site of benzocinnamyl aromatic ring), 133.0 (quaternary carbon, carbon at 2-site of propene or carbon at 3a'-site of benzocinnamyl aromatic ring), 130.9 (quaternary carbon, carbon at 2-site of propene or carbon at 3a'-site of benzocinnamyl aromatic ring), 128.3 (CH, carbon at 5'- or 6'-site of benzocinnamyl aromatic ring), 127.9 (CH, carbon at 5'- or 6'-site of benzocinnamyl aromatic ring), 127.6 (quaternary carbon, carbon at 7a'-site of benzocinnamyl aromatic ring), 127.2 (CH, carbon at 4'- or 7'-site of benzocinnamyl aromatic ring), 126.2 (CH, carbon at 3-site of propene), 118.0 (CH, carbon at 4'- or 7'-site of benzocinnamyl aromatic ring), 116.1 (quaternary carbon, carbon at 1'-site of benzocinnamyl aromatic ring), 114.2 (CH, carbon at 8'-site of benzocinnamyl aromatic ring), 110.3 (CH, carbon at 3'-site of benzocinnamyl aromatic ring), 49.2 (CH, carbon at α-site of aspartic acid portion), 36.4 (CH$_2$, carbon at β-site of aspartic acid portion), 14.8 (CH$_3$, methyl group carbon bound to 2-site of propene).

Synthesis of (E) N-(o-di-t-butyloxy)-L-aspartic acid 3-(2-amino-benzoylphenyl)-2-methyl-2-propenoic amide Into 20 ml of dimethylformamide, 0.24 g (0.75 mmol) of (E) 3-(2-amino-benzo[d]phenyl)-2-methyl-2-propenoic acid N-hydroxysuccinimide ester was dissolved; and, with 0.28 g (1.0 mmol) of L-aspartic acid di-t-butyl ester hydrochloride (manufactured by Kokusan Chemical Works) being added thereto, the mixture was reacted for 4 hours at room temperature. After the completion of the reaction was verified by TLC, ethyl acetate and water were added thereto. The resulting ethyl acetate layer was fractionated, and the organic layer was washed and then was dried with magnesium sulfate anhydride. Thereafter, the solvent was evaporated under a reduced pressure, and the residue was refined by a silica gel column chromatography (developing solvent: methylene chloride/methanol=95/5), whereby 0.14 g of the aimed compound was obtained (yield: 40%).

The structure of this compound was verified by $^1$H-NMR and $^{13}$C-NMR.

$^1$H-NMR (heavy chloroform, δ ppm): 7.53 (1H, d, J=8 Hz, proton at 4'- or 7'-site of benzocinnamyl aromatic ring), 7.43 (1H, d, J=8 Hz, proton at 4'- or 7'-site of benzocinnamyl aromatic ring), 7.37 (1H, s, proton at 8'-site of benzocinnamyl aromatic ring), 7.37 (1H, s, proton at 3-site of propene), 7.23 (1H, dd, J=7 Hz, J=8 Hz, proton at 5'- or 6'-site of benzocinnamyl aromatic ring), 7.09 (1H, dd, J=7 Hz, J=8 Hz, proton at 5'- or 6'-site of benzocinnamyl aromatic ring), 7.04 (1H, d, J=7 Hz, amide group proton), 6.88 (1H, s, proton at 3'-site of benzocinnamyl aromatic ring), 4.75 (1H, t-d, J=8 Hz, J=4 Hz, methine group proton at α-site of aspartic acid portion), 2.87 (1H, d-d, J=4 Hz, J=17 Hz, methylene group proton at β-site of aspartic acid portion), 2.75 (1H, d-d, J=4 Hz, J=17 Hz, methylene group proton at β-site of aspartic acid portion), 1.97 (3H, s, methyl group proton bound to 2-site of propene), 1.38 (9H, s, methyl group proton of butyl group), 1.35 (9H, s, methyl group proton of butyl group); $^{13}$C-NMR (heavy chloroform, δ ppm): 170.1 (quaternary carbon, carbonyl carbon in aspartic acid portion), 169.7 (quaternary carbon, carbonyl carbon in aspartic acid portion), 168.0 (quaternary carbon, carbonyl carbon at 1-site), 142.8 (quaternary carbon, carbon at 2'-site of benzocinnamyl aromatic ring), 134.4 (quaternary carbon, carbon at 2-site of propene or carbon at 3a'-site of benzocinnamyl aromatic ring), 133.5 (quaternary carbon, carbon at 2-site of propene or carbon at 3a'-site of benzocinnamyl aromatic ring), 131.1 (CH, carbon at 3-site of propene), 128.7 (CH, carbon at 5'- or 6'-site of benzocinnamyl aromatic ring), 127.5 (CH, carbon at 5'- or 6'-site of benzocinnamyl aromatic ring), 127.1 (quaternary carbon, carbon at 7a'-site of benzocinnamyl aromatic ring), 126.2 (CH, carbon at 4'- or 7'-site of benzo cinnamyl aromatic ring), 125.2 (CH, carbon at 4'- or 7'-site of benzocinnamyl aromatic ring), 124.3 (quaternary carbon, carbon at 1'-site of benzocinnamyl aromatic ring), 122.3 (CH, carbon at 8'-site of benzocinnamyl aromatic ring), 108.6 (CH, carbon at 3'-site of benzocinnamyl aromatic ring), 82.2 (quaternary carbon, butyl group), 81.3 (quaternary carbon, butyl group), 49.3 (CH, carbon at α-site of aspartic acid portion), 37.3 (CH$_2$, carbon at β-site of aspartic acid portion), 27.7 (CH$_3$, methyl group carbon of butyl group), 27.6 (CH$_3$, methyl group carbon of butyl group), 13.9 (CH$_3$, methyl group carbon bound to 2-site of propene).

Synthesis of (E) N-(o-di-t-butyloxy)-L-aspartic acid 3-(2-amino-benzo[d]phenyl)-2-methyl-2-propenoic amide Into 2 ml of dimethylformamide, 0.20 g (0.57 mmol) of (E) 3-(2-amino-benzo[d]phenyl)-2-methyl-2-propenoic acid p-nitrophenyl ester and 0.24 g (0.86 mmol) of L-aspartic acid di-t-butyl ester hydrochloride (manufactured by Kokusan Chemical Works) were dissolved; and, with 0.12 ml of triethylamine (manufactured by Wako Pure Chemical Industries, Ltd.) being added thereto, the mixture was reacted for 20 hours at room temperature. After the completion of the reaction was verified by TLC, ethyl acetate and water were added to the reaction solution. The resulting ethyl acetate layer was fractionated, washed several times with a 5% aqueous sodium hydrogencarbon ate solution and then with a saturated aqueous sodium chloride solution, and dried with magnesium sulfate anhydride. Thereafter, the solvent was evaporated under a reduced pressure, and the residue was refined by a silica gel column chromatography (developing solvent: methylene chloride/methanol=95/5), whereby 0.26 g of the aimed compound was obtained (yield: quantitative).

The structure of this compound was verified by $^1$H-NMR and $^{13}$C-NMR.

$^1$H-NMR (heavy chloroform, δ ppm): 7.53 (1H, d, J=8 Hz, proton at 4'- or 7'-site of benzocinnamyl aromatic ring), 7.43 (1H, d, J=8 Hz, proton at 4'- or 7'-site of benzocinnamyl aromatic ring), 7.37 (1H, S, proton at 8'-site of benzocinnamyl aromatic ring), 7.37 (1H, S, proton at 3-site of propene), 7.23 (1H, dd, J=7 Hz, J=8 Hz, proton at 5'- or 6'-site of benzocinnamyl aromatic ring), 7.09 (1H, dd, J=7 Hz, J=8 Hz, proton at 5'- or 6'-site of benzocinnamyl aromatic ring), 7.04 (1H, d, J=7 Hz, amide group proton), 6.88 (1H, s, proton at 3'-site of benzocinnamyl aromatic ring), 4.75 (1H, t-d, J=8 Hz, J=4 Hz, methine group proton at α-site of aspartic acid portion), 2.87 (1H, d-d, J=4 Hz, J=17 Hz, methylene group proton at β-site of aspartic acid portion), 2.75 (1H, d-d, J=4 Hz, J=17 Hz, methylene group proton at 3-site of aspartic acid portion), 1.97 (3H, s, methyl group proton bound to 2-site of propene), 1.38 (9H, s, methyl group proton of butyl group), 1.35 (9H, s, methyl group proton of butyl group); $^{13}$C-NMR (heavy chloroform, δ ppm): 170.1 (quaternary carbon, carbonyl carbon in aspartic acid portion), 169.7 (quaternary carbon, carbonyl carbon in aspartic acid portion), 168.0 (quaternary carbon, carbonyl carbon at 1-site), 142.8 (quaternary carbon, carbon at 2'-site of benzocinnamyl aromatic ring), 134.4 (quaternary carbon, carbon at 2-site of propene or,carbon at 3a'-site of benzocinnamyl aromatic ring), 133.5 (quaternary carbon, carbon at 2-site of propene or carbon at 3a'-site of benzocinnamyl aromatic ring), 131.1 (CH, carbon at 3-site of propene), 128.7 (CH, carbon at 5'- or 6'-site of benzocinnamyl aromatic ring), 127.5 (CH, carbon at 5'- or 6'-site of benzocinnamyl aromatic ring), 127.1 (quaternary carbon, carbon at 7a'-site of benzocinnamyl aromatic ring), 126.2 (CH, carbon at 4'- or 7'-site of benzocinnamyl aromatic ring), 125.2 (CH, carbon at 4'- or 7'-site of benzocinnamyl aromatic ring), 124.3 (quaternary carbon, carbon at 1'-site of benzocinnamyl aromatic ring), 122.3 (CH, carbon at 8'-site of benzocinnamyl aromatic ring), 108.6 (CH, carbon at 3'-site of benzocinnamyl aromatic ring), 82.2 (quaternary carbon, butyl group), 81.3 (quaternary carbon, butyl group), 49.3 (CH, carbon at α-site of aspartic acid portion), 37.3 (CH$_2$, carbon at β-site of aspartic acid portion), 27.7 (CH$_3$, methyl group carbon of butyl group), 27.6 (CH$_3$, methyl group carbon of butyl group), 13.9 (CH$_3$, methyl group carbon bound to 2-site of propene).

Synthesis of (E) N-L-aspartic acid $^3$-(2-amino-benzo[d]phenyl)-2-methyl-2-propenoic amide Into chloroform containing 10% trifluoroacetic acid, 0.26 g (0.57 mmol) of (E) N-(o-di-t-butyloxy)-L-aspartic acid 3-(2-amino-benzo[d]phenyl)-2-methyl-2-propenoic amide was dissolved; and a de-protecting reaction was carried out for 3 hours at room temperature. After the completion of the reaction was verified by TLC, concentration under a reduced pressure and drying were effected, whereby 0.20 g of the aimed compound was obtained (yield: quantitative).

The structure of this compound was verified by $^1$H-NMR and $^{13}$C-NMR.

$^1$H-NMR (heavy dimethyl sulfoxide, δ ppm): 8.43 (1H, d, J=7 Hz, amide group proton), 7.93 (1H, d, J=8 Hz, proton at 4'- or 7'-site of benzocinnamyl aromatic ring), 7.88 (1H, s, proton at 8'-site of benzocinnamyl aromatic ring), 7.87–7.85 (1H, m, proton at 5'- or 6'-site of benzocinnamyl aromatic ring), 7.82 (1H, s, proton at 3-site of propene), 7.56–7.47 (2H, m, proton at 4'- or 7'-site of benzocinnamyl aromatic ring and proton at 5'- or 6'-site of benzocinnamyl aromatic ring), 7.45 (1H, s, proton at 3'-site of benzocinnamyl aromatic ring), 4.85 (1H, t-d, J=7 Hz, J=6 Hz, proton at α-site of aspartic acid portion), 2.93 (1H, d-d, J=6 Hz, J=17 Hz, proton at 8-site of aspartic acid portion), 2.81 (1H, d-d, J=6 Hz, J=17 Hz, proton at β-site of aspartic acid portion), 2.08 (3H, s, methyl group proton bound to 2-site of propene); $^{13}$C-NMR (heavy dimethyl sulfoxide, δ ppm): 173.0 (quaternary carbon, carbonyl carbon in aspartic acid portion), 172.4 (quaternary carbon, carbonyl carbon in aspartic acid portion), 168.9 (quaternary carbon, carbonyl carbon at 1-site), 136.2 (quaternary carbon, carbon at 2'-site of benzocinnamyl aromatic ring), 133.0 (quaternary carbon, carbon at 2-site of propene or carbon at 3a'-site of benzocinnamyl aromatic ring), 130.9 (quaternary carbon, carbon at 2-site of propene or carbon at 3a'-site of benzocinnamyl aromatic ring), 128.3 (CH, carbon at 5'- or 6'-site of benzocinnamyl aromatic ring), 127.9 (CH, carbon at 5'- or 6'-site of benzocinnamyl aromatic ring), 127.6 (quaternary carbon, carbon at 7a'-site of benzocinnamyl aromatic ring), 127.2 (CH, carbon at 4'- or 7'-site of benzocinnamyl aromatic ring), 126.2 (CH, carbon at 3-site of propene), 118.0 (CH, carbon at 4'- or 7'-site of benzocinnamyl aromatic ring), 116.1 (quaternary carbon,carbon at 1'-site of benzocinnamyl aromatic ring), 114.2 (CH, carbon at 8'-site of benzocinnamyl aromatic ring), 110.3 (CH, carbon at 3'-site of benzocinnamyl aromatic ring), 49.2 (CH, carbon at α-site of aspartic acid portion), 36.4 (CH$_2$, carbon at β-site of aspartic acid portion), 14.8 (CH$_3$, methyl group carbon bound to 2-site of propene).

Synthesis of (E) N-3-carboxypropyl 3-(2-amino-benzo[d]phenyl)-2-methyl-2-propenoic amide Into 20 ml of dimethylformamide, 0.24 g (0.75 mmol) of (E) 3-(2-amino-benzo[d]phenyl)-2-methyl-2-propenoic acid N-hydroxysuccinimide ester was dissolved; and, with a solution in which 0.52 g (5.0 mmol) of 7-amino-n-butyric acid (manufactured by Wako Pure Chemical Industries, Ltd.) had been dissolved in 40 ml of a 0.5-N aqueous sodium hydrogencarbon ate solution being added thereto, the mixture was reacted for 4 hours at room temperature. After its pH was adjusted to about 4 with 2-N hydrochloric acid being added thereto, the reaction liquid was concentrated under a reduced pressure as it was. The resulting residue was once dissolved in 20 ml of water, and then was lyophilized in order to eliminate remaining hydrochloric acid. The resulting lyophilized product was refined by a silica gel column chromatography using a moving phase of chloroform/methanol/trifluoroacetic acid at 100/10/0.01 to 40/10/0.01, and then was lyophilized, whereby 0.17 g of the aimed compound was obtained (yield: 74%). The structure of this compound was verified by $^1$H-NMR and $^{13}$C-NMR.

$^1$H-NMR (heavy dimethylsulfoxide, δ ppm): 8.52 (1H, bs, amide group proton), 7.97–7.88 (4H, m, protons at 5'- and 6'-sites of benzocinnamyl aromatic ring, proton at 4'- or 7'-site of benzocinnamyl aromatic ring, and proton at 8'-site of benzocinnamyl aromatic ring), 7.58–7.48 (2H, m, proton at 4'- or 7'-site of benzocinnamyl aromatic ring and proton at 3'-site of benzocinnamyl aromatic ring), 7.39 (1H, s, proton at 3-site of propene), 3.25 (2H, t, J=7 Hz, methylene group proton at γ-site of GABA portion), 2.33 (2H, t, J=7 Hz, methylene group proton at α-site of GABA portion), 2.00 (3H, s, methyl group proton bound to 2-site of propene), 1.79 (2H, t-t, J=7 Hz, J=7 Hz, methylene group proton at β-site of GABA portion); $^{13}$C-NMR (heavy dimethyl sulfoxide, δ ppm): 174.2 (quaternary carbon, carbonyl carbon in GABA portion), 169.1 (quaternary carbon, carbonyl carbon at 1-site), 136.7 (quaternary carbon, carbon at 2'-site of benzocinnamyl aromatic ring), 132.1 (quaternary carbon, carbon at 2-site of propene or carbon at 3a'-site of benzocinnamyl aromatic ring), 130.8 (quaternary carbon, carbon at 2-site of propene or carbon at 3a'-site of benzocinnamyl aromatic ring), 129.5 (CH, carbon at 5'- or 6'-site of benzocinnamyl aromatic ring), 127.9 (CH, carbon at 5'- or 6'-site of benzocinnamyl aromatic ring), 128.0 (quaternary carbon, carbon at 7a'-site of benzocinnamyl aromatic ring), 127.1 (CH, carbon at 4'- or 7'-site of benzocinnamyl aromatic ring), 126.4 (CH, carbon at 3-site of propene), 126.9 (CH, carbon at 4'- or 7'-site of benzocinnamyl aromatic ring), 125.9 (quaternary carbon, carbon at 1'-site of benzocinnamyl aromatic ring), 126.1 (CH, carbon at 8'-site of benzocinnamyl aromatic ring), 115.5 (CH, carbon at 3'-site of benzocinnamyl aromatic ring), 38.4 (CH$_2$, methylene group carbon at γ-site of GABA portion), 31.3 (CH$_2$, methylene group carbon at α-site of GABA portion), 24.5 (CH$_2$, methylene group carbon at β-site of GABA portion), 14.8 (CH$_3$, methyl group carbon bound to 2-site of propene).

Synthesis of (E) N-3-methyloxycarbonylpropyl 3-(2-amino-benzor[d]phenyl)-2-methyl-2-propenoic amide Into 20 ml of dimethylformamide, 0.24 g (0.75 mmol) of (E) 3-(2-amino-benzo[d]phenyl)-2-methyl-2-propenoic acid N-hydroxysuccinimide ester was dissolved; and, with 0.15 g (1.0 mmol) of γ-aminobutanoic acid methyl ester hydrochloride (manufactured by Nakalai Tesque, Inc.) being added thereto, the mixture was reacted for 6 hours at room temperature. After the completion of the reaction was verified by TLC, ethyl acetate and water were added to the reaction solution. The resulting ethyl acetate layer was fractionated; and the organic layer was washed and then dried with magnesium sulfate anhydride. Thereafter, the solvent was evaporated under a reduced pressure, and the residue was refined by a silica gel column chromatography (developing solvent: methylene chloride/methanol=95/5), whereby 0.17 g of the aimed compound was obtained (yield: 69%).

The structure of this compound was verified by $^1$H-NMR and $^{13}$C-NMR.

$^1$H-NMR (heavy chloroform, δ ppm): 7.82–7.46 (3H, m, protons at 5- and 6'-sites of benzocinnamyl aromatic ring and proton at 4'- or 7'-site of benzocinnamyl aromatic ring), 7.38 (1H, s, proton at 3-site of propene), 7.33 (1H, d, d=8 Hz, proton at 4'- or 7'-site of benzocinnamyl aromatic ring), 7.23–7.17 (1H, m, proton at 8'-site of benzocinnamyl aromatic ring), 6.99 (1H, s, proton at 3'-site of benzocinnamyl aromatic ring), 6.61 (1H, bs, amide group proton), 3.98 (2H, bs, amino group proton), 3.67 (3H, s, methyl group carbon of methyl ester in GABA portion), 3.42 (2H, t, J=7 Hz, methylene group proton at γ-site of GABA portion), 2.42 (2H, t, J=7 Hz, methylene group proton at α-site of GABA portion), 1.92 (2H, t-t, J=7 Hz, J=7 Hz, methylene group proton at β-site of GABA portion), 2.03 (3H, s, methyl group proton bound to 2-site of propene).

$^{13}$C-NMR (heavy chloroform, δ ppm): 174.1 (quaternary carbon, carbonyl carbon in GABA portion), 169.1 (quaternary carbon, carbonyl carbon at 1-site), 142.8 (quaternary carbon, carbon at 2'-site of benzocinnamyl aromatic ring), 134.5 (quaternary carbon, carbon at 2-site of propene or carbon at 3a'-site of benzocinnamyl aromatic ring), 134.3 (quaternary carbon, carbon at 2-site of propene or carbon at 3a'-site of benzocinnamyl aromatic ring), 130.2 (CH, carbon at 3-site of propene), 128.8 (CH, carbon at 5'- or 6'-site of benzocinnamyl aromatic ring), 127.6 (CH, carbon at 5'- or 6'-site of benzocinnamyl aromatic ring), 127.3 (quaternary carbon, carbon at 7a'-site of benzocinnamyl aromatic ring), 126.4 (CH, carbon at 4'- or 7'-site of benzocinnamyl aromatic ring), 125.3 (CH, carbon at 4'- or 7'-site of benzocinnamyl aromatic ring), 124.6 (quaternary carbon, carbon at 1'-site of benzocinnamyl aromatic ring), 122.5 (CH, carbon at 8'-site of benzocinnamyl aromatic ring), 108.8 (CH, carbon at 3'-site of benzocinnamyl aromatic ring), Ad 51.7 (CH$_3$, methyl group carbon of methyl ester in GABA portion), 39.6 (CH$_2$, methylene group carbon at γ-site of GABA portion), 31.7 (CH$_2$, methylene group carbon at α-site of GABA portion), 24.3 (CH$_2$, methylene group carbon at β-site of GABA portion), 14.2 (CH$_3$, methyl group carbon bound to 2-site of propene).

Synthesis of (E) N-3-methyloxycarbonylpropyl 3-(2-amino-benzo[d]phenyl)-2-methyl-2-propenoic amide Into 1 ml of dimethylformamide, 0.17 g (0.48 mmol) of (E) 3-(2-amino-benzo[d]phenyl)-2-methyl-2-propenoic acid p-nitrophenyl ester and 0.089 g (0.58 mmol) of γ-aminobutanoic acid methyl ester hydrochloride (manufactured by Nakalai Tesque, Inc.) were dissolved; and, with 0.08 ml of triethylamine (manufactured by Wako Pure Chemical Industries, Ltd.) being added thereto, the mixture was reacted for 20 hours at room temperature. After the completion of the reaction was verified by TLC, ethyl acetate and water were added to the reaction solution. The resulting ethyl acetate layer was fractionated, washed several times with a 5% aqueous sodium hydrogencarbon ate solution and then with a saturated aqueous sodium chloride solution, and dried with magnesium sulfate anhydride. Thereafter, the solvent was evaporated under a reduced pressure, and the residue was refined by a silica gel column chromatography (developing solvent: methylene chloride/methanol=95/5), whereby 0.16 g of the aimed compound was obtained (yield: quantitative).

The structure of this compound was verified by $^1$H-NMR and $^{13}$C-NMR.

$^1$H-NMR (heavy chloroform, δ ppm): 7.82–7.46 (3H, m, protons at 5'- and 6'-sites of benzocinnamyl aromatic ring and proton at 4'- or 7'-site of benzocinnamyl aromatic ring), 7.38 (1H, s, proton at 3-site of propene), 7.33 (1H, d, d=8 Hz, proton at 4'- or 7'-site of benzocinnamyl aromatic ring), 7.23–7.17 (1H, m, proton at 8'-site of benzocinnamyl aromatic ring), 6.99 (1H, s, proton at 3'-site of benzocinnamyl aromatic ring), 6.61 (1H, bs, amide group proton), 3.98 (2H, bs, amino group proton), 3.67 (3H, s, methylene group proton of methyl ester in GABA portion), 3.42 (2H, t, J=7 Hz, methylene group proton at γ-site of GABA portion), 2.42 (2H, t, J=7 Hz, methylene group proton at α-site of GABA portion), 1.92 (2H, t-t, J=7 Hz, J=7 Hz, methylene group proton at γ-site of GABA portion), 2.03 (3H, s, methyl group proton bound to 2-site of propene); 13C-NMR (heavy chloroform, δ ppm): 174.1 (quaternary carbon, carbonyl carbon in GABA portion), 169.1 (quaternary carbon, carbonyl carbon at 1-site), 142.8 (quaternary carbon, carbon at 2'-site of benzocinnamyl aromatic ring), 134.5 (quaternary carbon, carbon at 2-site of propene or carbon at 3a'-site of benzocinnamyl aromatic ring), 134.3 (quaternary carbon, carbon at 2-site of propene or carbon at 3a'-site of benzocinnamyl aromatic ring), 130.2 (CH, carbon at 3-site of propene), 128.8 (CH, carbon at 5'- or 6'-site of benzocinnamyl aromatic ring), 127.6 (CH, carbon at 5'- or 6'-site of benzocinnamyl aromatic ring), 127.3 (quaternary carbon, carbon at 7a'-site of benzocinnamyl aromatic ring), 126.4 (CH, carbon at 4'- or 7'-site of benzocinnamyl aromatic ring), 125.3 (CH, carbon at 4'- or 7'-site of benzocinnamyl aromatic ring), 124.6 (quaternary carbon, carbon at 1'-site of benzocinnamyl aromatic ring), 122.5 (CH, carbon at 8'-site of benzocinnamyl aromatic ring), 108.8 (CH, carbon at 3'-site of benzocinnamyl aromatic ring), 51.7 ($CH_3$, methyl group carbon of methyl ester in GABA portion), 39.6 ($CH_2$, methylene group carbon at γ-site of GABA portion), 31.7 ($CH_2$, methylene group carbon at α-site of GABA portion), 24.3 ($CH_2$, methylene group carbon at β-site of GABA portion), 14.2 ($CH_3$, methyl group carbon bound to 2-site of propene).

Synthesis of (E) N-3-carboxypropyl 3-(2-amino-benzor[d]phenyl)-2-methyl-2-propenoic amide Into 1 ml of methanol, 0.16 g (0.48 mmol) of (E) N-3-methyloxycarbonylpropyl 3-(2-amino-benzo[d]phenyl)-2-methyl-2-propenoic amide was dissolved; and, with 1 ml of a 1-N aqueous sodium hydroxide solution being added thereto, the mixture was reacted for 4 hours at 40° C. After the pH in the system was adjusted to about 4 with 1-N hydrochloric acid, the reaction solvent was evaporated under a reduced pressure, and the residue was refined by a silica gel column chromatography (developing solvent: dichloromethane/methanol=10/3), whereby 0.15 g of the aimed compound was obtained (yield: quantitative).

The structure of this compound was verified by $^1$H-NMR and $^{13}$C-NMR.

$^1$H-NMR (heavy dimethylsulfoxide, δ ppm): 8.52 (1H, bs, amide group proton), 7.97–7.88 (4H, m, protons at 5'- and 6'-sites of benzocinnamyl aromatic ring, proton at 4'- or 7'-site of benzocinnamyl aromatic ring, and proton at 8'-site of benzocinnamyl aromatic ring), 7.58–7.48 (2H, m, proton at 4'- or 7'-site of benzocinnamyl aromatic ring and proton at 3'-site of benzocinnamyl aromatic ring), 7.39 (1H, s, proton at 3-site of propene), 3.25 (2H, t, J=7 Hz, methylene group proton at γ-site of GABA portion), 2.33 (2H, t, J=7 Hz, methylene group proton at α-site of GABA portion), 2.00 (3H, s, methyl group proton bound to 2-site of propene), 1.79 (2H, t-t, J=7 Hz, J=7 Hz, methylene group proton at β-site of GABA portion); 13C-NMR (heavy dimethyl sulfoxide, δ ppm): 174.2 (quaternary carbon, carbonyl carbon in GABA portion), 169.1 (quaternary carbon, carbonyl carbon at 1-site), 136.7 (quaternary carbon, carbon at 2'-site of benzocinnamyl aromatic ring), 132.1 (quaternary carbon, carbon at 2-site of propene or carbon at 3a'-site of benzocinnamyl aromatic ring), 130.8 (quaternary carbon, carbon at 2-site of propene or carbon at 3a'-site of benzocinnamyl aromatic ring), 129.5 (CH, carbon at 5'- or 6'-site of benzocinnamyl aromatic ring), 127.9 (CH, carbon at 5'- or 6'-site of benzocinnamyl aromatic ring), 128.0 (quaternary carbon, carbon at 7a'-site of benzocinnamyl aromatic ring), 127.1 (CH, carbon at 4'- or 7'-site of benzocinnamyl aromatic ring), 126.4 (CH, carbon at 3-site of propene), 126.9 (CH, carbon at 4'- or 7'-site of benzocinnamyl aromatic ring), 125.9 (quaternary carbon, carbon at 1'-site of benzocinnamyl aromatic ring), 126.1 (CH, carbon at 8'-site of benzocinnamyl aromatic ring), 115.5 (CH, carbon at 3'-site of benzocinnamyl aromatic ring), 38.4 ($CH_2$, methylene group carbon at γ-site of GABA portion), 31.3 ($CH_2$, methylene group carbon at α-site of GABA portion), 24.5 ($CH_2$, methylene group carbon at β-site of GABA portion), 14.8 ($CH_3$, methyl group carbon bound to 2-site of propene).

Synthesis of (E) N-(o-di-t-butyloxy)-L-glutamic acid 3-(2-amino-4-chlorophenyl)-2-methyl-2-propenoic amide Into 2 ml of dimethylformamide, 0.20 g (0.60 mmol) of (E) 3-(2-amino-4-chlorophenyl)-2-methyl-2-propenoic acid p-nitrophenyl ester and 0.21 g (0.72 mmol) of L-glutamic acid di-t-butyl ester hydrochloride (Sigma Chemical Co.) were dissolved; and, with 0.10 ml of triethylamine (manufactured by Wako Pure Chemical Industries, Ltd.) being added thereto, the mixture was reacted for 20 hours at room temperature. After the completion of the reaction was verified by TLC, ethyl acetate and water were added thereto. The resulting ethyl acetate layer was fractionated, washed several times with a 5% aqueous sodium hydrogencarbonate solution and then with a saturated aqueous sodium chloride solution, and dried with magnesium sulfate anhydride. Thereafter, the solvent was evaporated under a reduced pressure, and the residue was refined by a silica gel column chromatography (developing solvent: methylene chloride/methanol=95/5), whereby 0.27 g of the aimed compound was obtained (yield: quantitative).

The structure of this compound was verified by $^1$H-NMR and $^{13}$C-NMR.

$^1$H-NMR (heavy chloroform, δ ppm): 7.78 (1H, d, J=8 Hz, amide group proton), 7.22 (1H, s, proton at 3-site of propene), 6.93 (1H, d, J=8 Hz, proton at 6'-site of cinnamyl aromatic ring), 6.68 (1H, s, proton at 3'-site of cinnamyl aromatic ring), 6.65 (1H, d, J=8 Hz, proton at 5'-site of cinnamyl aromatic ring), 4.52–4.45 (1H, m, proton at α-site of glutamic acid portion), 2.51–2.42 (2H, m, proton at γ-site of glutamic acid portion), 2.25–2.04 (2H, m, proton at β-site of glutamic acid portion), 1.99 (3H, s, methyl group proton bound to 2-site of propene), 1.49 (9H, s, methyl group proton of butyl group), 1.46 (9H, s, methyl group proton of butyl group); $^{13}$C-NMR (heavy chloroform, δ ppm): 171.3 (quaternary carbon, carbonyl carbon in glutamic acid portion), 170.1 (quaternary carbon, carbonyl carbon in glutamic acid portion), 169.8 (quaternary carbon, carbonyl carbon at 1-site of propene), 146.1 (quaternary carbon, carbon at 2'-site of cinnamyl aromatic ring), 134.4 (quaternary carbon, carbon at 4'-site of cinnamyl aromatic ring), 132.4 (quaternary carbon, carbon at 2-site of propene), 130.4 (CH, carbon at 6'-site of cinnamyl aromatic ring), 130.1 (CH, carbon at 3-site of propene), 118.9 (quaternary carbon, carbon at 1'-site of cinnamyl aromatic ring), 117.3 (CH, carbon at 5'-site of cinnamyl aromatic ring), 114.8 (CH, carbon at 3'-site of cinnamyl aromatic ring), 82.4 (quaternary carbon, butyl group), 81.1 (quaternary carbon, butyl group), 53.2 (CH, carbon at α-site of glutamic acid portion), 31.5 ($CH_2$, carbon at γ-site of glutamic acid portion), 26.9 ($CH_2$, carbon at β-site of glutamic acid portion), 27.7 ($CH_3$, methyl group carbon of butyl group), 13.9 ($CH_3$, methyl group carbon bound to 2-site of propene).

Synthesis of (E) N-L-glutamic acid 3-(2-amino-4-chlorophenyl)-2-methyl-2-propenoic amide In chloroform containing 5% trifluoroacetic acid, 0.27 g (0.60 mmol) of (E) N-(o-di-t-butyloxy)-L-glutamic acid 3-(2-amino-4-chlorophenyl)-2-methyl-2-propenoic amide was dissolved; and a de-protecting reaction was carried out for 5 hours at room temperature. After the completion of the reaction was verified by TLC, concentration under a reduced pressure and drying were effected, whereby 0.20 g of the aimed compound was obtained (yield: quantitative).

The structure of this compound was verified by $^1$H-NMR and $^{13}$C-NMR.

$^1$H-NMR (heavy dimethyl sulfoxide, δ ppm): 8.39 (1H, d, J=7 Hz, amide group proton), 7.11 (1H, d, J=8 Hz, proton at 6'-site of cinnamyl aromatic ring), 7.05 (1H, s, proton at 3-site of propene), 6.93 (1H, s, proton at 3'-site of cinnamyl aromatic ring), 6.77 (1H, d, J=8 Hz, proton at 5'-site of cinnamyl aromatic ring), 4.34 (1H, t-d, J=12 Hz, J=5 Hz, proton at α-site of glutamic acid portion), 2.29 (2H, t, J=7 Hz, proton at γ-site of glutamic acid portion), 2.19–1.97 (2H, m, proton at β-site of glutamic acid portion), 1.93 (3H, s, methyl group proton bound to 2-site of propene); $^{13}$C-NMR (heavy dimethyl sulfoxide, δ ppm): 174.1 (quaternary carbon, carbonyl carbon in glutamic acid portion), 173.6 (quaternary carbon, carbonyl carbon in glutamic acid portion), 169.2 (quaternary carbon, carbonyl carbon at 1-site of propene), 145.1 (quaternary carbon, carbon at 2'-site of cinnamyl aromatic ring), 133.4 (quaternary carbon, carbon at 4'-site of cinnamyl aromatic ring), 133.0 (quaternary carbon, carbon at 2-site of propene), 130.9 (CH, carbon at 6'-site of cinnamyl aromatic ring), 127.6 (CH, carbon at 3-site of propene), 120.8 (CH, carbon at 5'-site of cinnamyl aromatic ring), 117.0 (quaternary carbon, carbon at 1'-site of cinnamyl aromatic ring), 115.6 (CH, carbon at 3'-site of cinnamyl aromatic ring), 52.1 (CH, carbon at α-site of glutamic acid portion), 31.5 (CH$_2$ carbon at γ-site of glutamic acid portion), 26.5 (CH$_2$, carbon at α-site of glutamic acid portion), 14.4 (CH$_3$, methyl group carbon bound to 2-site of propene).

Synthesis of (E) N-3-methyloxycarbonylpropyl 3-(2-amino-4-chlorophenyl)-2-methyl-2-propenoic amide Into 2 ml of dimethylformamide, 0.20 g (0.60 mmol) of (E) 3-(2-amino-4-chlorophenyl)-2-methyl-2-propenoic acid p-nitrophenyl ester and 0.11 g (0.72 mmol) of γ-aminobutanoic acid methyl ester hydrochloride (manufactured by Nakalai Tesque, Inc.) were dissolved; and, with 0.10 ml of triethylamine (manufactured by Wako Pure Chemical Industries, Ltd.) being added thereto, the mixture was reacted for 20 hours at room temperature. After the completion of the reaction was verified by TLC, ethyl acetate and water were added thereto. The resulting ethyl acetate layer was fractionated, washed several times with a 5% aqueous sodium hydrogencarbonate solution and then with a saturated aqueous sodium chloride solution, and dried with magnesium sulfate anhydride. Thereafter, the solvent was evaporated under a reduced pressure, and the residue was refined by a silica gel column chromatography (developing solvent: methylene chloride/methanol=95/5), whereby 0.19 g of the aimed compound was obtained (yield: quantitative).

The structure of this compound was verified by $^1$H-NMR and $^{13}$C-NMR.

$^1$H-NMR (heavy chloroform, δ ppm): 7.22 (1H, s, proton at 3-site of propene), 7.08 (1H, bs, amide group proton), 6.94 (1H, d, J=8 Hz, proton at 6'-site of cinnamyl aromatic ring), 6.69 (1H, s, proton at 3'-site of cinnamyl aromatic ring), 6.67 (1H, d, J=8 Hz, proton at 5'-site of cinnamyl aromatic ring), 3.66 (3H, s, methyl group proton of methyl ester in GABA portion), 3.44 (2H, t, J=7 Hz, methylene group proton at γ-site of GABA portion), 2.44 (2H, t, J=7 Hz, methylene group proton at α-site of GABA portion), 2.00 (3H, s, methyl group proton bound to 2-site of propene), 1.94 (2H, t-t, J=7 Hz, J=7 Hz, methylene group proton at α-site of GABA portion); $^{13}$C-NMR (heavy chloroform, δ ppm): 174.3 (quaternary carbon, carbonyl carbon in GABA portion), 170.2 (quaternary carbon, carbonyl carbon at 1-site of propene), 146.1 (quaternary carbon, carbon at 2'-site of cinnamyl aromatic ring), 134.6 (quaternary carbon, carbon at 4'-site of cinnamyl aromatic ring), 132.8 (quaternary carbon, carbon at 2-site of propene), 130.6 (CH, carbon at 6'-site of cinnamyl aromatic ring), 130.2 (CH, carbon at 3-site of propene), 119.2 (quaternary carbon, carbon at 1'-site of cinnamyl aromatic ring), 117.6 (CH, carbon at 5'-site of cinnamyl aromatic ring), 115.0 (CH, carbon at 3'-site of cinnamyl aromatic ring), 51.8 (CH$_3$, methyl group carbon of methyl ester in GABA portion), 39.9 (CH$_2$: methylene group carbon at γ-site of GABA portion), 31.7 (CH$_2$, methylene group carbon at α-site of GABA portion), 24.1 (CH$_2$, methylene group carbon at β-site of GABA portion), 14.2 (CH$_3$, methyl group carbon bound to 2-site of propene).

Synthesis of (E) N-3-carboxypropyl 3-(2-amino-4-chlorophenyl)-2-methyl-2-propenoic amide Into 1 ml of methanol, 0.23 g (0.75 mnol) of (E) N-3-methyloxycarbonylpropyl 3-(2-amino-4-chlorophenyl)-2-methyl-2-propenoic amide was dissolved; and, with 1 ml of a 1-N aqueous sodium hydroxide solution being added thereto, the mixture was reacted for 12 hours at room temperature. After the pH of the reaction liquid was adjusted to about 4 with 1-N hydrochloric acid, the solvent was evaporated under a reduced pressure, and the residue was refined by a silica gel column chromatography (developing solvent: dichloromethane/methanol=10/1), whereby 0.22 g of the aimed compound was obtained (yield: quantitative).

The structure of this compound was verified by $^1$H-NMR and $^{13}$C-NMR.

$^1$H-NMR (heavy dimethyl sulfoxide, δ ppm): 8.31 (1H, bs, amide group proton), 6.99 (1H, d, J=8 Hz, proton at 6'-site of cinnamyl aromatic ring), 6.94 (1H, s, proton at 3-site of propene), 6.76 (1H, s, proton at 3'-site of cinnamyl aromatic ring), 6.55 (1H, d, J=8 Hz, proton at 5'-site of cinnamyl aromatic ring), 3.24 (2H, t, J=7 Hz, methylene group proton at γ-site of GABA portion), 2.29 (2H, t, J=7 Hz, methylene group proton at α-site of GABA portion), 1.91 (3H, s, methyl group proton bound to 2-site of propene), 1.79 (2H, t-t, J=7 Hz, J=7 Hz, methylene group proton at 13-site of GABA portion); $^{13}$C-NMR (heavy dimethyl sulfoxide, δ ppm): 175.3 (quaternary carbon, carbonyl carbon in GABA portion), 169.5 (quaternary carbon, carbonyl carbon at 1-site of propene), 148.3 (quaternary carbon, carbon at 2'-site of cinnamyl aromatic ring), 133.4 (quaternary carbon, carbon at 4'-site of cinnamyl aromatic ring), 133.0 (quaternary carbon, carbon at 2-site of propene), 130.7 (CH, carbon at 6'-site of cinnamyl aromatic ring), 127.4 (CH, carbon at 3-site of propene), 118.6 (quaternary carbon, carbon at 1'-site of cinnamyl aromatic ring), 115.0 (CH, carbon at 5'-site of cinnamyl aromatic ring), 113.7 (CH, carbon at 3'-site of cinnamyl aromatic ring), 38.8 (CH$_2$, methylene group carbon at γ-site of GABA portion), 32.2 (CH$_2$, methylene group carbon at α-site of GABA portion), 25.0 (CH$_2$, methylene group carbon at β-site of GABA portion), 14.7 (CH$_3$, methyl group carbon bound to 2-site of propene).

Synthesis of (E) N-(o-di-t-butyloxy)-L-aspartic acid 3-(2-amino-4-chlorophenyl)-2-methyl-2-propenoic amide Into 2 ml of dimethylformamide, 0.20 g (0.60 mmol) of (E) 3-(2-amino-4-chlorophenyl)-2-methyl-2-propenoic acid p-nitrophenyl ester and 0.20 g (0.72 mmol) of L-aspartic acid di-t-butyl ester hydrochloride (manufactured by Kokusan Chemical Works) were dissolved; and, with 0.10 ml of triethylamine (manufactured by Wako Pure Chemical Industries, Ltd.) being added thereto, the mixture was reacted for 20 hours at room temperature. After the completion of the reaction was verified by TLC, ethyl acetate and water were added thereto. The resulting ethyl acetate layer was fractionated, washed several times with a 5% aqueous sodium hydrogencarbon ate solution and then with a saturated aqueous sodium chloride solution, and dried with magnesium sulfate anhydride. Thereafter, the solvent was evaporated under a reduced pressure, and the residue was refined by a silica gel column chromatography (developing solvent: methylene chloride/methanol=95/5), whereby 0.26 g of the aimed compound was obtained (yield: quantitative).

The structure of this compound was verified by $^1$H-NMR and $^{13}$C-NMR.

$^1$H-NMR (heavy chloroform, δ ppm): 7.31 (1H, s, proton at 3-site of propene), 7.22 (1H, d, J=8 Hz, amide group proton), 6.96 (1H, d, J=9 Hz, proton at 6'-site of cinnamyl aromatic ring), 6.71 (1H, s, proton at 3'-site of cinnamyl aromatic ring), 6.70 (1H, d, J=9 Hz, proton at 5'-site of cinnamyl aromatic ring), 4.83 (1H, t-d, J=8 Hz, J=4 Hz, proton at α-site of aspartic acid portion), 2.99 (1H, d-d, J=4 Hz, J=17 Hz, proton at 1-site of aspartic acid portion), 2.84 (1H, d-d, J=4 Hz, J=17 Hz, proton at 1-site of aspartic acid portion), 2.03 (3H, s, methyl group proton bound to 2-site of propene), 1.49 (9H, s, methyl group proton of butyl group), 1.47 (9H, s, methyl group proton of butyl group) $^3$C-NMR (heavy chloroform, δ ppm): 170.3 (quaternary carbon, carbonyl carbon in aspartic acid portion), 169.7 (quaternary carbon, carbonyl carbon in aspartic acid portion), 168.7 (quaternary carbon, carbonyl carbon at 1-site of propene), 145.9 (quaternary carbon, carbon at 2'-site of cinnamyl aromatic ring), 134.6 (quaternary carbon, carbon at 4'-site of cinnamyl aromatic ring), 132.3 (quaternary carbon, carbon at 2-site of propene), 130.9 (CH, carbon at 3-site of propene), 130.5 (CH, carbon at 6'-site of cinnamyl aromatic ring), 119.1 (quaternary carbon, carbon at 1'-site of cinnamyl aromatic ring), 117.6 (CH, carbon at 5'-site of cinnamyl aromatic ring), 114.9 (CH, carbon at 3'-site of cinnamyl aromatic ring), 82.7 (quaternary carbon, butyl group), 81.8 (quaternary carbon, butyl group), 49.6 (CH, carbon at α-site of aspartic acid portion), 37.2 (CH$_2$, carbon at 8-site of aspartic acid portion), 27.9 (CH$_3$, methyl group carbon of butyl group), 27.7 (CH$_3$, methyl group carbon of butyl group), 13.9 (CH$_3$, methyl group carbon bound to 2-site of propene).

Synthesis of (E) N-L-aspartic acid 3-(2-amino-4-chlorophenyl)-2-methyl-2-propenoic amide Into chloroform containing 5% trifluoroacetic acid, 0.26 g (0.60 mmol) of (E) N-(o-di-t-butyloxy)-L-aspartic acid 3-(2-amino-4-chlorophenyl)-2-methyl-2-propenoic amide was dissolved; and a de-protecting reaction was carried out for 6 hours at room temperature. After the completion of the reaction was verified by TLC, concentration under a reduced pressure and drying were effected, whereby 0.20 g of the aimed compound was obtained (yield: quantitative).

The structure of this compound was verified by $^1$H-NMR and $^{13}$C-NMR.

$^1$H-NMR (heavy dimethyl sulfoxide, δ ppm): 8.39 (1H, d, J=8 Hz, amide group proton), 7.08 (1H, d, J=9 Hz, proton at 6'-site of cinnamyl aromatic ring), 7.01 (1H, s, proton at 3-site of propene), 6.89 (1H, s, proton at 3'-site of cinnamyl aromatic ring), 6.74 (1H, d, J=9 Hz, proton at 5'-site of cinnamyl aromatic ring), 4.69 (1H, t-d, J=8 Hz, J=4 Hz, proton at α-site of aspartic acid portion), 2.87 (1H, d-d, J=4 Hz, J=17 Hz, proton at β-site of aspartic acid portion), 2.72 (1H, d-d, J=4 Hz, J=17 Hz, proton at β-site of aspartic acid portion), 1.92 (3H, s, methyl group proton bound to 2-site of propene); $^{13}$C-NMR (heavy dimethyl sulfoxide, δ ppm): 172.8 (quaternary carbon, carbonyl carbon in aspartic acid portion), 172.0 (quaternary carbon, carbonyl carbon in aspartic acid portion), 169.0 (quaternary carbon, carbonyl carbon at 1-site of propene), 145.2 (quaternary carbon, carbon at 2'-site of cinnamyl aromatic ring), 139.8 (quaternary carbon, carbon at 4'-site of cinnamyl aromatic ring), 133.5 (quaternary carbon, carbon at 2-site of propene), 131.1 (CH, carbon at 6'-site of cinnamyl aromatic ring), 128.0 (CH, carbon at 3-site of propene), 117.7 (CH, carbon at 5'-site of cinnamyl aromatic ring), 117.2 (quaternary carbon, carbon at 1'-site of cinnamyl aromatic ring), 113.4 (CH, carbon at 3'-site of cinnamyl aromatic ring), 49.3 (CH, carbon at α-site of aspartic acid portion), 36.1 (CH$_2$, carbon at '3-site of aspartic acid portion), 14.6 (CH$_3$, methyl group carbon bound to 2-site of propene).

Synthesis of (E) N-3-methyloxycarbonylpropyl 3-(2-aminophenyl)-2-methyl-2-propenoic amide In 4 ml of dimethylformamide, 0.65 g (2.2 mmol) of (E) 3-(2-aminophenyl)-2-methyl-2-propenoic acid p-nitrophenyl ester and 0.40 g (2.6 mmol) of γ-aminobutanoic acid methyl ester hydrochloride (manufactured by Nakalai Tesque, Inc.) were dissolved; and, with 0.36 ml of triethylamine (manufactured by Wako Pure Chemical Industries, Ltd.) being added thereto, the mixture was reacted for 20 hours at room temperature. After the completion of the reaction was verified by TLC, ethyl acetate and water were added thereto. The resulting ethyl acetate layer was fractionated, washed several times with a 5% aqueous sodium hydrogencarbon ate solution and then with a saturated aqueous sodium chloride solution, and dried with magnesium sulfate anhydride. Thereafter, the solvent was evaporated under a reduced pressure, and the residue was refined by a silica gel column chromatography (developing solvent: methylene chloride/methanol=95/5), whereby 0.58 g of the aimed compound was obtained (yield: 95%).

The structure of this compound was verified by $^1$H-NMR and $^{13}$C-NMR.

$^1$H-NMR (heavy chloroform, δ ppm): 7.32 (1H, s, proton at 3-site of propene), 7.12 (1H, d, J=8 Hz, proton at 6'-site of cinnamyl aromatic ring), 7.07 (1H, dd, J=8 Hz, J=8 Hz, proton at 4'-site of cinnamyl aromatic ring), 6.76 (1H, d, J=8 Hz, proton at 3'-site of aromatic ring), 6.70 (1H, dd, J=8 Hz, J=8 Hz, proton at 5'-site of aromatic ring), 3.68 (3H, s, methylene group proton of methyl ester in GABA portion), 3.45 (2H, t, J=7 Hz, methylene group proton at γ-site of GABA portion), 2.45 (2H, t, J=7 Hz, methylene group proton at α-site of GABA portion), 2.02 (3H, s, methyl group proton bound to 2-site of propene), 1.94 (2H, t-t, J=7 Hz, J=7 Hz, methylene group proton at 3-site of GABA portion); $^{13}$C-NMR (heavy chloroform, δ ppm): 174.4 (quaternary carbon, carbonyl carbon in GABA portion), 170.21 (quaternary carbon, carbonyl carbon at 1-site of propene), 144.8 (quaternary carbon, carbon at 2'-site of cinnamyl aromatic ring), 132.3 (quaternary carbon, carbon at 2-site of propene), 131.4 (CH, carbon at 3-site of propene), 129.6 (CH, carbon at 4'-site of cinnamyl aromatic ring), 129.3 (CH, carbon at 6'-site of cinnamyl aromatic ring), 121.1 (quaternary carbon, carbon at 1'-site of cinnamyl aromatic ring), 118.0 (CH, carbon at 5'-site of cinnamyl aromatic ring), 115.6 (CH, carbon at 3'-site of cinnamyl aromatic ring), 51.9 ($CH_3$, methyl group carbon of methyl ester in GABA portion), 40.0 ($CH_2$, methylene group carbon at γ-site of GABA portion), 31.8($CH_2$, methylene group carbon at α-site of GABA portion), 24.2 ($CH_2$, methylene group carbon at β-site of GABA portion), 14.2 ($CH_3$, methyl group carbon bound to 2-site of propene).

Synthesis of (E) N-3-carboxypropyl 3-(2-aminophenyl)-2-methyl-2-propenoic amide Into 5 ml of methanol, 0.58 g (2.1 mmol) of (E) N-3-methyloxycarbonylpropyl 3-(2-aminophenyl)-2-methyl-2-propenoic amide was dissolved; and, with 5 ml of a 1-N aqueous sodium hydroxide solution being added thereto, the mixture was reacted for 12 hours at room temperature. After the pH of the reaction liquid was adjusted to about 4, the solvent was evaporated under a reduced pressure, and thus obtained crude product was refined by a silica gel column chromatography (developing solvent: dichloromethane/methanol=10/2), whereby 0.55 g of the aimed compound was obtained (yield: quantitative).

The structure of this compound was verified by $^1$H-NMR and $^{13}$C-NMR.

$^1$H-NMR (heavy dimethyl sulfoxide, δ ppm): 8.47 (1H, t, J=6 Hz, amide group proton), 7.47 (1H, d, J=7 Hz, proton at 3'-site of cinnamyl aromatic ring), 7.44–7.32 (3H, m, protons at 4'-, 5'-, and 6'-sites of cinnamyl aromatic ring), 7.26 (1H, s, proton at 3-site of propene), 3.22 (2H, t-d, J=6 Hz, J=6 Hz, methylene group proton at γ-site of GABA portion), 2.31 (2H, t, J=6 Hz, methylene group proton at α-site of GABA portion), 1.89 (3H, s, methyl group proton bound to 2-site of propene), 1.76 (2H, t-t, J=6 Hz, J=6 Hz, methylene group proton at 3-site of GABA portion) $^{13}$C-NMR (heavy dimethyl sulfoxide, δ ppm): 174.2 (quaternary carbon, carbonyl carbon in GABA portion), 170.0 (quaternary carbon, carbonyl carbon at 1-site of propene), 136.3 (quaternary carbon, carbon at 2'-site of cinnamyl aromatic ring), 132.4 (quaternary carbon, carbon at 2-site of propene), 130.1 (CH, carbon at 4'-site of cinnamyl aromatic ring), 130.1 (CH, carbon at 6'-site of cinnamyl aromatic ring), 129.4 (quaternary carbon, carbon at 1'-site of cinnamyl aromatic ring), 128.7 (CH, carbon at 5'-site of cinnamyl aromatic ring), 126.3 (CH, carbon at 3-site of propene), 122.7 (CH, carbon at 3'-site of cinnamyl aromatic ring), 38.4 ($CH_2$, methylene group carbon at γ-site of GABA portion), 31.3 ($CH_2$, methylene group carbon at α-site of GABA portion), 24.5 ($CH_2$, methylene group carbon at β-site of GABA portion), 14.6 ($CH_3$, methyl group carbon bound to 2-site of propene).

Synthesis of (E) N-L-glutamic acid diethyl ester 3-(4-dimethylamino-2-nitrophenyl)-2-methyl-2-propenoic amide Into 90 ml of tetrahydrofuran, 9.0 g (36 mmol) of (E) 3-(4-dimethylamino-2-nitrophenyl)-2-methyl-2-propenoic acid were dissolved; and, in a nitrogen atmosphere, 5.6 g of 1-hydroxybenzotriazole monohydrate (HOBt.$H_2$O) (manufactured by Kokusan Chemical Works), 9.1 g of glutamic acid diethyl ester hydrochloride (manufactured by Kokusan Chemical Works), and 3.8 g of triethylamine (manufactured by Wako Pure Chemical Industries, Ltd.) were added thereto. Further, with a solution in which 7.8 g of N,N'-dicyclohexyl carbodiimide (DCC) (manufactured by Wako Pure Chemical Industries, Ltd.) had been dissolved in 15 ml of tetradhydrofuran being added thereto, the mixture was stirred for one night at room temperature. After the completion of the reaction, the precipitate was filtered out, the filtrate was concentrated under a reduced pressure, and the resulting residue was dissolved in 500 ml of ethyl acetate. Thus obtained solution was successively washed with a saturated aqueous sodium hydrogencarbon ate solution, a 2-M aqueous citric acid solution, and the saturated aqueous sodium hydrogencarbon ate solution. The washed product was dried with magnesium sulfate anhydride and then concentrated, whereby a crude product was obtained. This crude product was refined by a column chromatography (silica gel (amino-modified type): Fuji Silysia Chem. Co., NH-DM1020, 1000 g; eluent: chloroform/methanol=20/1), whereby 12.1 g of the aimed compound were obtained (yield: 77.3%).

Synthesis of (E) N-L-glutamic acid 3-(2-amino-4-dimethylaminophenyl)-2-methyl-2-propenoic amide di-sodium salt In a dark room, 12.0 g (27.6 mmol) of (E) N-L-glutamic acid diethyl ester 3-(4-dimethylamino-2-nitrophenyl)-2-methyl-2-propenoic amide, 7.3 g (130.7 mmol) of iron powder (Koso Chem. Co.), 113.6 ml of acetic acid, and 8.7 ml of distilled water were put into a reaction vessel, and a stirring reaction was effected for 30 minutes at 92° C. while they were vigorously stirred. The completion of the reaction was verified by TLC, the mixture was cooled, and then iron powder and insoluble matters were filtered out. The resulting filtrate was concentrated under a reduced pressure, and 1000 ml of a saturated aqueous sodium hydrogencarbon ate were added to the concentrated product. After insoluble matters were filtered out, extraction with 300 ml of ethyl acetate was carried out three times. The extracted ethyl acetate solution was washed with a saturated aqueous sodium chloride solution, dried on magnesium sulfate anhydride, and then concentrated, whereby a crude product was obtained. This crude product was refined by a column chromatography (silica gel (amino-modified type): Fuji Silysia Chem. Co., NH-DM1020, 900 g; eluent: chloroform/methanol=20/1), whereby 4.5 g of (E) N-L glutamic acid diethyl ester 3-(2-amino-4-dimethylaminophenyl)-2-methyl-2-propenoic amide were obtained. This product was further dissolved in 45 ml of methanol; and, with 23 ml of a 1-N aqueous sodium hydroxide solution being added thereto, the mixture was stirred for one night at room temperature. After the solvent was evaporated therefrom, the reaction liquid was applied to a column using about 1000 ml of a solid-phase extraction filler DIAION HP-20 (manufactured by Mitsubishi Chemical Corp.) in order to eliminate excess alkalis and impurity salts, so as to be desalted as being eluted with water. Subsequently, it was eluted with a 10% aqueous methanol solution, and the resulting product was lyophilized, whereby 2.9 g of the aimed product were obtained (yield: 26.8%).

The structure of this compound was verified by $^1$H-NMR and $^{13}$C-NMR.

$^1$H-NMR (heavy dimethyl sulfoxide, δ ppm): 7.45 (1H, d, J=6 Hz, amide group proton), 7.11 (1H, s, proton at 3-site of propenoic acid), 6.89 (1H, d, J=9 Hz, proton at 6'-site of aromatic ring), 6.06 (1H, s, proton at 3'-site of aromatic ring), 6.04 (1H, d, J=9 Hz, proton at 5'-site of aromatic ring), 4.85 (2H, bs, aniline-type amino group proton), 3.92 (1H, ddd, J=5 Hz, J=7 Hz, J=6 Hz, proton at α-site of glutamic acid portion), 2.89 (6H, s, methyl group proton of dimethylamino group), 2.04 (3H, s, methyl group proton at 2-site of propene), 2.42–2.00 (4H, m, methylene group protons at β- and γ-sites of glutamic acid portion), 1.95 (3H, s, methyl group proton bound to 2-site of propenoic acid); $^3$C-NMR (heavy dimethyl sulfoxide, δ ppm): 173.6 (quaternary carbon, carbonyl carbon in glutamic acid portion), 172.9 (quaternary carbon, carbonyl carbon in glutamic acid portion), 167.8 (quaternary carbon, carbonyl carbon at 1-site), 151.0 (quaternary carbon, carbon at 4'-site of aromatic ring), 147.7 (quaternary carbon, carbon at 2'-site of aromatic ring), 130.1 (CH, carbon at 6'-site of aromatic ring), 129.1 (CH, carbon at 3-site of propenoic acid), 128.1 (quaternary carbon, carbon at 2-site of propene), 109.6 (quaternary carbon, carbon at 1'-site of aromatic ring), 101.5 (CH, carbon at 5'-site of aromatic ring), 98.2 (CH, carbon at 3'-site of aromatic ring), 53.6 (CH, carbon at α-site of glutamic acid portion), 39.8 ($CH_3$, methyl group carbon of dimethylamino group), 30.0 ($CH_2$, carbon at γ-site of glutamic acid portion), 27.9 ($CH_2$, carbon at β-site of glutamic acid portion), 14.4 ($CH_3$, methyl group carbon bound to 2-site of propene).

Synthesis of (E) N-3-ethyloxycarbonylpropyl 3-(4-dimethylamino-2-nitrophenyl)-2-methyl-2-propenoic amide Into 60 ml of tetrahydrofuran, 5.5 g (22.0 mmol) of (E) 3-(4-dimethylamino-2-nitrophenyl)-2-methyl-2-propenoic acid were dissolved; and, in a nitrogen atmosphere, 3.4 g of 1-hydroxybenzotriazole monohydrate ($HOBt.H_2O$) (manufactured by Kokusan Chemical Works), 3.9 g of γ-aminobutanoic acid ethyl ester, and 2.3 g of triethylamine (manufactured by Wako Pure Chemical Industries, Ltd.) were added thereto. Further, with a solution in which 7.8 g of N,N' -dicyclohexyl carbodiimide (DCC) (manufactured by Wako Pure Chemical Industries, Ltd.) had been dissolved in 10 ml of tetradhydrofuran being added thereto, the mixture was stirred for one night at room temperature. After the completion of the reaction, the precipitate was filtered out, the filtrate was concentrated under a reduced pressure, and the resulting residue was dissolved in 400 ml of ethyl acetate. Thus obtained solution was successively washed with a saturated aqueous sodium hydrogencarbon ate solution, a 2-M aqueous citric acid solution, and the saturated aqueous sodium hydrogencarbon ate solution. The washed product was dried with magnesium sulfate anhydride and then concentrated, whereby a crude product was obtained. This crude product was refined by a column chromatography (silica gel (amino-modified type): Fuji Silysia Chem. Co., NH-DM1020, 1000 g; eluent: chloroform/methanol=20/1), whereby 7.77 g of the aimed compound were obtained (yield: 97.3%).

Synthesis of (E) N-γ-aminobutyric acid 3-(2-amino-4-dimethylaminophenyl)-2-methyl-2-propenoic amide sodium salt In a dark room, 7.7 g (21.2 mmol) of (E) N-ethyloxycarbonylpropyl 3-(4-dimethylamino-2-nitrophenyl)-2-methyl-2-propenoic amide, 5.5 g (98.5 mmol) of iron powder (Koso Chem. Co.), 120 ml of acetic acid, and 6.92 ml of distilled water were put into a reaction vessel, and a stirring reaction was effected for 15 hours at room temperature while they were vigorously stirred. After the completion of the reaction was verified by TLC, the reaction liquid was poured into a saturated aqueous sodium hydrogencarbon ate solution; and extraction was carried out with 500 ml of ethyl acetate being added thereto. The resulting organic layer was washed with a saturated aqueous sodium chloride solution, dried on magnesium sulfate anhydride, and then concentrated, whereby a crude product was obtained. This crude product was further refined by a column chromatography (silica gel (amino-modified type): Fuji Silysia Chem. Co., NH-DM1020, 900 g; eluent: chloroform/methanol=20/1), whereby 5.87 g of (E) N-3-ethyloxycarbonylpropyl 3-(2-amino-4-dimethylaminophenyl)-2-methyl-2-propenoic amide were obtained. This product was further dissolved in 60 ml of methanol; and, with 27 ml of a 1-N aqueous sodium hydroxide solution being added thereto, the mixture was stirred for one night at room temperature. After the solvent was evaporated therefrom, the reaction liquid was applied to a column using about 1000 ml of a solid-phase extraction filler DIAION HP-20 (manufactured by Mitsubishi Chemical Corp.) in order to eliminate excess alkalis and impurity salts, so as to be desalted as being eluted with water. Subsequently, it was eluted with a 10% aqueous methanol solution, and the resulting product was lyophilized, whereby 4.76 g of the aimed product were obtained (yield: 69.2%).

The structure of this compound was verified by $^1$H-NMR and $^{13}$C-NMR.

$^1$H-NMR (heavy dimethyl sulfoxide, δ ppm): 8.89 (1H, d, J=4 Hz, amide group proton, 7.02 (1H, s, proton at 3-site of propenoic acid), 6.90 (1H, d, J=8 Hz, proton at 6'-site of aromatic ring), 6.03 (1H, s, proton at 3'-site of aromatic ring), 6.01 (1H, d, J=8 Hz, proton at 5'-site of aromatic ring), 5.05 (2H, bs, aniline-type amino group proton), 3.14 (2H, dt, J=4 Hz, J=7 Hz, proton at α-site of γ-aminobutanoic acid portion), 2.93 (6H, s, methyl group proton of dimethylamino group), 2.06 (2H, s, proton at γ-site of γ-aminobutanoic acid portion), 1.91 (3H, s, methyl group proton bound to 2-site of propenoic acid), 1.69 (2H, tt, J=7 Hz, J=7 Hz, proton at β-site of γ-aminobutanoic acid portion); $^{13}$C-NMR (heavy dimethyl sulfoxide, δ ppm): 177.2 (quaternary carbon, carbonyl carbon in γ-butanoic acid portion), 169.6 (quaternary carbon, carbonyl carbon at 1-site), 150.9 (quaternary carbon, carbon at 2'-site of aromatic ring), 147.8 (quaternary carbon, carbon at 4'-site of aromatic ring), 129.9 (CH, carbon at 6'-site of aromatic ring), 129.9 (CH, carbon at 3-site of propenoic acid), 128.3 (quaternary carbon, carbon at 2-site of propene), 128.1 (CH, carbon at 3-site of propenoic acid), 109.3 (quaternary carbon, carbon at 1'-site of aromatic ring), 101.3 (CH, carbon at 5'-site of aromatic ring), 98.0 (CH, carbon at 3'-site of aromatic ring), 40.5 ($CH_2$, carbon at α-site of γ-aminobutanoic acid portion), 39.9 ($CH_3$, methyl group carbon of dimethylamino group), 36.5 ($CH_2$, carbon at γ-site of γ-aminobutanoic acid portion), 25.4 ($CH_2$, carbon at β-site of γ-aminobutanoic acid portion), 14.6 ($CH_3$, methyl group carbon bound to 2-site of propene).

Synthesis of (E) 3-[4,5-dimethoxy-2-(trimethylsilylethoxycarbonyl)aminophenyl]-2-methyl-2-propenoic acid In a dark room, 12.2 g (46.2 mmol) of (E) ethyl 3-(2-amino-4,5-dimethoxyphenyl)-2-methyl-2-propenate were dissolved in 120 ml of acetonitrile; and, in a nitrogen atmosphere, 7.6 g (55.4 mmol) of pulverized potassium carbon ate were added thereto while being cooled with ice. While the turbid reaction liquid was vigorously stirred, 10 g (55.4 mmol) of triethylsilylethoxycarbonyl chloride (Teoc-Cl) were slowly added dropwise thereto, and the mixture was stirred at room temperature for one night. The resulting reaction liquid was poured into 500 ml of cold water, and extraction with 300 ml of ethyl acetate was carried out. Thus obtained ethyl acetate solution was successively washed with water, an aqueous sodium hydrogencarbon ate solution, and a saturated aqueous sodium chloride solution; and then was dried with sodium sulfate anhydride. Thereafter, the solvent was evaporated, whereby 13.5 g of a crude product were obtained. This crude product was refined by a silica gel column chromatography (eluent: normal hexane/ethyl acetate=3/1), whereby 7.0 g of (E) ethyl 3-[4,5-dimethoxy-2-(trimethylsilylethoxycarbonyl)aminophenyl]-2-methyl-2-propenate were obtained. This product was further dissolved in 30 ml of dioxane; and, with 25 ml of a 1-N aqueous sodium hydroxide solution being added thereto, the mixture was stirred at 40° C. After the completion of the reaction was verified by TLC, 150 ml of distilled water were added to the reaction liquid. After its pH was adjusted to 3 with 1-N hydrochloric acid, the precipitated crystal was filtered out and dried, whereby 5.6 g of the aimed compound were obtained (yield: 32%).

The structure of this compound was verified by $^1$H-NMR and $^{13}$C-NMR.

$^1$H-NMR (heavy chloroform, δ ppm): 8.81 (1H, bs, amide group proton), 7.56 (1H, s, proton at 3-site of propenoic acid), 6.97 (1H, s, proton at 3'-site of aromatic ring), 6.89 (1H, s, proton at 6'-site of aromatic ring), 4.12 (2H, t, J=8 Hz, methylene group proton at α-site of trimethylsilylethoxy group), 3.77 (6H, s, methyl group proton of methoxy group), 1.94 (3H, s, methyl group proton bound to 2-site of propenoic acid), 0.94 (2H, t, J=8 Hz, methylene group proton at β-site of trimethylsilylethoxy group), 0.03 (9H, s, methyl group proton of trimethylsilylethoxy group); $^{13}$C-NMR (heavy chloroform, δ ppm): 169.4 (quaternary carbon, carbonyl group carbon at 1-site of propenoic acid), 154.6 (quaternary carbon, carbonyl carbon of trimethylsilylethoxycarbonyl group), 148.7 (quaternary carbon, carbon at 4'-site of aromatic ring), 145.7 (quaternary carbon, carbon at 5'-site of aromatic ring), 134.9 (CH, carbon at 3-site of propenoic acid), 130.3 (quaternary carbon, carbon at 2'-site of aromatic ring), 127.8 (quaternary carbon, carbon at 2-site of propenoic acid), 112.3 (CH, carbon at 6'-site of aromatic ring), 62.1 (CH$_2$, methylene group carbon at β-site of trimethylsilylethoxy group), 55.7 (CH$_3$, methyl group carbon of methoxy group), 55.5 (CH$_3$, methyl group carbon of methoxy group), 17.3 (CH$_2$, methylene group carbon at α-site of trimethylsilylethoxy group), 14.0 (CH$_3$, methyl group carbon bound to 2-site of propenoic acid), −1.5 (CH$_3$, methyl group carbon of trimethylsilylethoxy group).

Synthesis of (E) N-(N-methyl)-D-aspartic acid 3-(2-amino-4,5-dimethoxyphenyl)-2-methyl-2-propenoic amide In a dark room, 4.5 g (11.4 mmol) of (E) 3-[4,5-dimethoxy-2-(trimethylsilylethoxycarbonyl)aminophenyl]-2-methyl-2-propenoic acid were dissolved in 50 ml of tetrahydrofuran; and, in a nitrogen atmosphere, with 1.83 g of 1-hydroxybenzotriazole monohydrate (HOBt-H$_2$O) (manufactured by Kokusan Chemical Works), 3.10 g of N-methyl-D-aspartic acid di-t-butyl ester, 1.15 g of N-methyl morpholine (manufactured by Wako Pure Chemical Industries, Ltd.), and 2.47 g of N,N'-dicyclohexyl carbodiimide (DCC) (manufactured by Wako Pure Chemical Industries, Ltd.) being added thereto, the mixture was stirred for 10 days at room temperature. After the completion of the reaction, the precipitate was filtered out, and the filtrate was concentrated under a reduced pressure. The resulting residue was dissolved in 200 ml of ethyl acetate. This organic layer was successively washed with a saturated aqueous sodium hydrogencarbon ate solution, a 20% aqueous citric acid solution, the saturated aqueous sodium hydrogencarbon ate solution, and a saturated aqueous sodium chloride solution. Thus washed product was dried with magnesium sulfate anhydride and then was concentrated, whereby a crude product was obtained. This crude product was refined by a column chromatography (silica gel (amino-modified type): Fuji Silysia Chem. Co., NH-DM 1020), whereby 6.84 g of (E) N-(N-methyl)-D-aspartic acid di-t-butyl ester 3-(2-amino-4,5-dimethoxyphenyl)-2-methyl-2-propenoic amide were obtained (yield: 94.4%). This product was further dissolved in 200 ml of methanol; and, with 1-N hydrochloric acid being added thereto, the mixture was stirred for one month at room temperature. After the completion of the protective group liberating reaction was verified, the reaction liquid was made alkaline with 1-N sodium hydroxide, and then was applied to a column using a solid-phase extraction filler DIAION HP-20 (manufactured by Mitsubishi Chemical Corp.) in order to eliminate excess alkalis and impurity salts, so as to be desalted as being eluted with water. Subsequently, it was eluted with a 10% aqueous methanol solution, and the resulting product was lyophilized, whereby 3.04 g of the aimed product were obtained (yield: 71.0%).

The structure of this compound was verified by $^1$H-NMR and $^{13}$C-NMR.

$^1$H-NMR (heavy water, δ ppm): 6.85 (1H, s, proton at 6'-site of aromatic ring), 6.61 (1H, s, proton at 3'-site of aromatic ring), 6.48 (1H, s, methine group proton at 3-site of propenoic acid), 5.02 (1H, dd, J=9 Hz, J=6 Hz, methine group proton at α-site of aspartic acid portion), 3.83 (3H, s, methyl group proton of methoxy group), 3.81 (3H, s, methyl group proton of methoxy group), 3.20–2.79 (2H, m, methylene group proton at β-site of aspartic acid portion), 2.90 (3H, s, methyl group proton bound to nitrogen in aspartic acid portion), 1.96 (3H, s, methyl group proton bound to 2-site of propenoic acid); $^{13}$C-NMR (heavy water, δ ppm): 177.2 (quaternary carbon, carbonyl carbon in aspartic acid portion), 176.3 (quaternary carbon, carbonyl carbon in aspartic acid portion), 174.7 (quaternary carbon, carbonyl carbon at 1-site of propenoic acid), 149.8 (quaternary carbon, carbon at 4'-site of aromatic ring), 141.9 (quaternary carbon, 6-carbon at 2'-site of aromatic ring), 139.4 (quaternary carbon, carbon at 5'-site of aromatic ring), 134.2 (quaternary carbon, carbon at 2-site of propenoic acid), 126.9 (CH, methine group carbon at 3-site of propenoic acid), 114.9 (quaternary carbon, carbon at 1'-site of aromatic ring), 114.6 (CH, carbon at 6'-site of aromatic ring), 102.5 (CH, carbon at 3'-site of aromatic ring), 62.1 (CH, methine group carbon at α-site in aspartic acid portion), 57.4 (CH$_3$, methyl group carbon of methoxy group), 56.4 (CH$_3$, methyl group carbon of methoxy group), 36.0 (CH$_2$, methylene group carbon at β-site in aspartic acid portion),30.3 (CH$_3$, methyl group carbon bound to nitrogen in aspartic acid portion), 15.8 (CH$_3$, methyl group carbon bound to 2-site of propenoic acid).

Synthesis of (E) N-L-glutamine 3-(2-amino-4,5-dimethoxyphenyl)-2-methyl-2-propenoic amide In a dark room, 4.4 g (11.1 mmol) of (E) 3-[4,5-dimethoxy-2-(trimethylsilylethoxycarbonyl)aminophenyl]-2-methyl-2-propenoic acid were dissolved in 45 ml of tetrahydrofuran. Thus obtained mixture was cooled to −10° C. and, with 1.7 g of isobutylchloroformate being added thereto, was stirred for 30 minutes in a nitrogen atmosphere. With 1.2 g of N-methylmorpholine (manufactured by Wako Pure Chemical Industries, Ltd.) and a solution in which 3 g of glutamine t-butyl ester hydrochloride (manufactured by Kokusan Chemical Works) had been dissolved in 35 ml of dimethylformamide being added thereto, the temperature of the mixture was gradually raised to room temperature, and the mixture was stirred for 1 hour at room temperature. After the completion of the reaction, the solvent was evaporated under a reduced pressure, and 200 ml of ethyl acetate and 100 ml of water were added to the residue. The resulting organic layer was successively washed with a 5% aqueous sodium hydrogencarbon ate solution, water, 1-N hydrochloric acid, and water. The washed layer was dried with magnesium sulfate anhydride and then concentrated, whereby a crude product was obtained. This crude product was refined by a silica gel column chromatography, whereby 4.64 g of (E) N-glutamine t-butyl ester 3-(2-amino-4,5-dimethoxyphenyl)-2-methyl-2-propenoic amide were obtained (yield: 73.9%). It was further dissolved in 40 ml of dichloromethane; and, with 5 ml of trifluoroacetic acid (manufactured by Wako Pure Chemical Industries, Ltd.) being added thereto, the mixture was stirred for 24 hours at 30° C. After the completion of the protective group liberating reaction was verified, the mixture was concentrated under a reduced pressure, and the residue was dissolved in ion-exchanged water and lyophilized, whereby 2.7 g of the aimed product were obtained (yield: 93.8%).

The structure of this compound was verified by $^1$H-NMR and $^{13}$C-NMR.

$^1$H-NMR(heavy dimethylsulfoxide, δ ppm): 7.02 (1H, s, proton at 6'-site of aromatic ring), 6.92 (1H, s, proton at 3'-site of aromatic ring), 7.38 (1H, s, methine group proton at 3-site of propenoic acid), 4.28 (1H, dd, J=12 Hz, J=8 Hz, methine group proton at α-site of glutamine portion), 3.79 (6H, s, methyl group proton of methoxy group), 2.22 (2H, t, J=7 Hz, methine group proton at γ-site of glutamine portion), 2.14–1.90 (2H, m, methine group proton at β-site of glutamine portion), 1.98 (3H, s, methyl group proton bound to 2-site of propenoic acid); $^{13}$C-NMR (heavy dimethyl sulfoxide, δ ppm): 174.0 (quaternary carbon, carbonyl carbon in glutamine portion), 173.5 (quaternary carbon, carbonyl carbon in glutamine portion), 168.4 (quaternary carbon, carbonyl carbon at 1-site of propenoic acid portion), 148.9 (quaternary carbon, carbon at 4'-site of aromatic ring), 147.4 (quaternary carbon, carbon at 5'-site of aromatic ring), 127.5 (CH, methine group carbon at 3-site of propenoic acid), 134.7 (quaternary carbon, carbon at 2'-site of aromatic ring), 124.0 (quaternary carbon, carbon at 2-site of propenoic acid portion), 117.4 (quaternary carbon, carbon at 1'-site of aromatic ring), 113.6 (CH, carbon at 5'-site of aromatic ring), 56.0 (CH$_3$, methyl group carbon of methoxy group), 55.8 (CH$_3$, methyl group carbon of methoxy group), 52.4 (CH, methine group carbon at α-site of glutamine portion), 31.6 (CH$_2$, methylene group carbon at γ-site of glutamine portion), 26.5 (CH$_2$I,methylene group carbon at β-site of glutamine portion), 14.5 (CH$_3$, methyl group carbon bound to 2-site of propenoic acid portion).

Release of Amino Acid upon Irradiation with Light

Figure 5A:
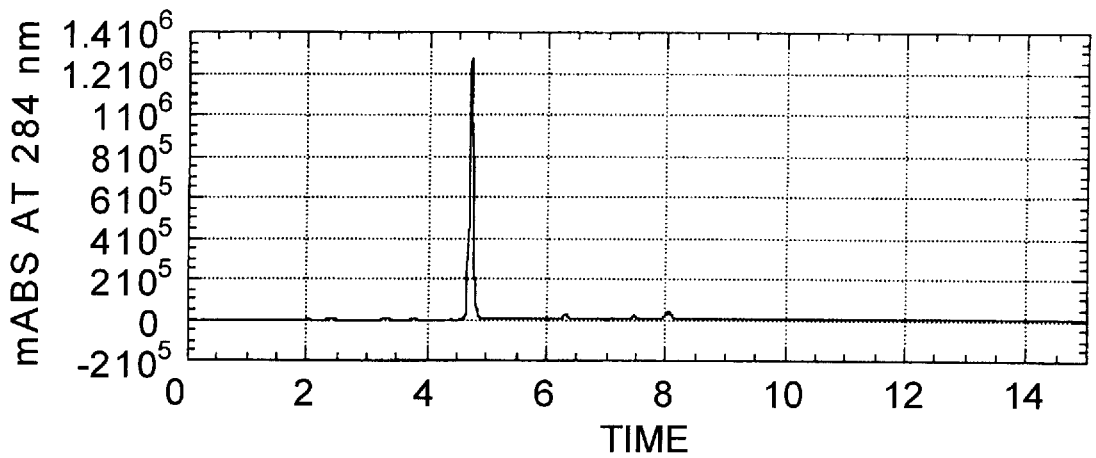
FIG. 5A depicts the HPLC chromatogram of an aqueous solution of cage glutamic acid.
Figure 5B:
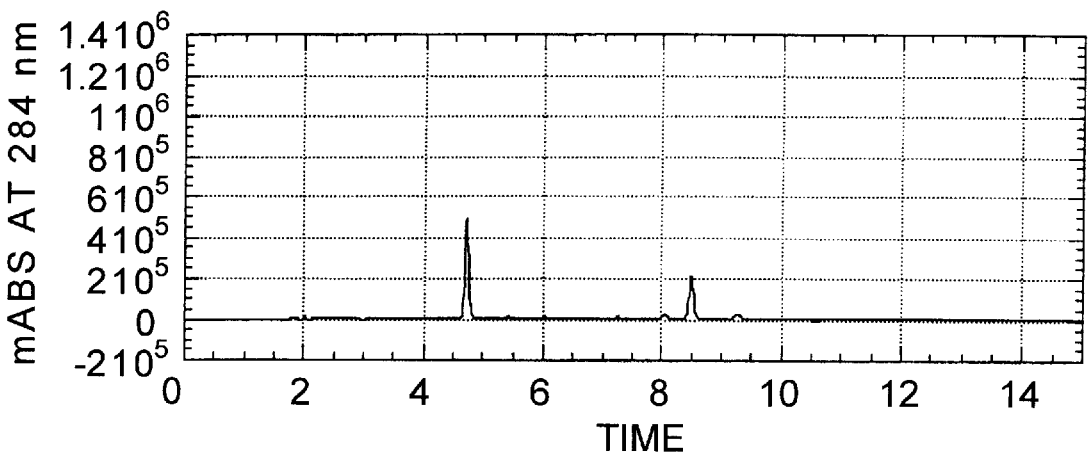
FIG. 5B depicts the HPLC chromatogram of an aqueous solution of caged glutamic acid after irradiation with monochromatic light.

An aqueous solution of the caged glutamic acid obtained in the foregoing (100 mM) was irradiated with monochromatic light at 320 nm for 30 minutes, and the resulting product was separated and analyzed by use of HPLC under the following condition. As a result, it was verified that carbostyril had been generated (FIGS. 5A and 5B).

HPLC condition:
Column: manufactured by Kanto Kagaku, Mightysil RP-18, 150-4.6
Eluent solvent: acetonitrile/water containing 0.05% trifluoroacetic acid (gradient condition: 10/90 to 70/30 (20 minutes)

| Eluting rate: | 1 ml/min |
|---|---|
| Holding time: | |
| caged glutamate | 4.8 min |
| carbostyril | 8.5 min |

Figure 6A:
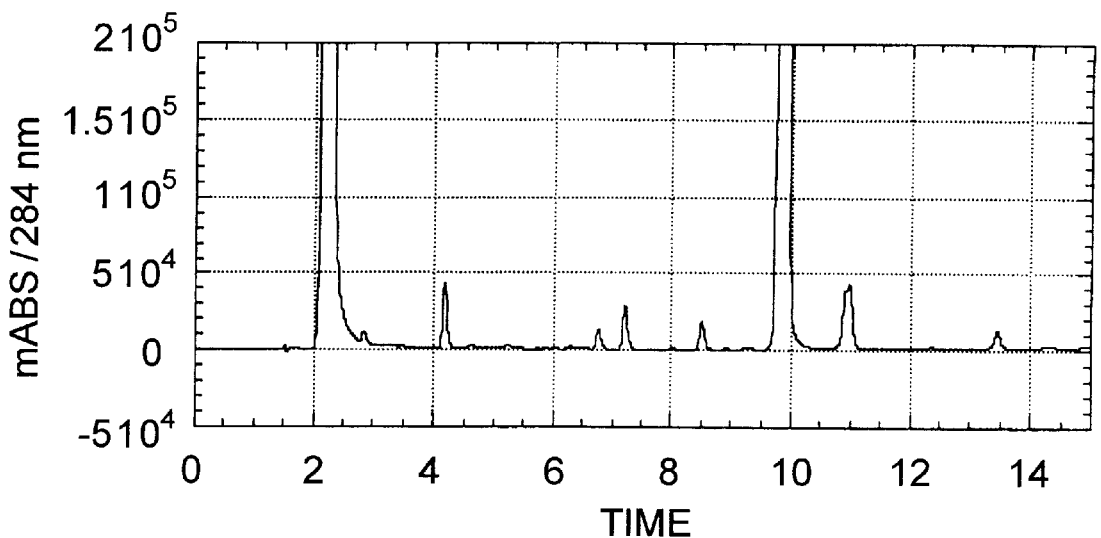
FIGS. 6A and 6B depict the HPLC chromatograms of a caged glutamic acid solution after irradiation with monochromatic light and contact with dansyl chloride.
Figure 6B:
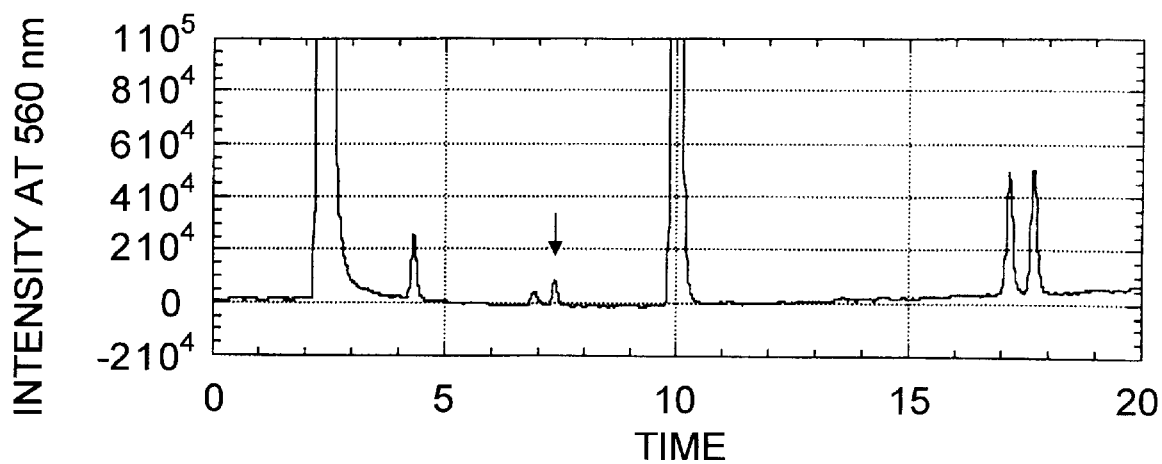

For detecting released glutamic acid, dansyl chloride was added to the above-mentioned sample irradiated with light, so as to form a dansyl derivative of glutamic acid. Thus obtained product was separated and analyzed under the following condition by use of HPLC, whereby it was verified that dansyl glutamic acid had been generated (FIGS. 6A and 6B).

Column: manufactured by Kanto Kagaku, Mightysil RP-18, 150-4.6
Eluent solvent: acetonitrile/water containing 0.05% trifluoroacetic acid (gradient condition: 10/90 to 70/30 (20 minutes)
Eluting rate: 1 ml/min
Holding time: dansyl glutamic acid 7.2 min The caged amino acid compounds in accordance with the present invention have specific structures as explained in the foregoing, and can release a specific amount of amino acid at a specific place at a specific time upon irradiation with light. Also, the amount of released amino acid can be measured when a strong fluorescence from a concurrently-generated carbostyril derivative is determined.

What is claimed is:
1. A caged amino acid expressed by the following formula 1:

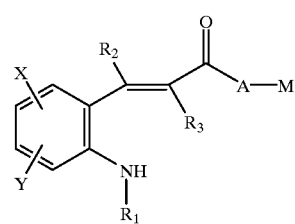

formula 1 where X and Y independently represent one kind selected from the group consisting of a hydrogen atom, a halogen atom, an alkyl group having a carbon number from 1 to 4, an alkyloxy group having a carbon number from 1 to 4, an alkylamino group having a carbon number from 1 to 4, and a benzo group, and may be identical or different from each other; R$_1$ represents one kind selected from the group consisting of a hydrogen atom and an alkyl group having a carbon number from 1 to 4; R$_2$ and R$_3$ independently represent one kind selected from the group consisting of a hydrogen atom and an alkyl group having a carbon number from 1 to 4, and may be identical or different from each other; A represents an amino acid residue covalenty linked at its α-amino group and selected from the group consisting of glycine, alanine, valine, leucine, isoleucine, serine, threonine, aspartic acid, glutamic acid, γ-aminobutanoic acid, N-methyl-D-aspartic acid, asparagine, glutamine, lysine, hydroxylysine, arginine, cysteine, cystine, methionine, phenylalaninc, tyrosine, tryptophan, histidine, proline, and 4-hydroxyproline; and M represents one kind selected from the group consisting of a hydrogen atom, an alkali metal, and an alkaline-earth metal.

2. A caged amino acid according to claim 1, wherein said caged amino acid is one kind selected from the group consisting of the caged amino acids represented by the following formulae 2 to 18:

formula 2

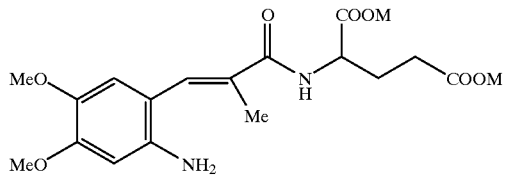

where M represents one kind selected from the group consisting of a hydrogen atom, an alkali metal, and an alkaline-earth metal;

formula 3

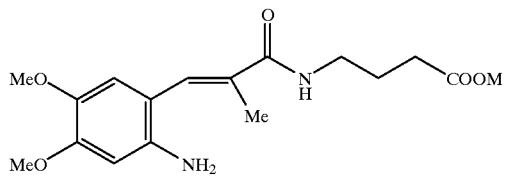

where M represents one kind selected from the group consisting of a hydrogen atom, an alkali metal, and an alkaline-earth metal;

formula 4

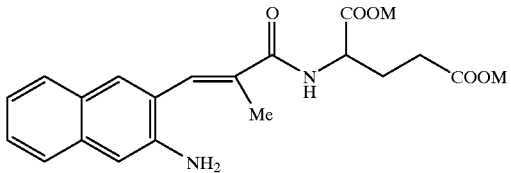

where M represents one kind selected from the group consisting of a hydrogen atom, an alkali metal, and an alkaline-earth metal;

formula 5

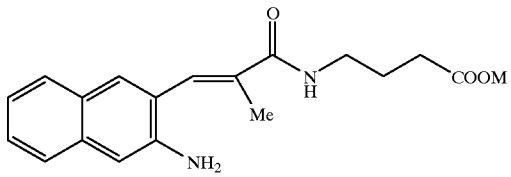

where M represents one kind selected from the group consisting of a hydrogen atom, an alkali metal, and an alkaline-earth metal;

formula 6

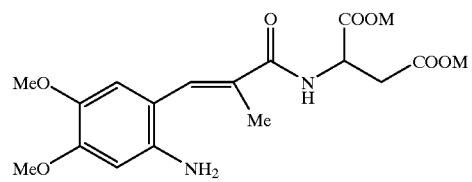

where M represents one kind selected from the group consisting of a hydrogen atom, an alkali metal, and an alkaline-earth metal;

formula 7

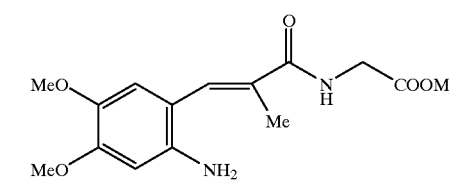

where M represents one kind selected from the group consisting of a hydrogen atom, an alkali metal, and an alkaline-earth metal;

formula 8

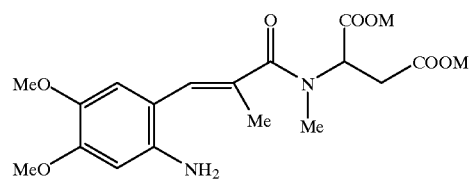

where M represents one kind selected from the group consisting of a hydrogen atom, an alkali metal, and an alkaline-earth metal;

formula 9

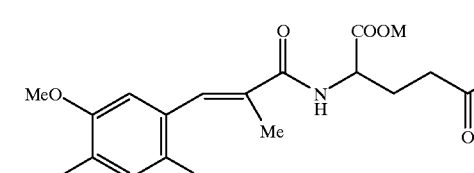

where M represents one kind selected from the group consisting of a hydrogen atom, an alkali metal, and an alkaline-earth metal;

formula 10

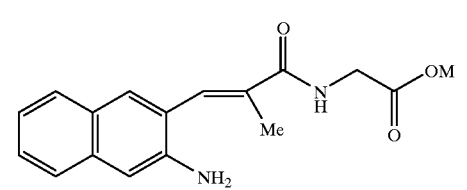

where M represents one kind selected from the group consisting of a hydrogen atom, an alkali metal, and an alkaline-earth metal;

formula 11

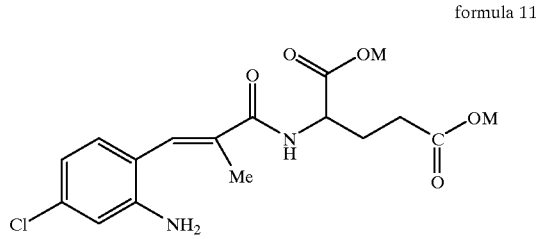

where M represents one kind selected from the group consisting of a hydrogen atom, an alkali metal, and an alkaline-earth metal;

formula 12

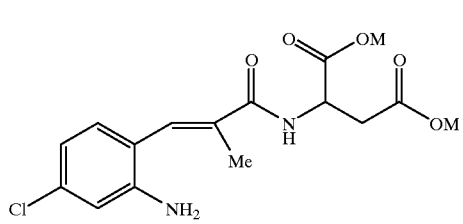

where M represents one kind selected from the group consisting of a hydrogen atom, an alkali metal, and an alkaline-earth metal;

formula 13

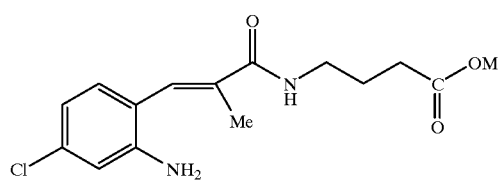

where M represents one kind selected from the group consisting of a hydrogen atom, an alkali metal, and an alkaline-earth metal;

formula 14

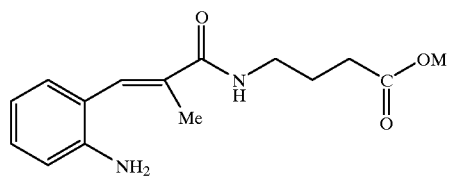

where M represents one kind selected from the group consisting of a hydrogen atom, an alkali metal, and an alkaline-earth metal;

formula 15

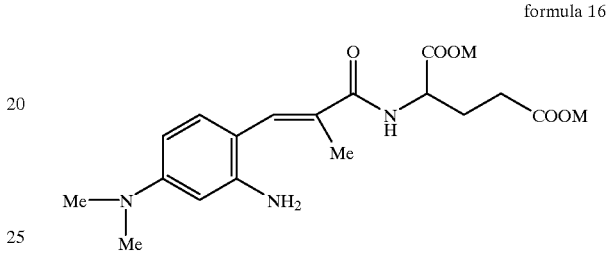

where M represents one kind selected from the group consisting of a hydrogen atom, an alkali metal, and an alkaline-earth metal;

formula 16

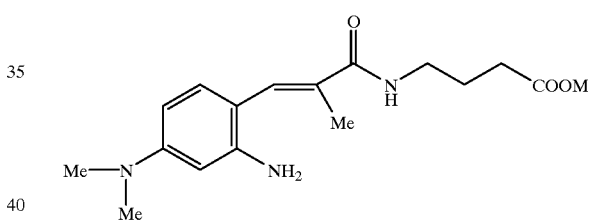

where M represents one kind selected from the group consisting of a hydrogen atom, an alkali metal, and an alkaline-earth metal;

formula 17

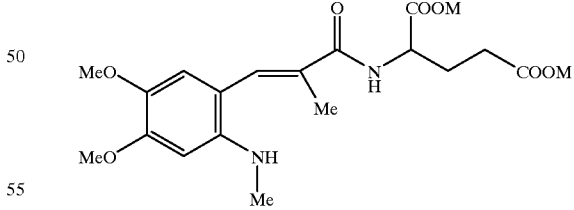

where M represents one kind selected from the group consisting of a hydrogen atom, an alkali metal, and an alkaline-earth metal;

formula 18 where M represents one kind selected from the group consisting of a hydrogen atom, an alkali metal, and an alkaline-earth metal.

* * * * *